(12) United States Patent
Zemach et al.

(10) Patent No.: US 12,428,639 B2
(45) Date of Patent: Sep. 30, 2025

(54) PLANT DNA METHYLTRANSFERASES AND USES THEREOF

(71) Applicant: Ramot at Tel-Aviv University Ltd., Tel-Aviv (IL)

(72) Inventors: Assaf Zemach, Tel-Aviv (IL); Nir Ohad, Tel-Aviv (IL); Rafael Yaari, Tel-Aviv (IL); Aviva Katz, Tel-Aviv (IL); Katherine Domb, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1031 days.

(21) Appl. No.: 17/436,167

(22) PCT Filed: Mar. 4, 2020

(86) PCT No.: PCT/IL2020/050254
§ 371 (c)(1),
(2) Date: Sep. 3, 2021

(87) PCT Pub. No.: WO2020/178831
PCT Pub. Date: Sep. 10, 2020

(65) Prior Publication Data
US 2022/0135969 A1 May 5, 2022

Related U.S. Application Data

(60) Provisional application No. 62/813,805, filed on Mar. 5, 2019.

(51) Int. Cl.
*C12N 15/11* (2006.01)
*A01H 11/00* (2006.01)
*C12N 9/10* (2006.01)
*C12N 9/22* (2006.01)

(52) U.S. Cl.
CPC ............ *C12N 15/111* (2013.01); *A01H 11/00* (2013.01); *C12N 9/1007* (2013.01); *C12N 9/22* (2013.01); *C12N 2310/20* (2017.05); *C12Y 201/01037* (2013.01)

(58) Field of Classification Search
CPC .............. C07K 2319/00; C12N 9/1007; C12Y 201/01037
See application file for complete search history.

(56) References Cited

U.S. PATENT DOCUMENTS

| 2015/0044772 A1 | 2/2015 | Zhao |
| 2019/0032049 A1 | 1/2019 | Naldini et al. |

FOREIGN PATENT DOCUMENTS

| WO | WO 2017/208247 | 12/2017 |
| WO | WO 2020/178831 | 9/2020 |

OTHER PUBLICATIONS

Vojta A, Dobrinić P, Tadić V, Bočkor L, Korać P, Julg B, Klasić M, Zoldoš V. Repurposing the CRISPR-Cas9 system for targeted DNA methylation. Nucleic Acids Res. Jul. 8, 2016;44(12):5615-28. doi: 10.1093/nar/gkw159. Epub Mar. 11, 2016. PMID: 26969735; PMCID: PMC4937303. (Year: 2016).*
Sónia Alexandra Gomes Pereira, Deciphering the role of antherozoid specific DNA methyltransferases in Physcomitrella patens. Thesis to obtain the Master of Science Degree in Biotechnology. Nov. 2015. (Year: 2015).*
He XJ, Chen T, Zhu JK. Regulation and function of DNA methylation in plants and animals. Cell Res. Mar. 2011;21(3):442-65. doi: 10.1038/cr.2011.23. Epub Feb. 15, 2011. PMID: 21321601; PMCID: PMC3152208. (Year: 2011).*
Supplementary European Search Report and the European Search Opinion Dated Nov. 10, 2022 From the European Patent Office Re. Application No. 20765538.2. (6 pages).
Niemann "Transgenic pigs expressing plant genes", Proceedings of the National Academy of Sciences, 101(19):7211-7212, May 11, 2004.
International Search Report and the Written Opinion Dated Jun. 9, 2020 From the International Searching Authority Re. Application No. PCT/IL2020/050254. (12 Pages).
Goll et al. "Eukaryotic Cytosine Methyltransferases", Annual Review of Biochemistry, 74: 481-514, Published Online Mar. 11, 2005.
Hellman "Precise Epigenome Therapy Using DNA Methylation and Demethylation Enzymes Fused to CRISPRdCas9", Yissum Technology Trader, The Hebrew University of Jeruslaem, Israel, 2 P., Apr. 8, 2019.
Lei et al. "DNA Methylation and De-Methylation Using Hybrid Site-Targeting Proteins", Genome Biology, 19(187): 1-12, Nov. 6, 2018.
NCBI "Uncharacterized Protein LOC9640092 Isoform X2 [Selaginella Moellendorffii]", Database NCBI [Online], GenBank Accession No. XP 002971634.2, Database Accession No. XP_002971634, Apr. 12, 2018.
Yaari et al. "RdDM-Independent De Novo and Heterochromatin DNA Methylation by Plant CMT and DNMT3 Orthologs", Nature Communications, Nature Communications, 10: 10 P., Apr. 8, 2019.
Zemach et al. "Genome-Wide Evolutionary Analysis of Eukaryotic DNA Methylation", Science, 328(5980): 916-919, Apr. 15, 2010.

* cited by examiner

*Primary Examiner* — Fereydoun G Sajjadi
*Assistant Examiner* — Qinhua Gu

(57) ABSTRACT

An isolated polynucleotide encoding a fusion protein which comprises a DNA targeting moiety linked to a catalytic domain of a plant DNA methyltransferase 3 (DNMT3) protein is disclosed. Uses thereof are also disclosed.

8 Claims, 24 Drawing Sheets
Specification includes a Sequence Listing.

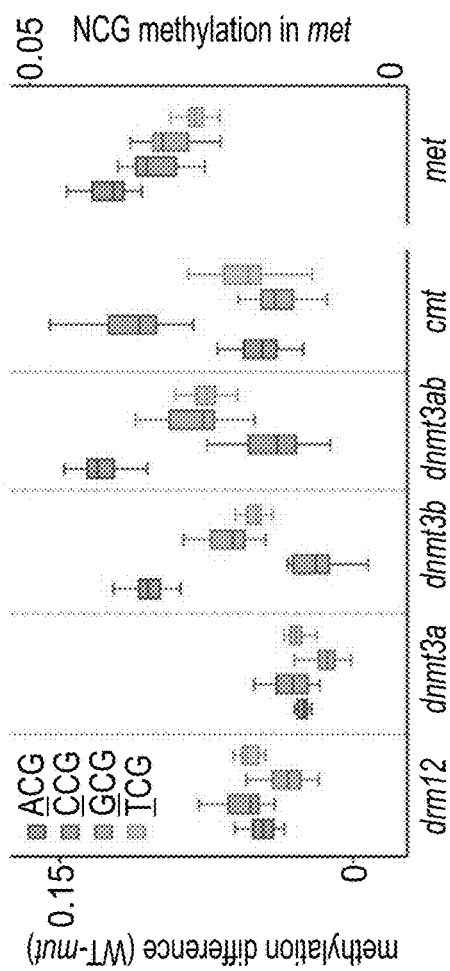
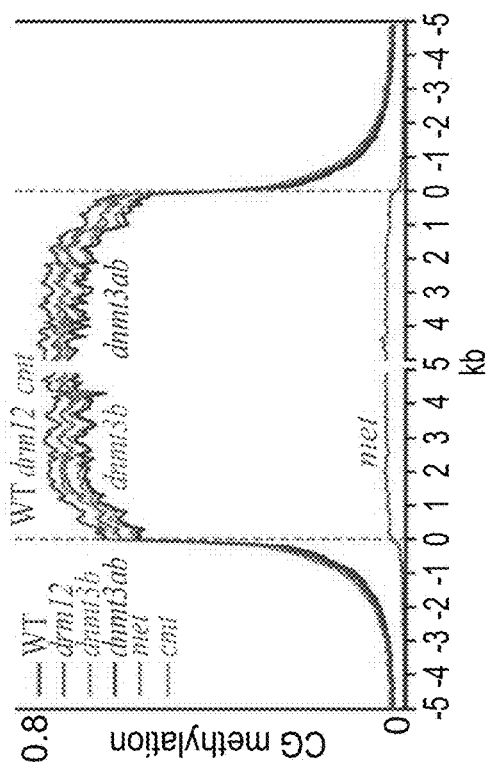
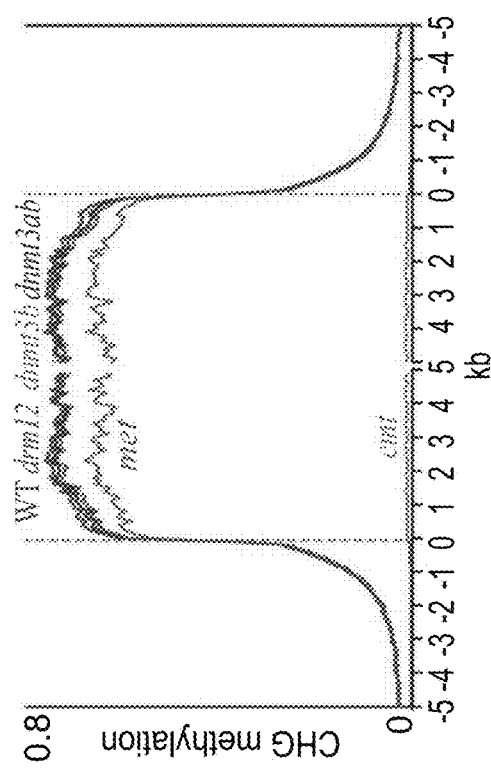
FIG. 2A, FIG. 2B, FIG. 2C, FIG. 2D, FIG. 2E

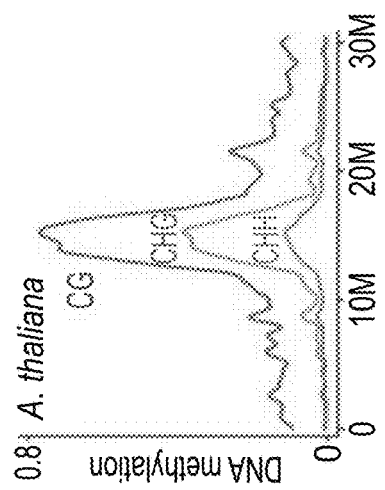
FIG. 4B
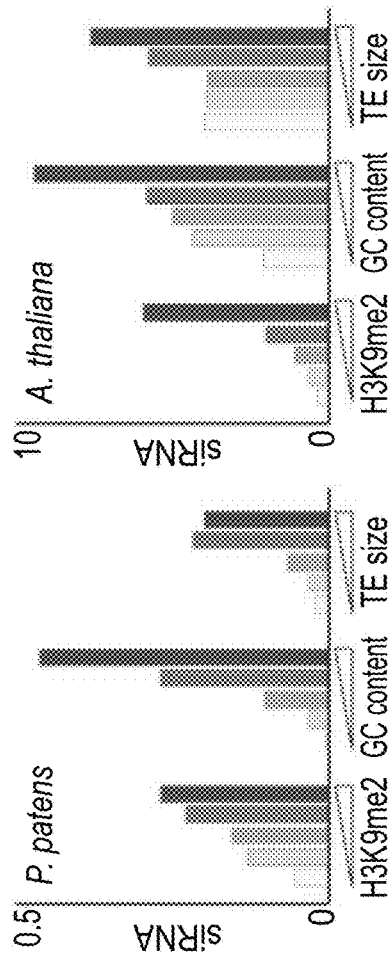
FIG. 4C
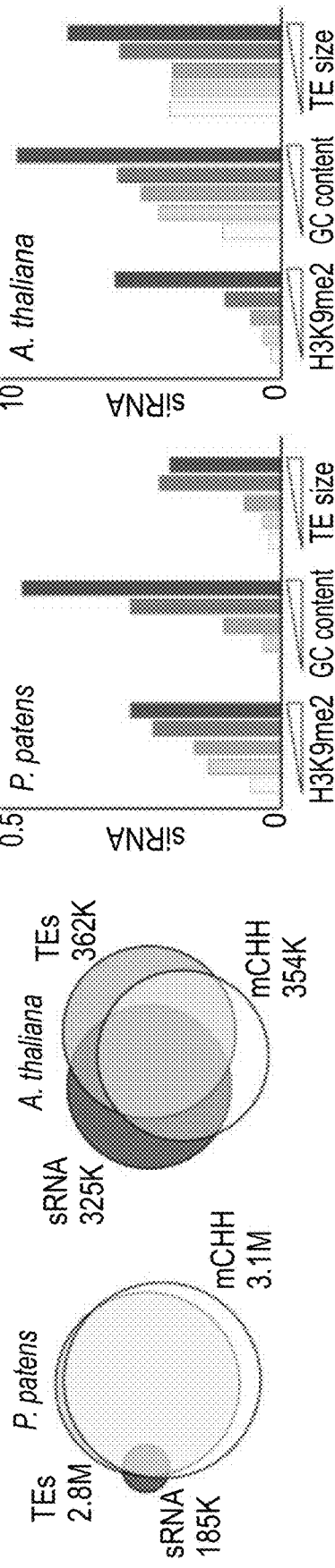
FIG. 4D
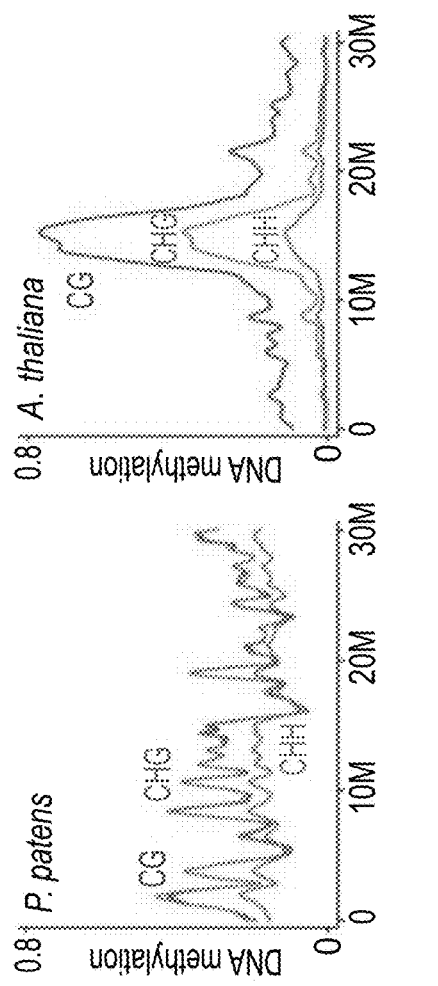
FIG. 4E
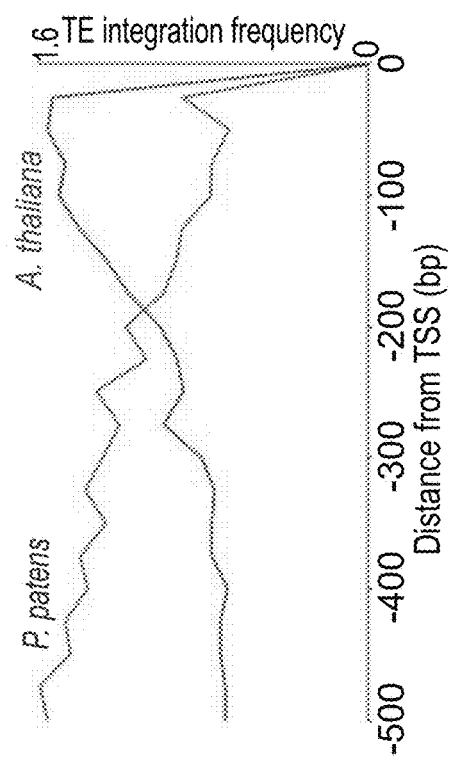

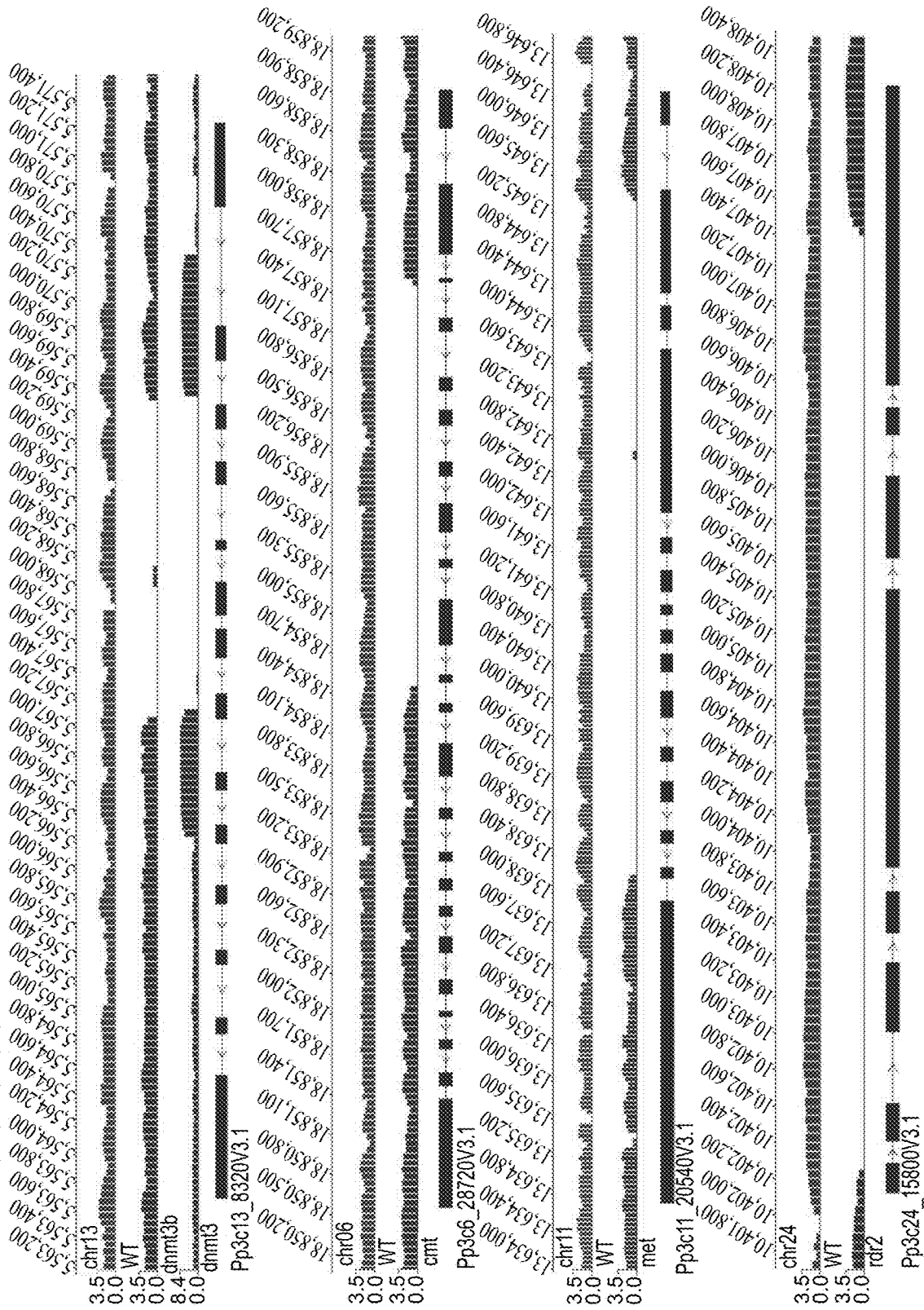

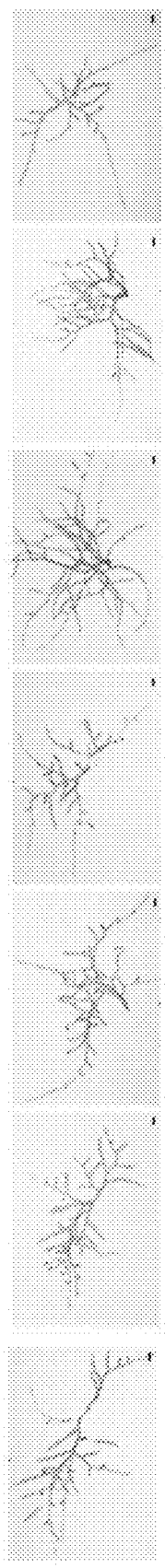
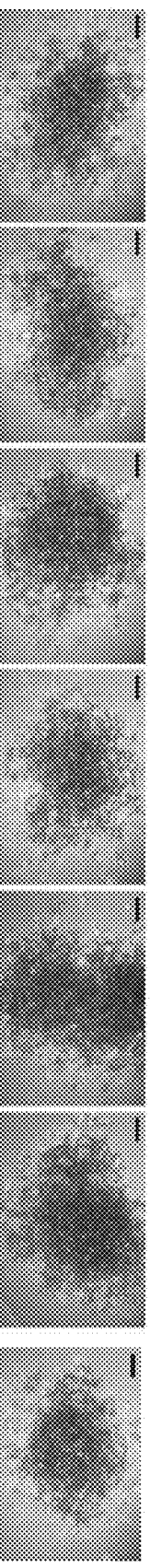
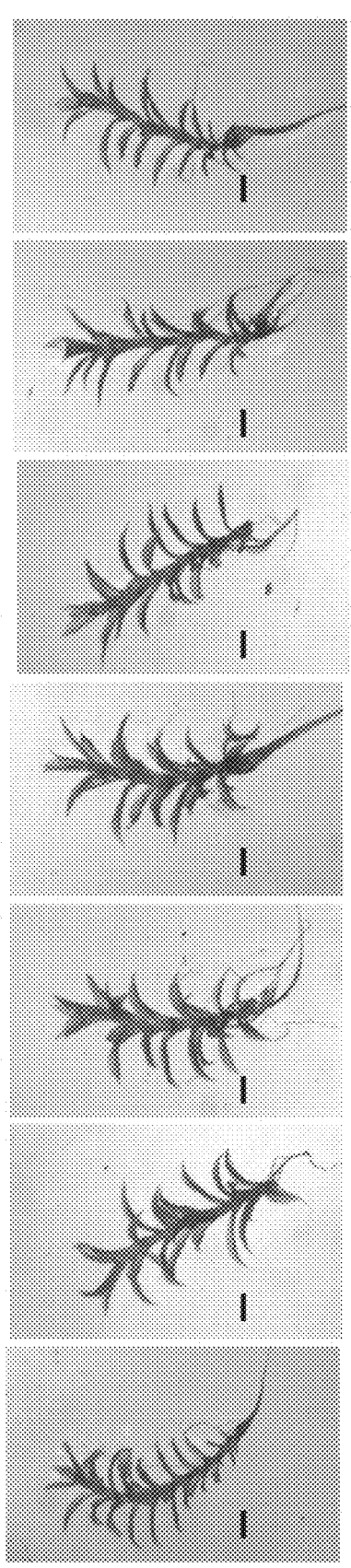
FIG. 7A Wild type
FIG. 7B drm1
FIG. 7C drm2
FIG. 7D drm12
FIG. 7E dnmt3a
FIG. 7F dnmt3b
FIG. 7G dnmt3ab
FIG. 7H
FIG. 7I
FIG. 7J
FIG. 7K
FIG. 7L
FIG. 7M
FIG. 7N
FIG. 7O
FIG. 7P
FIG. 7Q
FIG. 7R
FIG. 7S
FIG. 7T
FIG. 7U

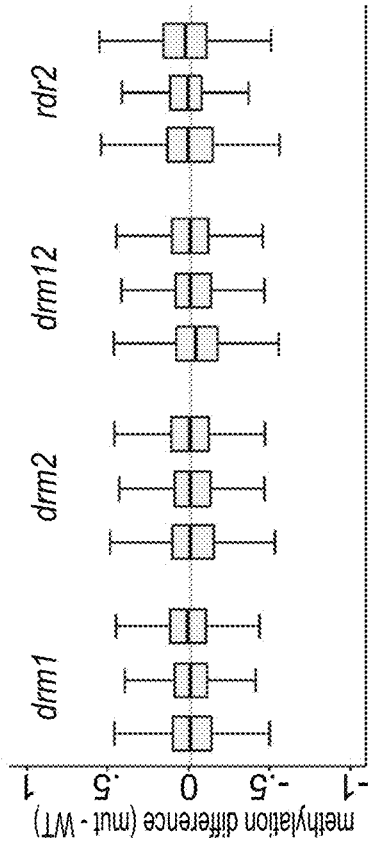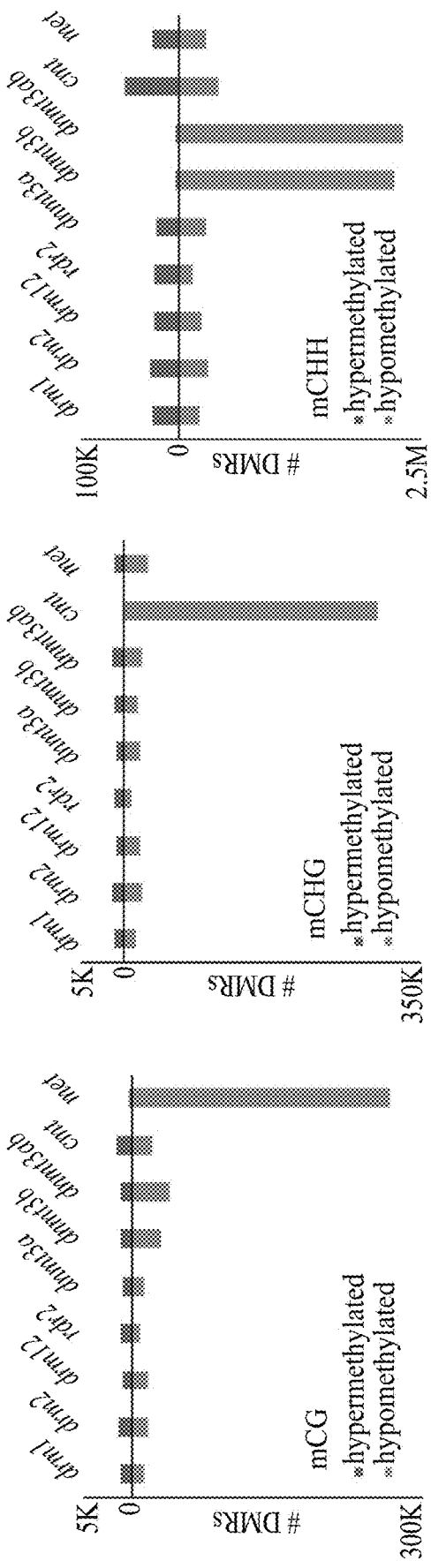

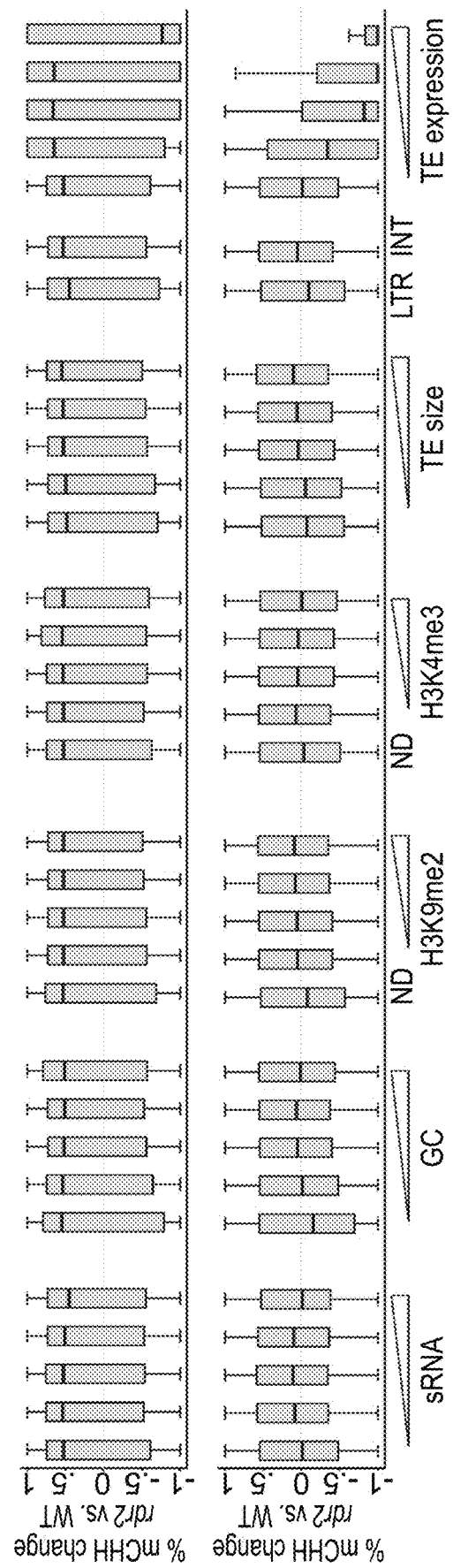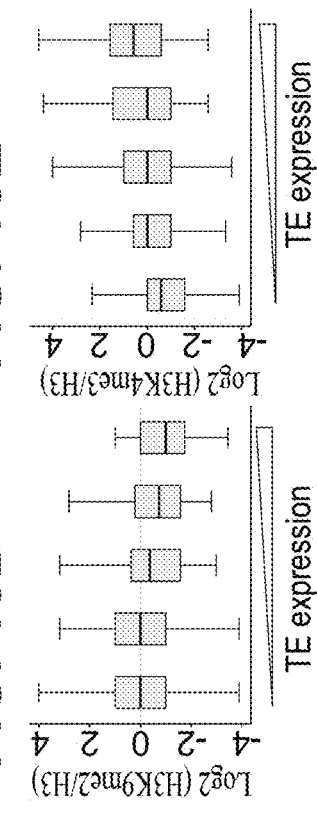

FIG. 16 atggactataaggaccacgacggagactacaaggatcatgatattgattacaaagacgatgacgataaga
tggcccccaaagaagaagcggaaggtcggtatccacggagtcccagcagcc gacaagaagtacagcatcg
gcctggccatcggcaccaactctgtgggctgggccgtgatcaccgacgagtacaaggtgcccagcaagaaa
ttcaaggtgctgggcaacaccgaccggcacagcatcaagaagaacctgatcggagccctgctgttcgacag
cggcgaaacagccgaggccacccggctgaagagaaccgccagaagaagatacaccagacggaagaacc
ggatctgctatctgcaagagatcttca gcaacgagatggccaaggtggacgacagcttcttccacagactgg
aagagtccttcctggtggaagaggataagaagcacgagcggcaccccatcttcggcaacatcgtggacga
ggtggcctaccacgagaagtaccccaccatctaccacctgagaaagaaactggtggacagcaccgacaag
gccgacctgcggctgatctatctggccctggcccacatgatcaagttccggggccacttcctgatcgaggg c
gacctgaaccccgacaacagcgacgtggacaagctgttcatccagctggtgcagacctacaaccagctgtt
cgaggaaaaccccatcaacgccagcggcgtggacgccaaggccatcctgtctgccagactgagcaagagc
agacggctggaaaatctgatcgcccagctgcccggcgagaagaagaatggcctgttcggcaacctgattgc
cctgagcctgggcctgacccccaacttcaagagcaacttcgac ctggccgaggatgccaaactgcagctga
gcaaggacacctacgacgacgacctggacaacctgctggcccagatcggcgaccagtacgccgacctgttt
ctggccgccaagaacctgtccgacgccatcctgctgagcgacatcctgagagtgaacaccgagatcaccaa
ggccccctgagcgcctctatgatcaagagatacgacgagcaccaccaggacctgaccctgctgaaagctc
tcgtgcggcagcagctgcctgagaagtacaaagagattttcttcgaccagagcaagaacggctacgccggc
tacattgacggcggagccagccaggaagagttctacaagttcatcaagcccatcctggaaaagatggacgg
caccgaggaactgctcgtgaagctgaacagagaggacctgctgcggaagcagcggaccttcgacaacggc
agcatcccccaccagatccacctgggagagctgcacgccattctgcggcggcaggaaga ttttacccattc
ctgaaggacaaccgggaaaagatcgagaagatcctgaccttccgcatcccctactacgtgggccctctggc
caggggaaacagcagattcgcctggatgaccagaaagagcgaggaaaccatcacccctggaacttcgag
gaagtggtggacaagggcgcttccgcccagagcttcatcgagcggatgaccaacttcgataagaacctgcc
caacgagaaggtgctgcccaagcacagcctg ctgtacgagtacttcaccgtgtataacgagctgaccaaag
tgaaatacgtgaccgagggaatgagaaagcccgccttcctgagcggcgagcagaaaaaggccatcgtgga
cctgctgttcaagaccaaccggaaagtgaccgtgaagcagctgaaagaggactacttcaagaaaatcgag
tgcttcgactccgtggaaatctccggcgtggaagatcggttcaacgcctccctgggcacataccacgatctgc
tgaaaattatcaaggacaaggacttcctggacaatgaggaaaacgaggacattctggaagatatcgtgctg
accctgacactgtttgaggacagagagatgatcgaggaacggctgaaaacctatgcccacctgttcgacga
caaagtgatgaagcagctgaagcggcggagatacaccggctggggcaggctgagccggaagctgatcaa

FIG. 16continued¹ cggcatccgggacaagcagtccggcaagacaatcctggatttcctgaa gtccgacggcttcgccaacagaa
acttcatgcagctgatccacgacgacagcctgaccttttaaagaggacatccagaaagcccaggtgtccggc
cagggcgatagcctgcacgagcacattgccaatctggccggcagccccgccattaagaagggcatcctgca
gacagtgaaggtggtggacgagctcgtgaaagtgatgggccggcacaagcccgagaacatcgtgatcgaa
atggccagagagaaccagacc acccagaagggacagaagaacagccgcgagagaatgaagcggatcga
agagggcatcaaagagctgggcagccagatcctgaaagaacaccccgtggaaaacacccagctgcagaa
cgagaagctgtacctgtactacctgcagaatgggcgggatatgtacgtggaccaggaactggacatcaacc
ggctgtccgactacgatgtggacgctatcgtgcctcagagctttctgaaggacgactccatcgacaaca agg
tgctgaccagaagcgacaagaaccggggcaagagcgacaacgtgcccccgaagaggtcgtgaagaaga
tgaagaactactggcggcagctgctgaacgccaagctgattacccagagaaagttcgacaatctgaccaag
gccgagagaggcggcctgagcgaactggataaggccggcttcatcaagagacagctggtggaaacccggc
agatcacaaagcacgtggcacagatcctggactcccggatgaa cactaagtacgacgagaatgacaagct
gatccgggaagtgaaagtgatcacccctgaagtccaagctggtgtccgatttccggaaggatttccagttttta
caaagtgcgcgagatcaacaactaccaccacgcccacgacgcctacctgaacgccgtcgtgggaaccgcc
ctgatcaaaaagtacccctaagctggaaagcgagttcgtgtacggcgactacaaggtgtacgacgtgcggaa
gatgatcgccaagagc gagcaggaaatcggcaaggctaccgccaagtacttcttctacagcaacatcatga
acttttttcaagaccgagattacccctggccaacggcgagatccggaagcggcctctgatcgagacaaacggc
gaaaccggggagatcgtgtgggataagggccgggattttgccaccgtgcggaaagtgctgagcatgcccca
agtgaatatcgtgaaaaagaccgaggtgcagacaggcggcttcagcaaagagtctatcc tgcccaagagg
aacagcgataagctgatcgccagaaagaaggactgggaccctaagaagtacggcggcttcgacagccccca
ccgtggcctattctgtgctggtggtggccaaagtggaaaagggcaagtccaagaaactgaagagtgtgaaa
gagctgctggggatcaccatcatggaaagaagcagcttcgagaagaatcccatcgactttctggaagccaa
gggctacaaagaagtgaaaaaggacctgatcat caagctgcctaagtactccctgttcgagctggaaaacg
gccggaagagaatgctggcctctgccggcgaactgcagaagggaaacgaactggccctgccctccaaata
tgtgaacttcctgtacctggccagccactatgagaagctgaagggctcccccgaggataatgagcagaaac
agctgtttgtggaacagcacaagcactacctggacgagatcatcgagcagatcagcgagttctccaagaga
gtgatcctggccgacgctaatctggacaaagtgctgtccgcctacaacaagcaccgggataagcccatcag
agagcaggccgagaatatcatccacctgtttacccctgaccaatctgggagcccctgccgccttcaagtacttt
gacaccaccatcgaccggaagaggtacaccagcaccaaagaggtgctggacgccacccctgatccaccaga
gcatcaccggcctgtacgagacacggatcgacctgtctcagctgggag gcgacaaaaggccggcggccac
gaaaaaggccggacaggccaaaaagaaaaagctcgagggcggaggcgggagcgGATCC GCAGAG
GCAGGCCCCTGGTCCGGAGAGCGCCTGGTGGTGCTGTCTCTGTTCGACGGCCTGG

FIG. 16continued2

GAGGCATCTGGCAGGCCCTGACCAAGCTGGGCATCCCTTTTTCTGGATACTCTAGC
GAGGTGCTGGCCCCAGCAATCCAGGTGGTGAAGAGCCGCCACCCTCGGGTGAAG
CACGTGGGCGACATCCGGAAGCTGAACCTGAGCGCCGTGCCAGAGAAGGTGGAC
CTGGTGGTGGGAGGATTCCCATGCCAGGATCTGTCCATCATGGGCAAGAAGGAG
GGCCTGCACGGCTCCCGGTCTAAGCTGTTCTTTGACCTGCTGAGAGTGCTGAAGG
TGTTCAAGCCTAAGTGGTTTCTGGTGGAGAATGTGGCCAGCATGTCCTGGGTGGA
CAGGGAGGAGATCACACGCCACCTGAAGGTGGCCCCAATGGAG CTGGATTCTCA
GGAGATCACCGCCAGCAAGCGGAGAAGGCTGTATTGGACAAACATCCCACACCC
ACCTAGACTGCCCCGCCTGCGGGATCACCCCAGCACCAGCCTCCAGTCCTGTCTGG
AGGGCGCCCTGGCCCTGGAGCAGAAGTGCGGCGTGATCCTGTGCAGCAATCTGT
ACAAGGGCTCTACCGCACGGCTGGAGCTGGTGCTGGACAACAAGACCAATAAGC
TGAGATATATCAAGCAGACAGAGGTGG AGGTGCTGATGGGCTACCCAAAGGATT
ATACCAACGTGGTGGCCCACGAGACAAAGGGCAGGACAGAGCAGGCCGAGAAG
GTGCTGAAAACCCCGTGCGCGCAAAGAGCGTGGAGCCTAAGCCATCCTCTGTGA
CACCACCCTCCGGCCGGcccgaattcggcagtggagagggcagaggaagtctgctaacatgcggtg
acgtcgaggagaatcctggccca atgaccgagtacaagcccacggtgcgcctcgc cacccgcgacgacgt
ccccagggccgtacgcaccctcgccgccgcgttcgccgactaccccgccacgcgccacaccgtcgatccgg
accgccacatcgagcgggtcaccgagctgcaagaactcttcctcacgcgcgtcgggctcgacatcggcaag
gtgtgggtcgcggacgacggcgccgcggtggcggtctggaccacgccggagagcgtcgaagcgggggcgg
tgttcgccgagatcggcccgcgcatggcc gagttgagcggttcccggctggccgcgcagcaacagatggaa
ggcctcctggcgccgcaccggcccaaggagcccgcgtggttcctggccaccgtcggcgtctcgcccgaccac
cagggcaagggtctgggcagcgccgtcgtgctccccggagtggaggcggccgagcgcgccggggtgcccg
ccttcctggagacctccgcgccccacaacctcccttctacgagcggctcggcttcaccgtcaccgccgacg t
cgaggtgcccgaaggaccgcgcacctggtgcatgacccgcaagcccggtgcctga

FIG. 17

MDYKDHDGDYKDHDIDYKDDDDKMAPKKKRKVGIHGVPAADKKYSIGLAIGTNSVG
WAVITDEYKVPSKKFKVLGNTDRHSIKKNLIGALLFDSGETAEATRLKRTARRRYTRRK
NRICYLQEIFSNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAP
LSASMIKRYDEHHQDLTLLKALVRQQLPEKYKEIFFDQSKNGYAGYIDGGASQEEFYKF
IKPILEKMDGTEELLVKLNREDLLRKQRTFDNGSIPHQIHLGELHAILRRQEDFYPFLKD
NREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLF
KTNRKVTVKQLKEDYFKKIECFDSVEISGVEDRFNASLGTYHDLLKIIKDKDFLDNEENE
DILEDIVLTLTLFEDREMIEERLKTYAHLFDDKVMKQLKRRRYTGWGRLS RKLINGIRDK
QSGKTILDFLKSDGFANRNFMQLIHDDSLTFKEDIQKAQVSGQGDSLHEHIANLAGSP
AIKKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDAIVPQSFL
KDDSIDNKVLTRSDKNRGKSDNVPSEEVVKKMKNYWRQLLNAKLITQRKFDNLTKAE
RGGLSELDKAGFIKRQLVETRQITKHVAQILDSRMNTKYDENDKLIREVKVITLKSKLVS
DFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFAT
VRKVLSMPQVNIVKKTEVQTGGFSKESILPKRNSDKLIARKKDWDPKKYGGFDSPTVA
YSVLVVAKVEKGKSKKLKSVKELLGITIMERSSFE KNPIDFLEAKGYKEVKKDLIIKLPKYS
LFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGDKRPAATKKAGQAK
KKKLEGGGGSGSAEAGPWSGERLVVLSLFDGLGGIWQALTKLGIPFSGYSSEVLAPAI
QVVKSRHPRVKHVGDIRKLNLSAVPEKVDLVVGGFPCQDLSIMGKKEGLHGSRSKLFF
DLLRVLKVFKPKWFLVENVASMSWVDREEITRHLKVAPMELDSQEITASKRRRLYWT
NIPHPPRLPRLRDHPSTSLQSCLEGALALEQKCGVILCSNLYKGSTARLELVLDNKTNKL
RYIKQTEVEVLMGYPKDYTNVVAHETKGRTEQAEKVLKTPVRAKSVEPKPSSVTPPS G
RPEFGSGEGRGSLLTCGDVEENPG

US 12,428,639 B2

PLANT DNA METHYLTRANSFERASES AND USES THEREOF

RELATED APPLICATIONS

This application is a National Phase of PCT Patent Application No. PCT/IL2020/050254 having International filing date of Mar. 4, 2020, which claims the benefit of priority under 35 USC § 119 (e) of U.S. Provisional Patent Application No. 62/813,805 filed on Mar. 5, 2019. The contents of the above applications are all incorporated by reference as if fully set forth herein in their entirety.

SEQUENCE LISTING STATEMENT

The ASCII file, entitled 88020Sequence-Listing.txt, created on Sep. 3, 2021, comprising 143,498 bytes, submitted concurrently with the filing of this application is incorporated herein by reference. The sequence listing submitted herewith is identical to the sequence listing forming part of the international application.

The project leading to this application has received funding from the European Research Council (ERC) under the European Union's Horizon 2020 Research and Innovation Programme (Grant Agreement No. 679551).

FIELD AND BACKGROUND OF THE INVENTION

The present invention, in some embodiments thereof, relates to plant DNA methyltransferases (DNMTs) and more particularly to plant DNMT3 uses thereof.

DNA methylation, the addition of a methyl group to a cytosine base, is a prominent epigenetic modification in many eukaryotes. It is catalyzed by distinct DNA methyltransferase (DNMT) families of proteins that share a conserved methyl-transferase domain (MTD). In plants, DNMTs evolved to methylate cytosines located in specific contexts (CG, CHG, and CHH; H=A, C, or T), distinct genetic elements (e.g. transposons and genes), various chromatin configurations (hetero- and eu-chromatin), as well as to establish methylation de novo at newly unmethylated sites or to maintain methylation upon DNA replication. Plants encode four types of DNMTs: Methyltransferase 1 (MET1), DNA methyltransferase 3 (DNMT3), chromomethylase (CMT), and domain rearranged methyltransferase (DRM). MET1s are homologs of mammalian DNMT1 and maintain CG methylation. CMTs are plant specific DNMTs first to appear in charophytes. Arabidopsis thaliana (Arabidopsis) CMT2 and CMT3 orthologs utilize their chromodomain (CD) to bind to histone H3 lysine 9 dimethylation (H3K9me2) heterochromatin and to methylate CHH and CHG sites, respectively. DNMT3s are ancient DNMTs that exist in animals, plants, and other eukaryotes[1,23]. Mammalian DNMT3s function primarily as de novo CG methylases and in specific tissues also at CH sites[1,6,24]. However, despite their significant role in mammals, non-animal DNMT3s have not been investigated thus far. DNMT3s were overlooked in plants probably due to their deficiency in angiosperms (flowering plants) and the discovery of their close homologs, DRMs, which function in de novo methylation. DRMs are plant specific DNMTs with a rearranged DNMT3-MTD. Angiosperm DRMs are a part of the RNA directed DNA methylation (RdDM) pathway that utilizes small RNA to establish de novo methylation within euchromatic transposons, that is enriched with active histone marks such as H3K4me3 and depleted of repressive marks as H3K9me2. So far, the function of plant DNMTs was comprehensively investigated in Arabidopsis thaliana and partially explored in a few additional angiosperms, all which lack DNMT3 in their genome.

SUMMARY OF THE INVENTION

According to an aspect of the present invention there is provided an isolated polynucleotide encoding a fusion protein which comprises a DNA targeting moiety linked to a catalytic domain of a plant DNA methyltransferase 3 (DNMT3) protein.

According to embodiments of the present invention, the DNA targeting moiety comprises a DNA endonuclease protein.

According to embodiments of the present invention, the DNA endonuclease protein is selected from the group consisting of Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 and Cpf1 endonuclease.

According to embodiments of the present invention, the DNA endonuclease protein comprises a catalytically inactive CRISPR associated 9 (dCas9) protein.

According to an aspect of the present invention there is provided an isolated polynucleotide encoding a catalytic domain of a plant DNA methyltransferase 3 (DNMT3) protein having a codon usage optimized for expression in an organism which is not a gymnosperm or a bryophyte.

According to embodiments of the present invention, the plant DNMT3 protein is a gymnosperm or a bryophyte DNMT3 protein.

According to embodiments of the present invention, the organism is a mammal.

According to embodiments of the present invention, the mammal is a human.

According to embodiments of the present invention, the organism is an angiosperm.

According to embodiments of the present invention, the DNMT3 protein is fused to a DNA targeting moiety.

According to embodiments of the present invention, the DNA targeting moiety comprises a DNA endonuclease protein.

According to embodiments of the present invention, the DNA endonuclease protein is selected from the group consisting of Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 and Cpf1 endonuclease.

According to embodiments of the present invention, the DNA endonuclease protein comprises a catalytically inactive CRISPR associated 9 (dCas9) protein.

According to embodiments of the present invention, the fusion protein comprises a single copy of said DNMT3 protein.

According to embodiments of the present invention, the catalytic domain of the DNMT3 protein comprises an amino acid sequence as least 70% similar or identical to at least one of the sequences as set forth in SEQ ID NOs: 1-11.

According to embodiments of the present invention, the catalytic domain of the DNMT3 protein comprises an amino acid sequence 100% similar or identical to at least one of the sequences as set forth in SEQ ID NO: 1-11.

According to embodiments of the present invention, the catalytic domain is linked directly to said DNA endonuclease protein.

According to embodiments of the present invention, the catalytic domain is linked to said endonuclease protein via a peptide linker.

According to embodiments of the present invention, the catalytically inactive Cas9 protein comprises mutations at a site selected from the group consisting of D10, E762, H983, D986, H840 and N863.

According to embodiments of the present invention, the mutations are: (i) D10A or D10N, and (ii) H840A, H840N, or H840Y.

According to embodiments of the present invention, the mutations are D10A and H840A.

According to embodiments of the present invention, the dCAS9 comprises the sequence as set forth in SEQ ID NO: 23.

According to embodiments of the present invention, the DNMT3 protein is linked to the C terminus of said endonuclease protein.

According to embodiments of the present invention, the DNMT3 protein is linked to the N terminus of said endonuclease protein.

According to embodiments of the present invention, the DNMT3 methylates a target DNA at a CHH site.

According to embodiments of the present invention, the DNMT3 additionally methylates a target DNA at a CpG site.

According to embodiments of the present invention, the DNMT3 methylates a target DNA at a CC site and/or a CT site to a greater extent than a human DNMT3 methylates the target DNA under identical conditions.

According to an aspect of the present invention there is provided a polypeptide comprising a DNA targeting moiety linked to a DNMT3 protein.

According to embodiments of the present invention, the DNA targeting moiety comprises a DNA endonuclease protein.

According to embodiments of the present invention, the DNA endonuclease protein is selected from the group consisting of Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 and Cpf1 endonuclease.

According to embodiments of the present invention, the DNA endonuclease protein comprises a catalytically inactive CRISPR associated 9 (dCas9) protein.

An expression vector comprising the polynucleotide described herein.

According to an aspect of the present invention there is provided an expression vector comprising a polynucleotide encoding a catalytic domain of a species of a plant DNA methyltransferase 3 (DNMT3) protein operatively linked to a transcriptional regulatory sequence which is not of said species.

According to embodiments of the present invention, the transcriptional regulatory sequence is not a gymnosperm transcriptional regulatory sequence or a bryophyte regulatory sequence.

According to embodiments of the present invention, the transcriptional regulatory sequence comprises a mammalian transcriptional regulatory sequence.

According to embodiments of the present invention, the transcriptional regulatory sequence comprises an angiosperm transcriptional regulatory sequence.

According to an aspect of the present invention there is provided a cell which expresses the polynucleotide described herein.

According to an aspect of the present invention there is provided a cell which comprises the expression vector described herein.

According to embodiments of the present invention, the cell is a mammalian cell.

According to embodiments of the present invention, the cell is a plant cell.

According to embodiments of the present invention, the plant cell is an angiosperm cell.

According to an aspect of the present invention there is provided a kit comprising the polynucleotide described herein and at least one guide RNA which is directed to a predetermined target gene.

According to an aspect of the present invention there is provided a method of increasing methylation of DNA in a cell, the method comprising expressing a polynucleotide encoding a catalytic domain of a plant DNA methyltransferase 3 (DNMT3) protein in the cell, thereby increasing methylation of DNA in the cell, wherein the cell is not of a gymnosperm plant.

According to an aspect of the present invention there is provided a method of increasing methylation of DNA in a cell, the method comprising expressing the polynucleotide described herein in the cell, thereby increasing methylation of DNA in the cell.

According to embodiments of the present invention, the method further comprises expressing one or more guide RNA directed to a target gene of the cell.

According to embodiments of the present invention, the cell is a mammalian cell.

According to embodiments of the present invention, the cell is a plant cell.

According to embodiments of the present invention, the cell is a diseased cell.

According to embodiments of the present invention, the mammalian cell is a human cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 1A:
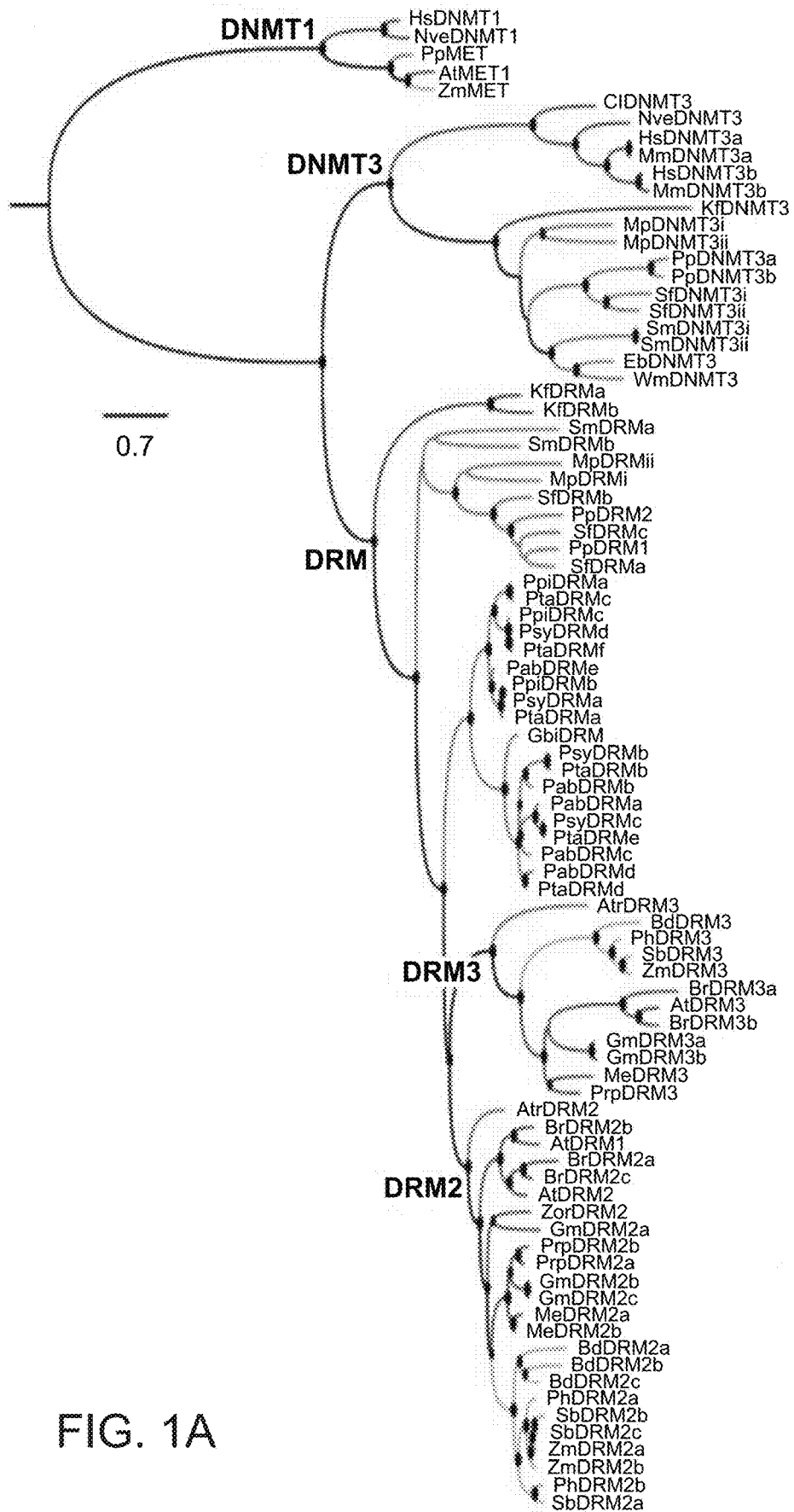
FIGS. 1A-C. PpDNMT3b and PpCMT establish DNA methylation and maintain the entire non-CG methylome.

A. Sequences of DNMT3 and DRM MTD regions were aligned using MUSCLE[71]. The phylogenetic tree was constructed by IQ-TREE[67-70] and illustrated by FigTree. DRM MTDs were reorganized to fit the linear motif order as in canonical DNMTs. DNMT1 homologs were added as an outgroup. Clades having bootstrap value above 70% are marked with a circle. Protein accessions are listed in Table 5. Colors depict taxonomic groups: red—animals; blue—charophytes; green—non-seed land plants; brown—gymnosperms; magenta—basal angiosperms; orange—monocots; purple—dicots.

B. Averaged genomic cytosine methylation of WT and DNMT mutants in three sequence contexts, CG, CHG, and CHH. See Table 7 for detailed information.

C. RPS methylation level in WT and indicated mutants. Red, yellow, and green represent CG, CHG, and CHH methylation, respectively.

FIGS. 2A-E. Genomic CG methylation regulation by PpCMT and PpDNMT3b.

A. Patterns of TE CG methylation in WT and indicated mutants. *P. patens* TEs were aligned at the 5' end and average methylation for all cytosines within each 100 bp interval is plotted. The dashed lines represent the points of alignment.

B. Box plot of NCG methylation difference in TEs between WT and indicated mutants (N=any nucleotide).

C. Box plot of the residual NCG methylation in TEs in met mutant.

D. Patterns of TE CHG methylation in WT and indicated mutants (similar to B).

E. Averaged genomic CHG methylation level in WT and DNMT mutants separated to CWG (i.e. CAG or CTG) and CCG.

FIGS. 3A-G. PpCMT and PpDNMT3 methylate heterochromatin.

A. Pearson correlation coefficients between CG/CHG/CHH methylation, GC content, and indicated histone modifications of TEs in 50 bp windows.

B. Box plots showing GC content, H3K9me2, and H3K4me3 levels in 50 bp windows within five quantile TE sizes.

C. Box plots of averaged DNA methylation in 50 bp windows of WT protonoma over five quantiles of TE sizes.

D. Box plots of percent-methylation-change between WT and indicated mutants 50 bp windows with a minimum 10% methylation in either of the samples, over TE size.

E. Patterns of TE CHH methylation in WT and indicated mutants as described in FIG. 2A.

F. Box plots showing the distribution of percent-methylation-change per 50 bp windows between WT and cmt mutant over H3K9me2, GC content, and TE size quantiles.

G. CHH methylation level (red WT, blue mutant) CHH methylation difference (cmt minus WT), H3K9me2, and gene/TE annotations of a representative region. Genes and TEs oriented 5' to 3' and 3' to 5' are shown above and below the line, respectively. Open black box marks a cmt hypomethylated region enriched for H3K9me2.

FIGS. 4A-E. PpDRMs methylate active-euchromatic TEs.

A. Box plots of percent-methylation-change between indicated samples within differentially CHH methylated 50 bp windows, separated based on the level of various genomic/chromatin attributes. Note the hypo-methylation trend in protonema drm12 sample (top track) in genomic regions with high siRNA counts, low GC content, absent H3K9me2 signal, high H3K4me3 signal, short TEs, LTR annotations, and TE expression. B. Venn diagram showing abundance and overlap between siRNA, CHH methylation, and TE annotation, in *Arabidopsis* and *P. patens*. C. siRNA abundance over increased quantiles of indicated chromatin features in *A. thaliana* (c) and *P. patens* (c). D. Patterns of TE integration in *Arabidopsis* and *P. patens* upstream to gene TSS. *Arabidopsis* or *P. patens* genes were aligned at the 5' end (0 at x axis) and percentage of the number of TEs (first and closest nucleotide of TE to TSS) within each 25 bp is plotted. E. LOWESS fit of DNA methylation distribution averaged in 100 kb bins across chromosome 1 in *Arabidopsis* and *P. patens*.

Figure 5A:
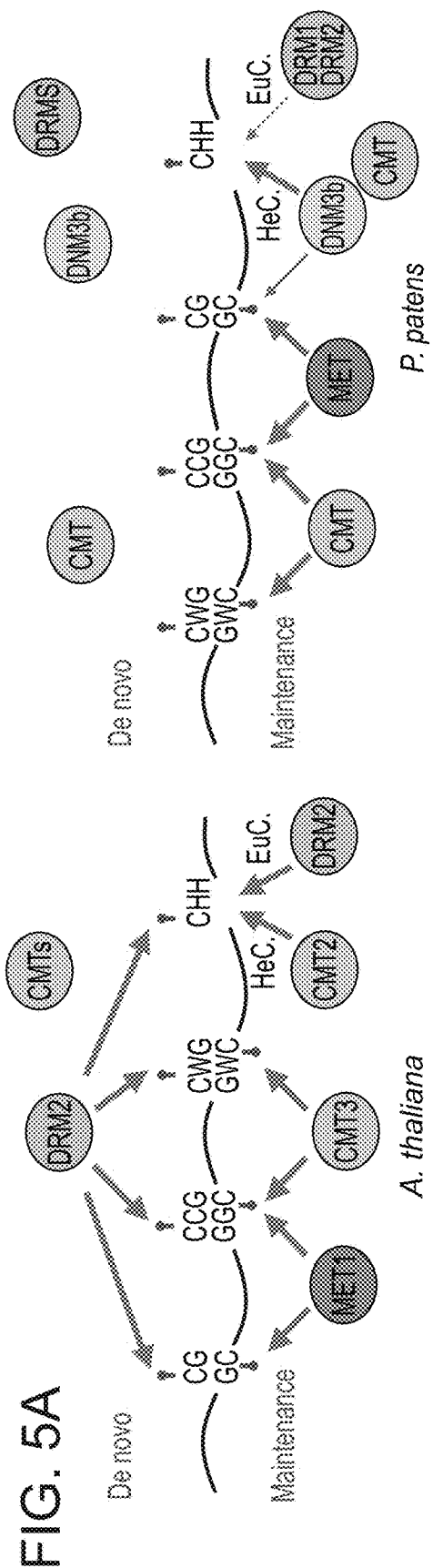
Figure 5B:
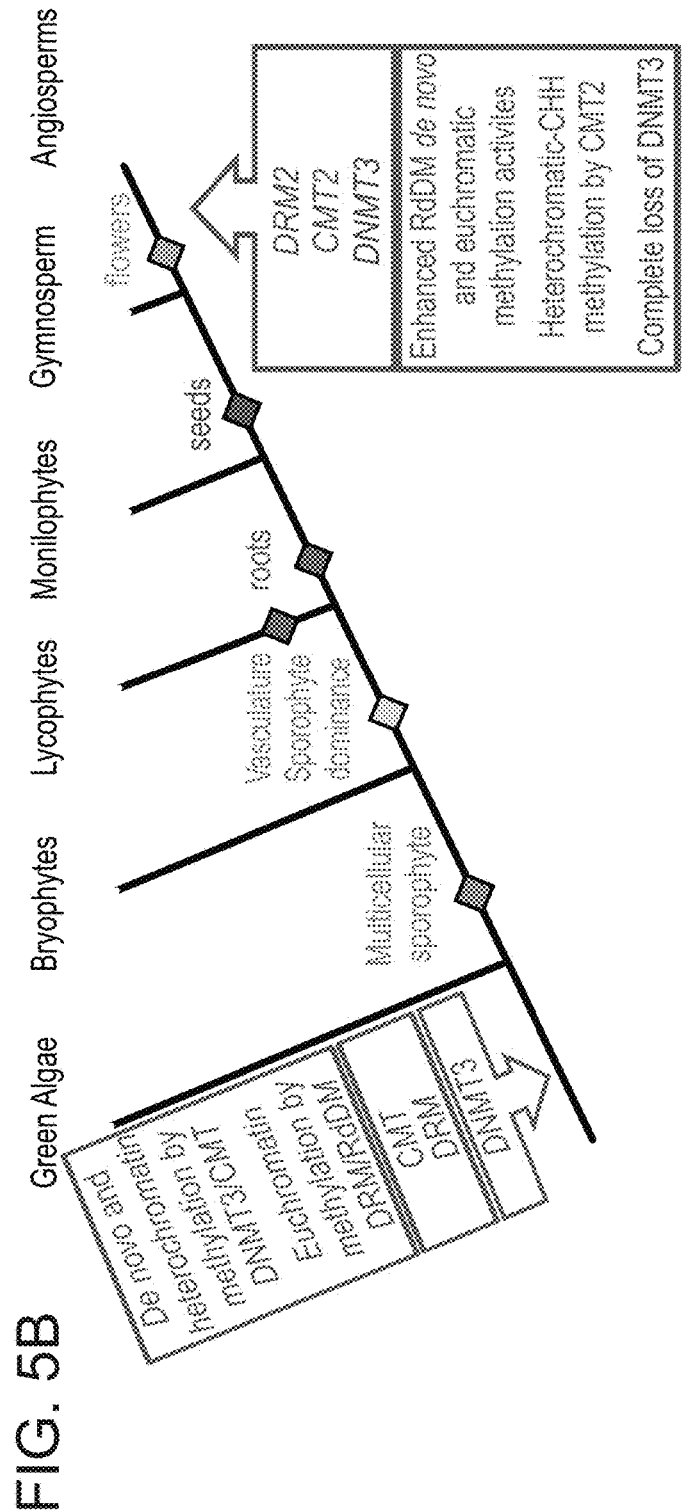

FIGS. 5A-B. Mechanisms and evolution of plant DNMTs.

A. DNMT methylation mechanisms are illustrated based on current knowledge. Black line represents the DNA with different cytosine subcontexts embedded in it. Lollipops represent methylation. Arrows width are corresponding qualitatively to the relative level of methylation mediated by indicated DNMTs. HeC.—heterochromatin, EuC.—euchromatin. De novo and maintenance methylation activities are shown above and below the DNA, respectively.

B. Schematic illustration of the evolution of plant DNMTs and their function based on previous and the present studies.

Figure 6:
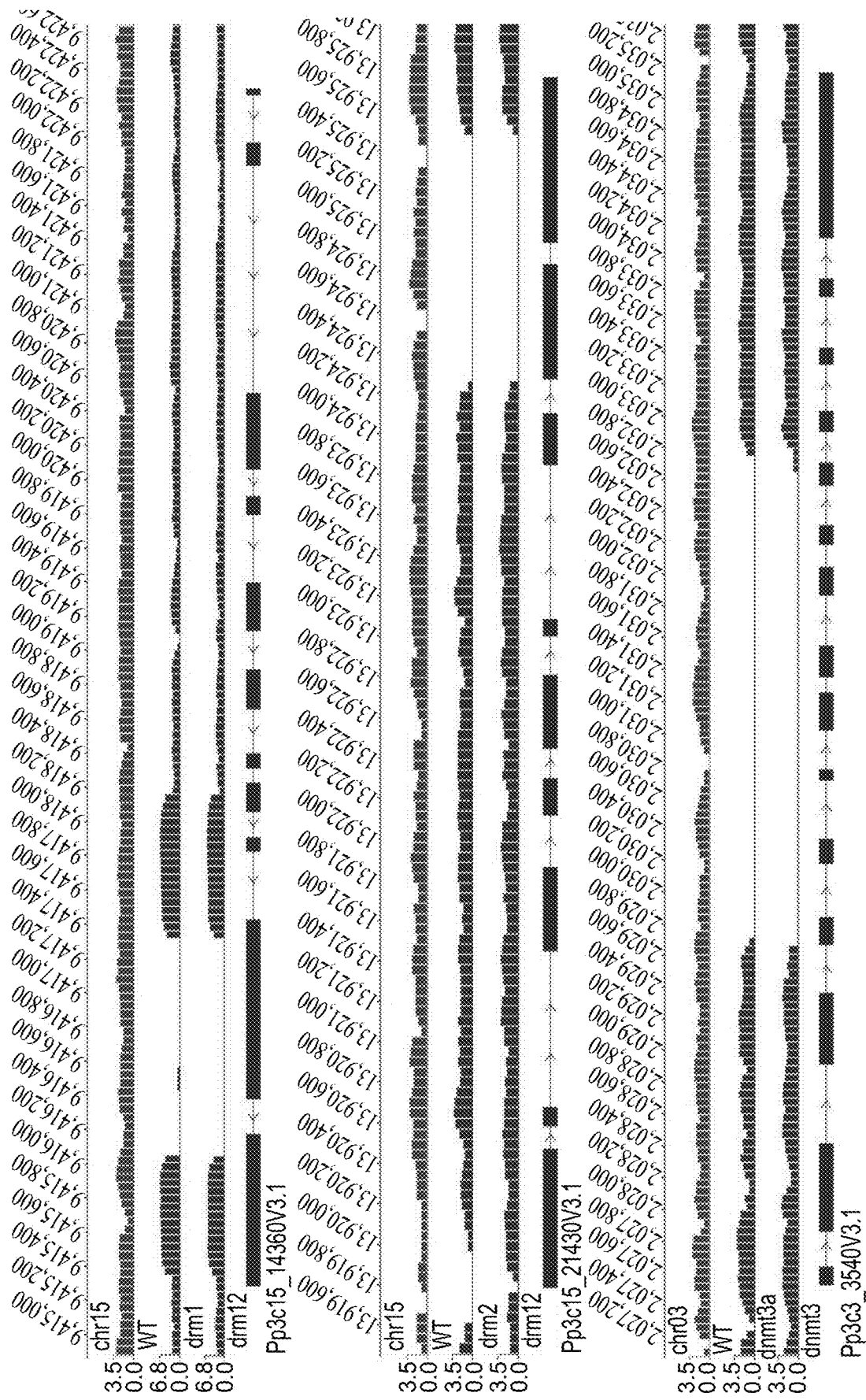

FIG. 6. Genotyping of PpDNMT mutants. BS-seq reads coverage of PpDNMT genes in WT and dnmt mutants.

FIGS. 7A-U. Mutagenesis of PpDNMT3 and PpDRM does not disrupt *P. patens* development. Morphological analysis of protonema and gametophore development in WT and PpDNMT3 and DRM deletion mutants. a-g, Seven days old protonemata of WT (A) and mutants (B-G). Scale bar: 50 µm. H-N, Three weeks old plants bearing gametophores of WT (H) and mutants (I-N). Scale bar: 250 µm. O-U, Six weeks old gamethopores of WT (O) and mutants (P-U). Scale bar: 1 mm.

Figure 8:
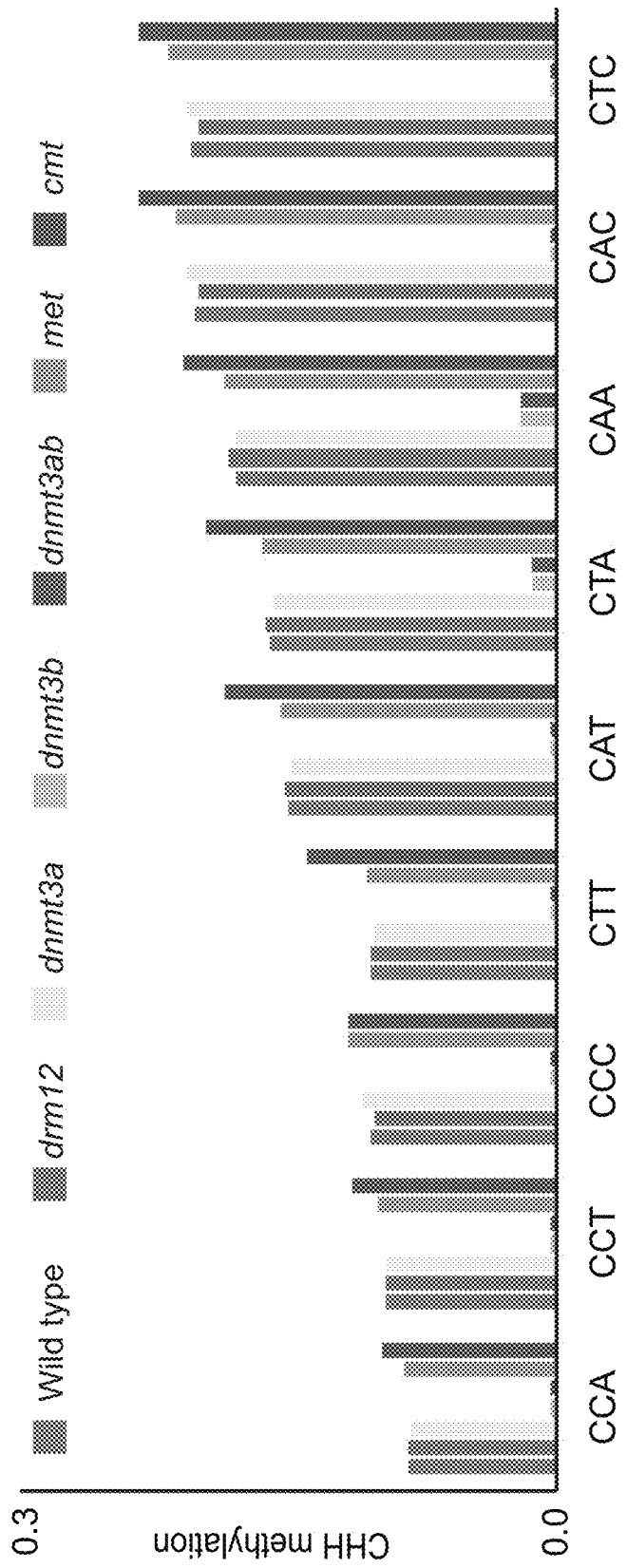

FIG. 8. Preferences in CHH methylation subcontexts. Averaged genomic CHH methylation level, in wild type and DNMT mutants, separated to its subcontexts.

Figure 9:
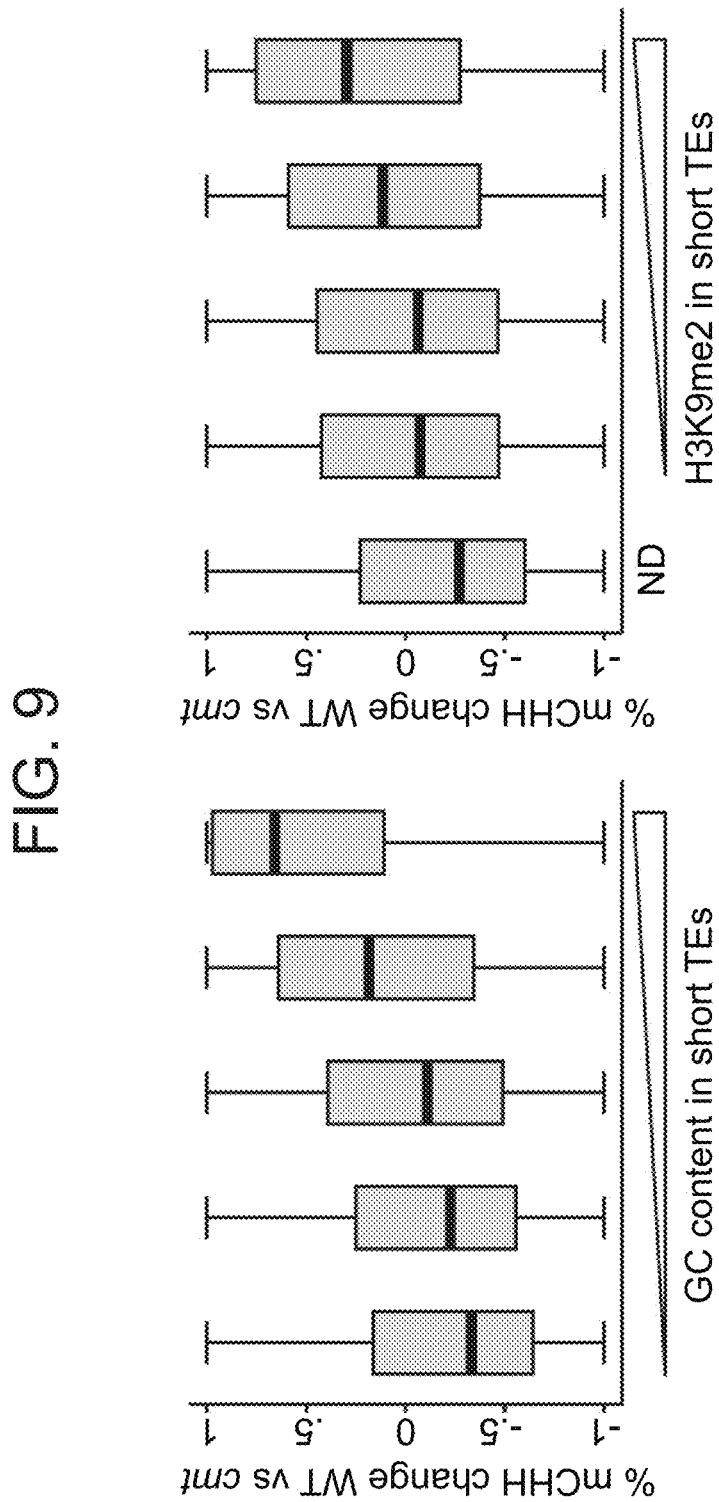

FIG. 9. Regulation of CHH methylation by PpCMT. Box plots showing the distribution of percent-methylation-change per 50 bp windows between wild type and cmt mutant over H3K9me2, GC content within TEs shorter than 500 bp long.

FIGS. 10A-E. DNA methylation in drm and rdr2 mutants. A. DNA methylation difference between WT and indicated mutants. B. Number of hypo- and hyper-methylated CG, CHG, and CHH DMRs in each of the mutants. C-D. Percent-methylation-change between WT and rdr2 mutant within rdr2-CHH-DMRs (C) or drm12-CHH-DMRs (D) over five centiles of indicated genomic or chromatin attributes. The WT plant is genetically unrelated to the rdr2 one, thus comparison between these two plants could contribute to a noise level that could mask a weak hypo-methylation signal. Therefore, the CHH methylation change in rdr2 was analyzed within drm12-CHH-DMRs (d). Note the change from global hypermethylation in rdr2 in (C) to a slight hypo-methylation at low GC regions, short TEs, LTRs, and expressed TEs in (D).

Figure 11:
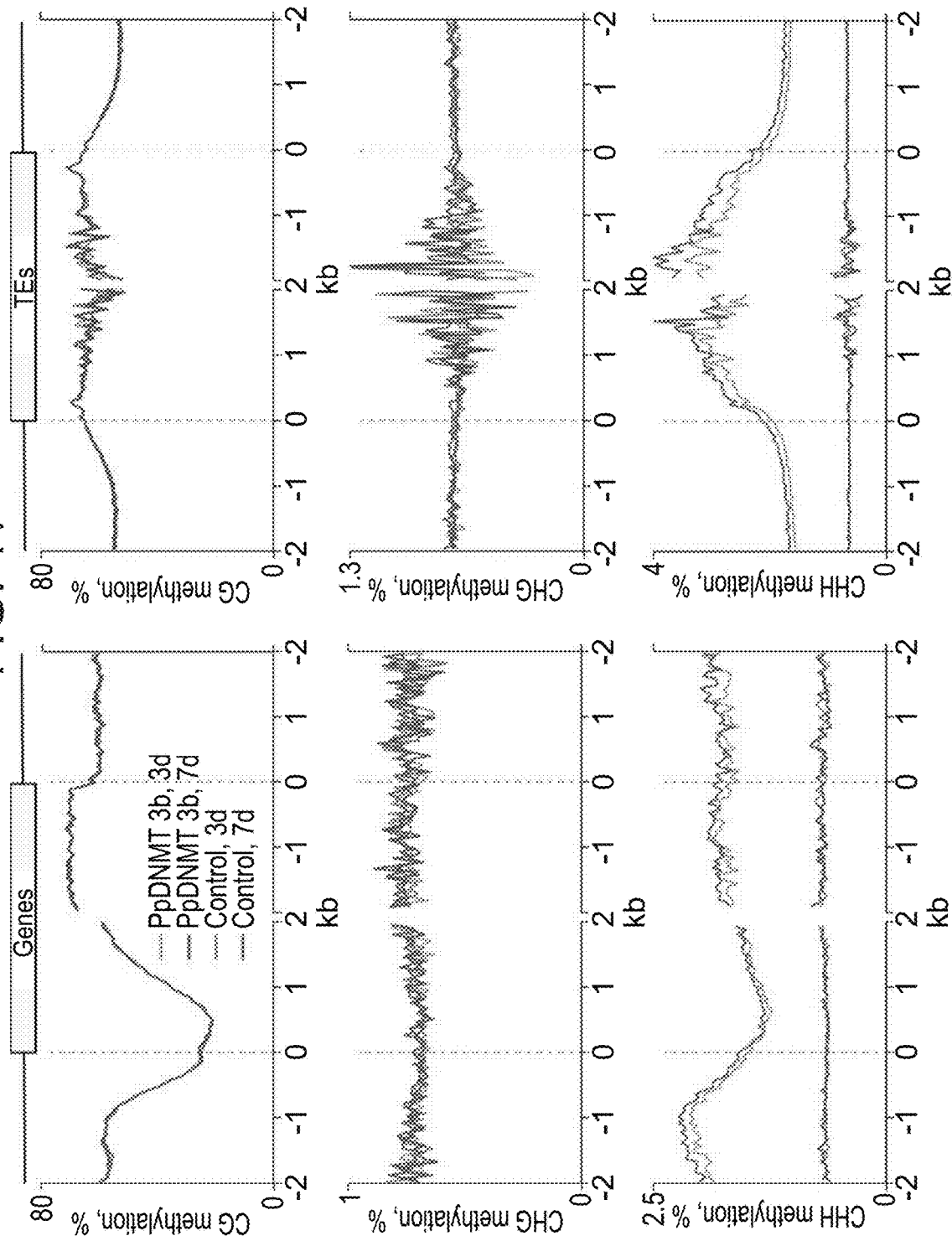

FIG. 11. Global patterns of CG, CHG and CHH methylation (H=A, C, or T) in genes and transposons (TEs) in HEK293 cells expressing PpDNMT3b-GFP or GFP (control). DNA methylation was profiled in 84 Mega bases in the human genome using SureSelectXT Human Methyl-Seq Target Enrichment Panel (Agilent) and Illumina high throughput sequencing. Genes and TEs were aligned at either the 5' or 3' end and average methylation for all cytosines within each 50 bp interval was plotted. The dashed lines represent the points of alignment. These graphs show a specific CHH hypermethylation in cells transfected with PpDNMT3b.

Figure 12:
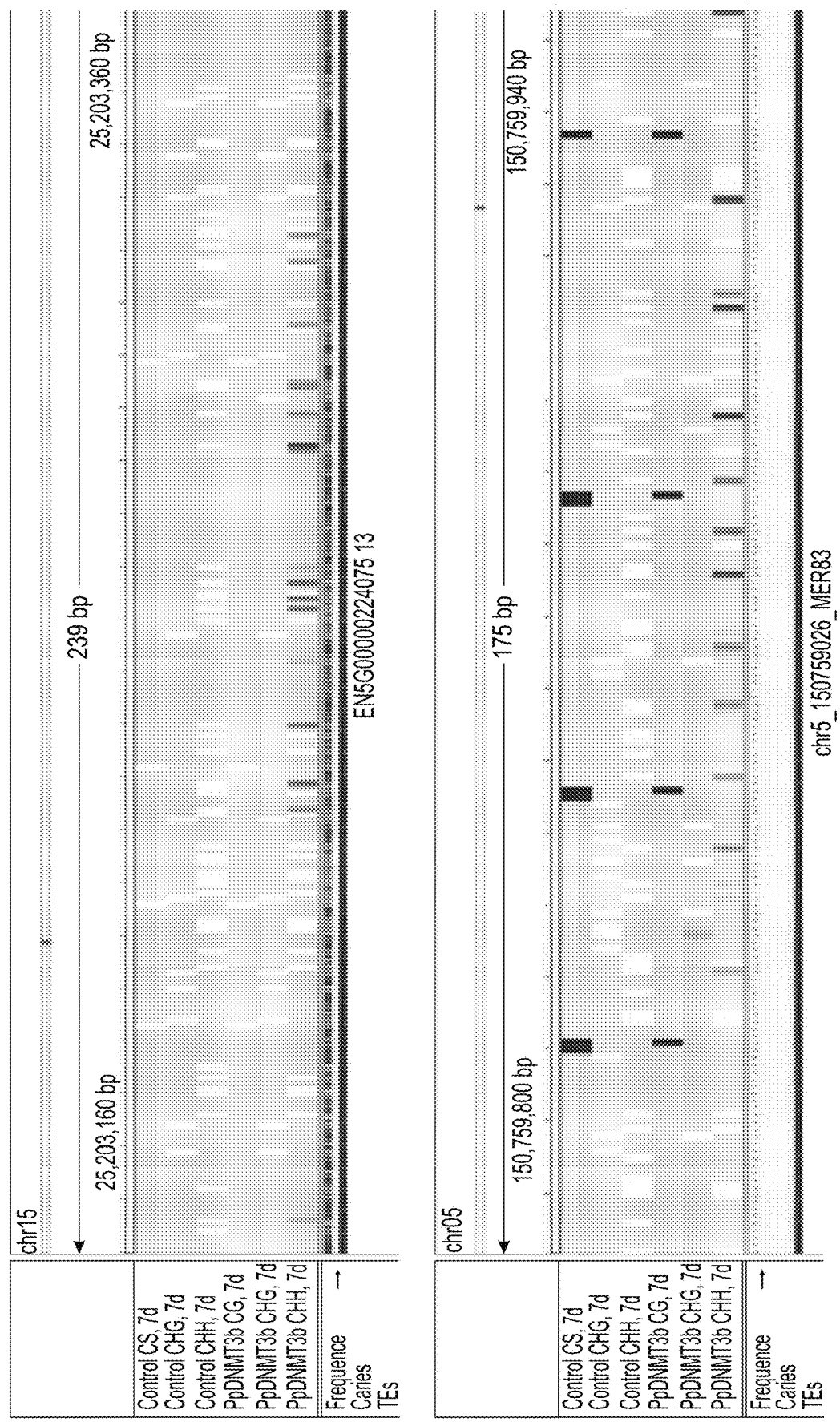

FIG. 12. Localized patterns of CG, CHG and CHH methylation in a particular gene and transposon in HEK293 cells expressing PpDNMT3b-GFP or GFP (control). A snapshot of methylation patterns in a representative gene (top panel) and a TE (bottom panel) regions is presented. Tracks order from the top to the bottom is as following. The three top tracks display CG, CHG and CHH methylation levels of control sample, the three bottom tracks display the corresponding PpDNMT3b methylation. CG, CHG and CHH methylation levels are represented as color scale of blue, green and red, respectively (white bar means zero methylation). These graphs show a specific CHH hypermethylation (red bars) in PpDNMT3b transfected cells, either in a region depleted of methylated CGs (top panel) or containing methylated CGs (bottom panel).

Figure 13:
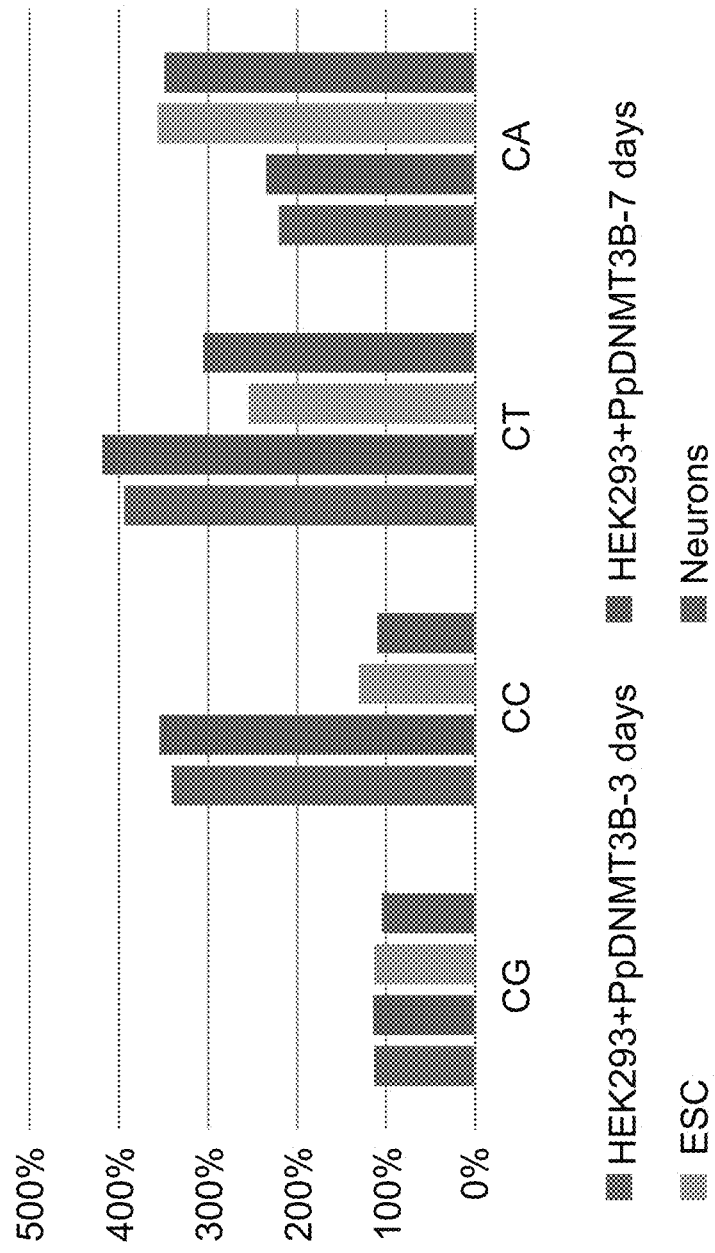

FIG. 13. Comparison of methylation levels between HEK293 cells expressing PpDNMT3b and two other human cell types with heightened non-CG methylation. DNA methylation was profiled for 84 Mega bases of the human genome using SureSelectXT Human Methyl-Seq Target Enrichment kit (Agilent) and Illumina high throughput sequencing. This figure shows global average methylation levels separated to CG/CC/CT/CA sequence context groups normalized with fetal tissue (having low non-CG methylation as most human tissues/cell-types and specifically HEK293 cells) for HEK293 cells expressing PpDNMT3b, 3 or 7 days following transfection as well as human tissues having significant non-CG methylation levels: neurons from adult and embryonic stem cells (ESC). PpDNMT3b expression in human HEK293 cells resulted in non-CG hypermethylation genome wide.

Figure 14:
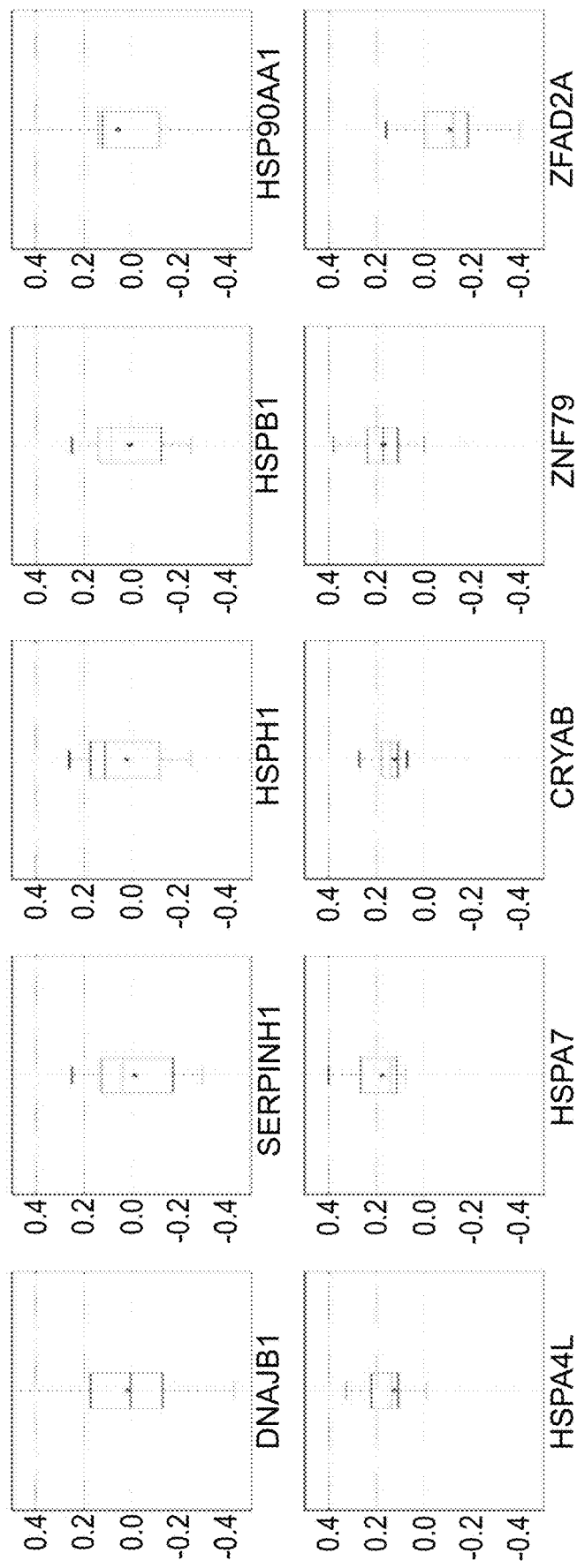

FIG. 14. Several PpDNMT3b upregulated genes in HEK293 cells show increase in non-CG methylation. For each gene, the difference in methylation between sites having at least 10% methylation in either PpDNMT3b or control lines is plotted in boxplots.

Figure 15:
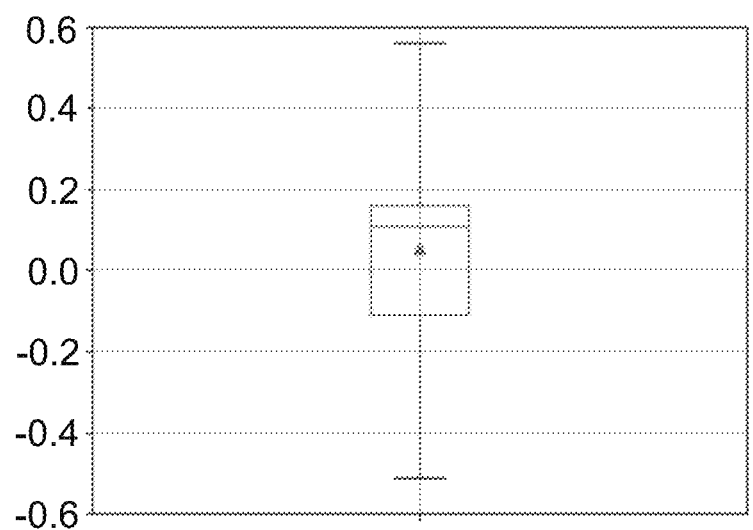

FIG. 15. Expression of PpDNMT3b in *Arabidopsis* induces CHH methylation. BS-seq data of an *Arabidopsis* plant expressing PpDNMT3b in the background of ddcc (drm1 drm2 cmt2 cmt3 quadruple mutant which has trivial non-CG methylation levels) was analyzed with methylpy. The difference in methylation genome wide between sites having at least 10% methylation in either PpDNMT3b/ddcc or control (ddcc) lines is plotted in boxplots.

FIG. 16 is the DNA sequence of FLAG-NLS-dcas9-NLS-PpDNMT3b_MTD-T2A-PuroR (SEQ ID NO: 64). PpDNMT3b methyltransferase domain (MTD) (marked in red within the DNA sequence was expressed in fusion with dcas9 (marked in blue) along with FLAG-tag, protein nuclear localization sequences (NLS) and poly-Gly linkers separating dcas9, NLS and PpDNMT3b-MTD. Additionally, this open reading frame continues following the PpDNMT3b-MTD sequence with a T2A protein separation sequence (marked in green) to allow expression of Puromycin resistance gene (One reading frame allowing expression of dcas9-PpDNMT3b-MTD and PuroR as separate proteins).

FIG. 17 is the protein sequence of FLAG-NLS-dcas9-NLS-PpDNMT3b_MTD-T2A-PuroR (SEQ ID NO: 65). PpDNMT3b methyltransferase domain (MTD) (marked in red within the amino acid sequence was expressed in fusion with dcas9 (marked in blue) along with FLAG-tag, protein nuclear localization sequences (NLS) and poly-Gly linkers separating dcas9, NLS and PpDNMT3b-MTD.

DESCRIPTION OF SPECIFIC EMBODIMENTS OF THE INVENTION

The present invention, in some embodiments thereof, relates to plant DNA methyltransferases (DNMTs) and more particularly to plant DNMT3 uses thereof. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

To properly regulate the genome, cytosine methylation is established by animal DNA methyltransferase 3s (DNMT3s). While altered DNMT3 homologs, Domains rearranged methyltransferases (DRMs), have been shown to establish methylation via the RNA directed DNA methylation (RdDM) pathway, the role of true-plant DNMT3 orthologs have so far remained elusive.

Figure 1B:
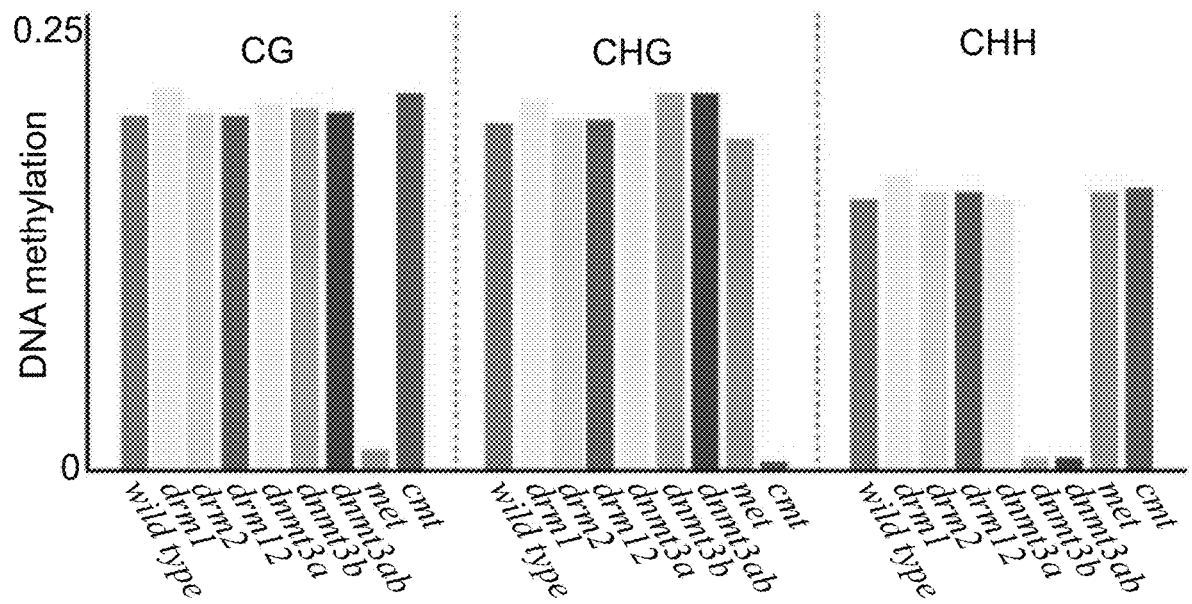

The present inventors have now profiled de novo (RPS transgene) and genomic methylation in the basal plant, *Physcomitrella patens*, mutated in each of its PpDNMTs. The present inventors have shown that PpDNMT3b mediates CG and CHH de novo methylation, independently of PpDRMs (FIG. 1B).

Whilst further reducing the present invention to practice, the present inventors have shown that the novel plant derived DNMT3 has a methyltransferase activity when expressed in mammalian cells (see FIGS. 11-14). The expressed DNMT3 had a higher preference to methylate CC or CT sites than human DNMT3s under identical conditions. As a result of the methyltransferase activity, the present inventors showed that expression of numerous genes was upregulated (see Table 8).

In addition, the present inventors expressed the novel plant DNMT3 in a heterologous plant system (*Arabidopsis*) and showed that it carried out CHH methylation (FIG. 15). According to a first aspect of the present invention there is provided an isolated polynucleotide encoding a catalytic domain of a plant DNA methyltransferase 3 (DNMT3) protein.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

Thus, some embodiments of the invention encompasses nucleic acid sequences described herein; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The term "isolated" refers to at least partially separated from its natural environment.

The polynucleotide sequence may be a DNA or RNA sequence encoding a catalytic domain of a plant DNA methyltransferase (DNMT) protein, capable of methylating target DNA at a CHH site.

The DNA methyltransferase may be derived from any plant.

In one embodiment, the DNA methyltransferase is derived from a monocotyledonous plant.

Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales.

Plants belonging to the class of the Gymnospermae are Cycadales, Conifers, Ginkgoales, Gnetales, and Pinales.

In another embodiment, the DNA methyltransferase is derived from a gymnosperm including but not limited to *Encephalartos barteri, Stangeria eriopus, Welwitschia mirabilis, Welwitschia mirabilis, Pinus taeda, Pinus sylvestris, Manoao colensoi, Sundacarpus amarus* and *Pinus jeffreyi.*

In another embodiment, the DNA methyltransferase is derived from a bryophytes (e.g. a moss or a liverworts), specific examples of such including but not limited to Marchantia *polymorpha, Physcomitrella patens* and Sphagnum *fallax.*

In particular, the DNA methyltransferase is derived from *Physcomitrella patens.*

In still another embodiment, the DNA methyltransferase is derived from a Charophytes, including for example Klebsormidium flaccidum.

In yet another embodiment, the DNA methyltransferase is derived from a lycophytes including for example Selaginella moellendorffii.

In another embodiment, the DNA methyltransferase is derived from a dicotyledonous plant. Such plants include those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates.

In one embodiment, the plant DNA methyltransferase protein is DNMT3. The plant DNA methyltransferase is capable of methylating target DNA at a CG site as well as at a CHH site.

In one embodiment, the plant DNMT3 methylates a target DNA at a CC site and/or a CT site to a greater extent than a human DNMT3 methylates the target DNA under identical experimental conditions.

The plant DNA methyltransferase of this aspect of the present invention is not a DRM and does not require siRNA to bring about methylation.

The phrase "catalytic domain" as used herein refers to part of the DNMT3 protein (i.e., a polypeptide) which exhibits functional properties of the enzyme such as methylating target DNA (the functional domain). According to preferred embodiments of the invention the catalytic domain of a plant DNMT3 is a polypeptide sequence which comprises a sequence at least 70%, 75%, 80%, 85%, 90%, 91%, 92%, 93%, 94%, 95%, 96%, 97%, 98%, 99% or 100% identical (or similar) to one of the sequences set forth in SEQ ID NOs: 1-11.

According to a particular embodiment, the catalytic domain of a plant DNMT3 is a polypeptide sequence which comprises a sequence at least 70%, 75%, 80%, 85%, 90%, 91%, 92%, 93%, 94%, 95%, 96%, 97%, 98%, 99% or 100% identical (or similar) to one of the sequences set forth in SEQ ID NOs: 5 or 6, as determined using the BestFit software of the Wisconsin sequence analysis package, utilizing the Smith and Waterman algorithm, where gap weight equals 50, length weight equals 3, average match equals 10 and average mismatch equals −9.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

The isolated polynucleotide of this aspect of the present invention may encode the full length DNMT3 (i.e. the catalytic domain and the regulatory domain). Thus, the isolated polynucleotide may encode proteins comprising amino acid sequences which are at least 50%, at least 55%, at least 60%, at least 65% at least 70% at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of SEQ ID NOs: 12-22, or at least 70% at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of SEQ ID NOs: 1-11, as determined using the BestFit software of the Wisconsin sequence analysis package, utilizing the Smith and Waterman algorithm, where gap weight equals 50, length weight equals 3, average match equals 10 and average mismatch equals −9.

According to a particular embodiment, the plant DNMT3 is a polypeptide sequence which comprises a sequence at least 70%, 75%, 80%, 85%, 90%, 91%, 92%, 93%, 94%, 95%, 96%, 97%, 98%, 99% or 100% identical (or similar) to SEQ ID NO: 16.

To express the plant derived DNMT3 in a heterologous system, the codon usage of the nucleic acid sequence which encodes the DNMT3 may be optimized.

Nucleic acid sequences encoding the enzymes of some embodiments of the invention may be optimized for expression in a particular system. Examples of such sequence modifications include, but are not limited to, an altered G/C content to more closely approach that typically found in the species of interest, and the removal of codons atypically found in the species commonly referred to as codon optimization.

The phrase "codon optimization" refers to the selection of appropriate DNA nucleotides for use within a structural gene or fragment thereof that approaches codon usage within the species of interest. Therefore, an optimized gene or nucleic acid sequence refers to a gene in which the nucleotide sequence of a native or naturally occurring gene has been modified in order to utilize statistically-preferred or statistically-favored codons within the species. The nucleotide sequence typically is examined at the DNA level and the coding region optimized for expression in the species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed genes, followed by a calculation of the average squared deviation. The formula used is: 1 SDCU=n=1 N [(Xn−Yn)/Yn] 2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusadotor(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, human), a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular plant or mammalian species, and modifying these codons in accordance with a codon usage table of the particular species to produce a codon optimized derivative. A modified nucleotide sequence may be fully or partially optimized for the particular species codon usage provided that the protein encoded by the modified nucleotide sequence is produced at a level higher than the protein encoded by the corresponding naturally occurring or native gene. Construction of synthetic genes by altering the codon usage is described in for example PCT Patent Application No. 93/07278.

In one embodiment, the nucleic acid sequence encoding the DNMT3 of this aspect of the present invention is codon-optimized for expression in human cells.

An example of a human codon optimized nucleic acid sequence encoding DNMT3 contemplated by the present invention is set forth in SEQ ID NO: 66.

According to a specific embodiment, the nucleic acid sequence encoding the DNMT3 of the present invention is not codon optimized for expression in gymnosperm or a bryophyte.

In addition, the nucleic acid sequence encoding the DNMT3 of the present invention is in a particular embodiment, not codon optimized for expression in a lycophyte or a charophyte.

To express the exogenous DNMT3 in a heterologous system (e.g. mammalian cells or plant cells), a polynucleotide sequence encoding the DNMT3 is preferably ligated into a nucleic acid construct suitable for cell expression in that system. Such a nucleic acid construct includes a promoter sequence for directing transcription of the polynucleotide sequence in the cell in a constitutive or inducible manner.

According to a specific embodiment, the expression vector comprises a polynucleotide encoding a catalytic domain of a species of a plant DNA methyltransferase 3 (DNMT3) protein operatively linked to a transcriptional regulatory sequence which is not of that species. Thus, for example if the expression vector encodes a DNMT3 of a gymnosperm or a bryophyte, then the present invention contemplates that the transcriptions regulatory sequence is not one which is naturally found in the gymnosperm or bryophyte (i.e. it is heterologous to the gymnosperm or bryophyte). In one embodiment, the transcriptional regulatory sequence is a sequence that induces expression in mammalian cells (e.g. CMV, SV40 or EF-1). In one embodiment, the transcriptional regulatory sequence is a sequence that induces expression in angiosperms.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

The polynucleotides of the present invention can be inserted into nucleic acid constructs to direct expression thereof in plant cells. In one embodiment, the plant cells are not gymnosperm or bryophyte cells. In another embodiment, the plant cells are angiosperm cells.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising Acacia spp., Acer spp., *Actinidia* spp., *Aesculus* spp., *Agathis australis, Albizia amara, Alsophila tricolor, Andropogon* spp., *Arachis* spp, *Areca catechu, Astelia fra-* grans, *Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

In other embodiments, the DNA methyltransferase of this aspect of the present invention is expressed in an agricultural plant. Agricultural plants include monocotyledonous species such as: maize (*Zea mays*), common wheat (*Triticum aestivum*), spelt (*Triticum spelta*), einkorn wheat (*Triticum monococcum*), emmer wheat (*Triticum dicoccum*), durum wheat (*Triticum durum*), Asian rice (*Oryza sativa*), African rice (*Oryza* glabaerreima), wild rice (*Zizania aquatica, Zizania latifolia, Zizania palustris, Zizania texana*), barley (*Hordeum vulgare*), Sorghum (*Sorghum bicolor*), Finger millet (*Eleusine coracana*), Proso millet (*Panicum miliaceum*), Pearl millet (*Pennisetum glaucum*), Foxtail millet (*Setaria italica*), Oat (*Avena sativa*), Triticale (Triticosecale), rye (*Secale* cereal), Russian wild rye (*Psathyrostachys juncea*), bamboo (Bambuseae), or sugarcane (e.g., *Saccharum arundinaceum, Saccharum barberi, Saccharum bengalense, Saccharum edule, Saccharum munja, Saccharum officinarum, Saccharum procerum, Saccharum ravennae, Saccharum robustum, Saccharum sinense,* or *Saccharum spontaneum*); as well as dicotyledonous species such as: soybean (*Glycine max*), canola and rapeseed cultivars (*Brassica napus*), cotton (genus *Gossypium*), alfalfa (*Medicago sativa*), cassava (genus *Manihot*), potato (*Solanum tuberosum*), tomato (*Solanum lycopersicum*), pea (*Pisum sativum*), chick pea (*Cicer arietinum*), lentil (*Lens culinaris*), flax (*Linum usitatissimum*) and many varieties of vegetables.

Constructs useful in the methods according to some embodiments of the invention may be constructed using recombinant DNA technology well known to persons skilled in the art.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include PMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells. Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra).

The gene constructs may be inserted into vectors, which may be commercially available, suitable for transforming into plants and suitable for expression of the gene of interest in the transformed cells. The genetic construct can be an expression vector wherein said nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of preferred promoters useful for the methods of some embodiments of the invention are presented in Tables 1-4.

TABLE 1

Exemplary constitutive promoters for use in the performance of some embodiments of the invention

| Gene Source | Expression Pattern | Reference |
| --- | --- | --- |
| Actin | constitutive | McElroy et al., Plant Cell, 2: 163-171, 1990 |

TABLE 1-continued

Exemplary constitutive promoters for use in the performance of some embodiments of the invention

| Gene Source | Expression Pattern | Reference |
|---|---|---|
| CAMV 35S | constitutive | Odell et al, Nature, 313: 810-812, 1985 |
| CaMV 19S | constitiutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitiutive | Bucholz et al, Plant Mol Biol. 25(5): 837-43, 1994 |
| Maize H3 histone | constitiutive | Lepetit et al, Mol. Gen. Genet. 231: 276-285, 1992 |
| Actin 2 | constitutive | An et al, Plant J. 10(1); 107-121, 1996 |

TABLE 2

Exemplary seed-preferred promoters for use in the performance of some embodiments of the invention

| Gene Source | Expression Pattern | Reference |
|---|---|---|
| Seed specific genes | seed | Simon, et al., Plant Mol. Biol. 5. 191, 1985; Scofield, et al., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al., Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltr1 promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al, Plant Cell Physiology 398) 885-889, 1998 |
| rice OSH1 | emryo | Sato et al, Proc. Nati. Acad. Sci. USA, 93: 8117-8122 |

TABLE 2-continued

Exemplary seed-preferred promoters for use in the performance of some embodiments of the invention

| Gene Source | Expression Pattern | Reference |
|---|---|---|
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma-kafirin | endosperm | PMB 32: 1029-35, 1996 |
| KNOX | emryo | Postma-Haarsma et al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, et al., Plant Mol. Biol. 19: 873-876, 1992 |

TABLE 3

Exemplary flower-specific promoters for use in the performance of the invention

| Gene Source | Expression Pattern | Reference |
|---|---|---|
| AtPRP4 | flowers | www(dot)salus(dot)medium(dot)edu/mmg/tierney/html |
| chalene synthase (chsA) | flowers | Van der Meer et al., Plant Mol. Biol. 15, 95-109, 1990. |
| LAT52 | anther | Twell et al., Mol. Gen Genet. 217: 240-245 (1989) |
| apetala-3 | flowers | |

TABLE 4

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |

TABLE 4-continued

Alternative rice promoters for use in the performance of the invention

| PRO # | gene | expression |
|---|---|---|
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 | strong root |
| PR00111 | uclacyanin 3-like protein | weak discrimination center/ shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PRO0228 | BLZ-2_long (barley) | |

In one embodiment, the promoter is not a gymnosperm or a bryophyte promoter. In another embodiment, the promoter is an angiosperm promoter.

Cells of the heterologous system (e.g. mammalian cells, or plant cells) may be transformed stably or transiently with the nucleic acid constructs of some embodiments of the invention. In stable transformation, the nucleic acid molecule of some embodiments of the invention is integrated into the genome of the organism and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

The present application further contemplates fusion proteins comprising the plant DNMT3s linked to DNA targeting moieties.

According to a particular embodiment, the DNA targeting moiety is a DNA endonuclease protein.

Contemplated endonuclease proteins include RNA-guided DNA endonuclease enzyme including for example zinc-finger nucleases (ZFNs), transcription activator-like effector nucleases (TALENs) and CRISPR associated protein.

In particular embodiments, the RNA-guided DNA endonuclease is Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 or Cpf1 endonuclease.

In one embodiment, the DNA targeting moiety comprises a catalytically inactive CRISPR associated 9 (dCas9) protein.

Cas9

Cas9 molecules of a variety of species can be used in the methods and compositions described herein. While the *S. pyogenes* and *S. thermophilus* Cas9 molecules are exemplified herein, Cas9 molecules of, derived from, or based on the Cas9 proteins of other species listed in US Patent Application No. 20160010076 can be used as well. Additional Cas9 proteins are described in Esvelt et al., Nat Methods. 2013 November; 10(11):1116-21 and Fonfara et al., "Phylogeny of Cas9 determines functional exchangeability of dual-RNA and Cas9 among orthologous type II CRISPR-Cas systems." Nucleic Acids Res. 2013 Nov. 22. doi:10.1093/nar/gkt1074.

The constructs and methods described herein can include the use of any of those Cas9 proteins, and their corresponding guide RNAs or other guide RNAs that are compatible. The Cas9 from *Streptococcus thermophilus* LMD-9 CRISPR1 system has been shown to function in human cells in Cong et al (Science 339, 819 (2013)). Additionally, Jinek et al. showed in vitro that Cas9 orthologs from *S. thermophilus* and *L. innocua*, can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells (e.g. human cells) or plant cells, containing mutations at D10, E762, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g., E762Q, H983N, H983Y, D986N, N863D, N863S, or N863H. The sequence of the catalytically inactive *S. pyogenes* Cas9 that can be used in the methods and compositions described herein is as set forth in SEQ ID NO: 23.

In some embodiments, the Cas9 nuclease used herein is at least about 50% identical to the sequence of *S. pyogenes* Cas9, i.e., at least 50% identical to SEQ ID NO: 23. In some embodiments, the nucleotide sequences are about 50%, 55%, 60%, 65%, 70%, 75%, 80%, 85%, 90%, 95%, 99% or 100% identical to SEQ ID NO: 23.

In some embodiments, the catalytically inactive Cas9 used herein is at least about 50% identical to the sequence of the catalytically inactive *S. pyogenes* Cas9, i.e., at least 50%, 55%, 60%, 65%, 70%, 75%, 80%, 85%, 90%, 95%, 99% or 100% identical to SEQ ID NO:24, wherein the mutations at D10 and H840, e.g., D10A/D10N and H840A/H840N/H840Y are maintained.

In some embodiments, any differences from SEQ ID NO:23 are in non-conserved regions, as identified by sequence alignment of sequences set forth in Chylinski et al., RNA Biology 10:5, 1-12; 2013; Esvelt et al., Nat Methods. 2013 November; 10(11):1116-21 and Fonfara et al., Nucl. Acids Res. (2014) 42 (4): 2577-2590, and wherein the mutations at D10 and H840, e.g., D10A/D10N and H840A/H840N/H840Y are maintained.

An exemplary nucleic acid sequence of human-codon optimized Cas9 is set forth in SEQ ID NO: 67.

The catalytic domain of the DNMT3 (or the full length DNMT3) may be linked directly to the DNA endonuclease protein or via a peptide linker.

The linker may comprise amino acids linked together by peptide bonds which serve as spacers such that the linker does not interfere with the biological activity of the fusion protein. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a particular embodiment, the amino acids in the linker are selected from glycine, alanine, proline, asparagine, glutamine, and lysine. Even more preferably, the linker is made up of a majority of amino acids that are sterically unhindered, such as glycine and alanine.

In one embodiment, the peptide linker is between 2 and 60 amino acids, between 2 and 50 amino acids, between 2 and 40 amino acids, between 2 and 30 amino acids, between 2 and 20 amino acids or even between 2 and 10 amino acids.

The DNMT3 may be linked to the C terminus of the endonuclease protein or the N terminus of said endonuclease protein.

The fusion proteins described herein may be provided as a kit together with particular guide RNAs (gRNAs).

The gRNA comprises a "gRNA guide sequence" or "gRNA target sequence" which corresponds to the target sequence on a target polynucleotide gene sequence.

The gRNA may comprise a "G" at the 5' end of the polynucleotide sequence. The presence of a "G" in 5' is preferred when the gRNA is expressed under the control of the U6 promoter. The gRNA may be of varying lengths. The gRNA may comprise at least a 10 nts, at least 11 nts, at least a 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of the target caspase 6 DNA sequence which is followed by a PAM sequence. The "gRNA guide sequence" or "gRNA target sequence" may be at least 17 nucleotides (17, 18, 19, 20, 21, 22, 23), preferably between 17 and 30 nts long, more preferably between 18-22 nucleotides long. In an embodiment, gRNA guide sequence is between 10-40, 10-30, 12-30, 15-30, 18-30, or 10-22 nucleotides long. The PAM sequence may be "NGG", where "N" can be any nucleotide. gRNA may target any region of a target gene which is immediately upstream (contiguous, adjoining, in 5') to a PAM (e.g., NGG) sequence.

Although a perfect match between the gRNA guide sequence and the DNA sequence on the targeted gene is preferred, a mismatch between a gRNA guide sequence and target sequence on the gene sequence of interest is also permitted as along as it still allows hybridization of the gRNA with the complementary strand of the gRNA target polynucleotide sequence on the targeted gene. A seed sequence of between 8-12 consecutive nucleotides in the gRNA, which perfectly matches a corresponding portion of the gRNA target sequence is preferred for proper recognition of the target sequence. The remainder of the guide sequence may comprise one or more mismatches. In general, gRNA activity is inversely correlated with the number of mismatches. Preferably, the gRNA of the present invention comprises 7 mismatches, 6 mismatches, 5 mismatches, 4 mismatches, 3 mismatches, more preferably 2 mismatches, or less, and even more preferably no mismatch, with the corresponding gRNA target gene sequence (less the PAM). Preferably, the gRNA nucleic acid sequence is at least 90%, 91%, 92%, 93%, 94%, 95%, 96%, 97%, 98% and 99% identical to the gRNA target polynucleotide sequence in the gene of interest. Of course, the smaller the number of nucleotides in the gRNA guide sequence the smaller the number of mismatches tolerated. The binding affinity is thought to depend on the sum of matching gRNA-DNA combinations.

Any gRNA guide sequence can be selected in the target nucleic acid sequence, as long as it allows introducing at the proper location, the patch/donor sequence of the present invention. Accordingly, the gRNA guide sequence or target sequence of the present invention may be in coding or non-coding regions a gene (i.e., introns or exons).

In one embodiment, the gRNA is a sgRNA.

As used herein, the term "sgRNA" refers to single guide RNA used in conjunction with CRISPR associated systems (Cas). sgRNAs are a fusion of crRNA and tracrRNA and contain nucleotides of sequence complementary to the desired target site. Jinek et al., "A programmable dual-RNA-guided DNA endonuclease in adaptive bacterial immunity" Science 337(6096):816-821 (2012) Watson-Crick pairing of the sgRNA with the target site permits R-loop formation, which in conjunction with a functional PAM permits DNA cleavage or in the case of nuclease-deficient Cas9 allows binds to the DNA at that locus.

Modified RNA oligonucleotides such as locked nucleic acids (LNAs) have been demonstrated to increase the specificity of RNA-DNA hybridization by locking the modified oligonucleotides in a more favorable (stable) conformation. For example, 2'-O-methyl RNA is a modified base where there is an additional covalent linkage between the 2' oxygen and 4' carbon which when incorporated into oligonucleotides can improve overall thermal stability and selectivity.

Thus, the gRNAs disclosed herein may comprise one or more modified RNA oligonucleotides. For example, the truncated guide RNAs molecules described herein can have one, some or all of the region of the guide RNA complementary to the target sequence are modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In other embodiments, one, some or all of the nucleotides of the gRNA sequence may be modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In some embodiments, the single guide RNAs and/or crRNAs and/or tracrRNAs can include one or more Adenine (A) or Uracil (U) nucleotides on the 3' end.

The guide RNA may be provided per se or in an expression vector. The vectors for expressing the guide RNAs can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

According to another aspect of the present invention there is provided a method of increasing methylation of DNA in a cell, the method comprising expressing a polynucleotide encoding a catalytic domain of a plant DNA methyltransferase 3 (DNMT3) protein in the cell, thereby increasing methylation of DNA in the cell. In one embodiment, the cell is not of a gymnosperm plant.

In one embodiment, the catalytic domain is introduced into the cell as a fusion protein (e.g. linked to a DNA targeting moiety, as described herein above).

Together with the fusion proteins of the present invention (or polynucleotides encoding same), the gRNAs may be introduced into a wide variety of cell types, embryos at different developmental stages, tissues and species may be targeted, including somatic and embryonic stem cells of human and animal models. In one embodiment, the cell is a stem cell (e.g. a pluripotent stem cell such as an embryonic stem cell or an induced pluripotent stem cell), a mesenchymal stem cell, a tissue stem cell (e.g. a neuronal stem cell or muscle stem cell). In another embodiment, the cell is a healthy cell. In another embodiment, the cell is a diseased cell (e.g., a cancer cell).

In other embodiments the fusion protein (and gRNA) may be injected into the cell. This is particularly relevant for editing of single cells, eggs or embryonic stem cells.

Following introduction of the fusion protein and gRNA described herein, the gene (at the targeted site) may be analyzed to ensure (i.e. confirm) that methylation has occurred. Thus, for example bisulfite sequencing may be carried out to determine the extent of methylation prior to and/or following the treatment.

Bisulfite sequencing (also known as bisulphite sequencing) is the use of bisulfite treatment of DNA to determine its pattern of methylation.

Treatment of DNA with bisulfite converts cytosine residues to uracil, but leaves 5-methylcytosine residues unaffected. Therefore, DNA that has been treated with bisulfite retains only methylated cytosines. Thus, bisulfite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information. The objective of this analysis is therefore reduced to differentiating between single nucleotide polymorphisms (cytosines and thymidine) resulting from bisulfite conversion.

As described in Example 3, introduction of the DNMT3s of the present invention can lead to alteration in expression levels of particular genes. Thus, the present inventors further contemplate analyzing the expression level of relevant genes to uncover the effect methylation has on gene expression.

It is envisaged by the present inventors that enhancement of methylation at particular sites may aid in treating diseases which are associated with hypo-methylation. Such diseases include for example autoimmune diseases (multiple sclerosis, rheumatoid arthritis, lupus, metabolic disorders (diabetes, lipid related disorders, obesity), neurological disorders (autism, Parkinson's disease) and aging (see for example Jin and Liu [Genes Dis. 2018 March; 5(1): 1-8], the contents of which are incorporated herein by reference.

It is expected that during the life of a patent maturing from this application many relevant plant DNMT3s will be uncovered and the scope of the term plant DNMT3 is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879, 262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Biological Materials

All mutant plants were generated in the background of 'Gransden 2004' strain of *P. patens*[50,59] and were propagated on BCD or BCDAT media[60] at 25° C. under a 16 h light and 8 h dark regime[61]. Plant morphology was documented as previously described[62].

Generation of Transgenic Mutant Lines

*P. patens* single deletion mutant lines for the following genes: PpDRM1 (Pp3c15_14360V1.1), PpDRM2 (Pp3c15_21430V1.1), PpDNMT3a (Pp3c3_3540V1.1) and PpDNMT3b (Pp3c13_8320V1.1) were generated by replacing the genomic region coding for the methyltransferase domain with either the hygromycin resistance cassette (hptII) or the G418 resistance cassette (nptII) via homologous recombination (illustrated in FIG. 6). Genomic fragments corresponding to the 5' and 3' flanking regions of the deleted sequence were amplified using KOD hot start DNA polymerase (Novagen), cloned into the pTZ57 vector (Fermentas) and sequenced to validate their integrity. Next, the 5' and 3' fragments were subcloned into either the pMBL5 vector (GenBank: DQ228130.1) or the pMBL5 Nos Hyg vector[36]. Constructs were introduced into protoplasts via PEG-mediated transformation as described[60] using 15 µg of plasmid restricted to linearize the construct. Six days after regeneration, transformants were selected on BCDAT medium containing 25 µg/ml hygromycin (Duchefa) or 25 µg/ml G418 (calbiochem). Resistant plants were further tested by tissue PCR[36] to verify correct integration of the construct into the genome, by amplifying the junction regions between the insert and the sequence flanking the deleted fragment at both the 5' and 3' ends (primers listed in Table 6). In addition, loss of the endogenous targeted loci was correlated with lack of amplification of the targeted sequence as compared to a positive control. ΔPpdrm2 and ΔPpdnmt3a single deletion mutant protoplasts were used to generate ΔPpdrmΔPpdrm2 and ΔPpdnmt3aΔPpdnmt3b double deletion mutant lines, respectively, as described above.

Generation of RPS Transgenic Lines

The RPS transgene was introduced into the genome of WT and mutant plants via non-homologous recombination. To this end, a pMBL5+Zeo vector was constructed by subcloning the Zeocin resistance cassette (Sh ble gene) from pRT101-Zeo[63] replacing the G418 resistance cassette (nptII gene) of the pMBL5 vector (GenBank: DQ228130.1). The RPS fragment was subcloned from the p35 GUS/RPS vector[38] into pMBL5+Zeo vector. Both the RPS and Zeocin resistance cassettes were sequenced in the final pMBL5+Zeo+RPS construct to ensure integrity. Following transformation (as described above) and selection on BCDAT medium containing 50 µg/ml Zeocin (Invivogen), resistant plants were tested to verify insertion of the construct into the genome by tissue PCR[36] amplifying an internal transgene sequence spanning both the RPS sequence and the selection cassette (primers listed in Table 6).

Search of RPS Homologues Sequences in *P. patens* Genome and sRNAome

The RPS sequence (GenBank: X92381.1) was used for homology search (blastn) in the *P. patens* V3.0 genome[64]. Additionally, it was used to search for corresponding small RNAs by NCBI SRA-Blast[65] using small RNA-seq data of *P. patens* protonema[40] (SRX247005-SRX247008 and SRX327325-SRX327330).

Published Genomic Data

Data for sRNA were derived from[40], for mRNA from[5], and for histone modifications from[43].

Bisulfite Sequencing of the RPS Transgene

A fragment of RPS was PCR amplified from bisulfite treated genomic DNA, extracted from protonema tissue, using primers RPS-top-R-new and RPS-top-F (primers listed in Table 6) and KAPA HiFi Uracil+ polymerase (kappa biosystems), then cloned into pJET1.2 (Thermo Fisher Scientific). The methylation status of individual clones was determined by Sanger sequencing.

Phylogenetic Analysis

PpDNMT3b and PpDRM2 protein sequences were used to search for homologs by blastp versus NCBI Non-redundant protein database[66] and by tblastn versus the 1000 plants (1 kp) transcriptome database[67-70]. Alignment of selected DNMT3, DRM and DNMT1 MTD protein sequences was performed using MUSCLE v3.8.31[71]. The motif order was rearranged in DRM sequences to match the linear organization of canonical DNMTs. Protein accessions are listed in Table 5. MTDs of animal and plant DNMT1/MET1 homologs were added as an outgroup. The phylogenetic tree was constructed by IQ-TREE v1.6.4[72-74] using default parameters and illustrated by FigTree v1.4.3 (www(dot)tree(dot)bio(dot)edac(dot)uk/software/figtree/).

BS-seq Library Preparation

About 500 ng of genomic DNA isolated from protonema was fragmented by sonication, end repaired, and ligated to custom synthesized methylated adapters (Eurofins MWG Operon) according to the manufacturer's (Illumina) instructions for gDNA library construction. Adaptor-ligated libraries were subjected to two successive treatments of sodium bisulfite conversion using the EpiTect Bisulfite kit (QIAGEN) as outlined in the manufacturer's instructions. The bisulfite-converted libraries were then amplified by PCR using the following conditions: 2.5 U of ExTaq DNA polymerase (Takara Bio), 5 µl of 10×Extaq reaction buffer, 25 mM dNTPs, 1 µl Primer 1.1, 1 µl Primer 2.1 (50 µl final). PCR reactions were carried out as follows: 95° C. for 3 min, then 12-14 cycles of 95° C. for 30 s, 65° C. for 30 s, and 72° C. for 60 s. The enriched libraries were either gel purified (~300 bp band) or purified with the solid-phase reversible immobilization method using AM-Pure beads (Beckman Coulter) prior to quantification with a Bioanalyzer (Agilent). Deep sequencing was performed on Illumina Hi-Seq 2000.

BS-Seq Data Analysis BS-seq data processing was performed as described[54]. In short, custom Perl scripts were used to convert all the Cs in the 'forward' reads (and in the scaffold) to Ts, and all the Gs in the 'reverse' reads and scaffold to As. The converted reads were aligned to the converted scaffold using Bowtie2 aligner v2.3.2[75]. Perl scripts were used to recover the original sequence information and, for each C (on either strand), count the number of times it was sequenced as a C or a T. For each sequence context (CG, CHG, CHH) the genomic averaged fractional methylation was calculated (Table 7 and FIGS. 3A-G), as well as fractional methylation within a 50 bp sliding window that were used in downstream analyses.

TE Frequency Meta-Analysis

The abundance of TEs near TSSs of *P. patens* and *A. thaliana* genes was assessed using publicly available genes and TEs annotations and a custom Perl script, which creates a histogram of scores relative to edges of entries from one annotation file based on the presence of entries from another annotation file. Gene annotations (v3.3 for *P. patens*, Araport11 for *Arabidopsis*) and *A. thaliana* TE annotation (TAIR10) were downloaded from www(dot)phytozome(dot)org. *P. patens* TE annotation[42] was downloaded from www(dot)genomevolution(dot)org. TE annotations were reformatted to contain separate entries for start and end positions of each TE, and to assign each entry a score of 1. For each gene, the presence of TE edge was tested in a 25 bp sliding window up to 500 bp upstream to TSS, assigning "positive" windows with scores. In order to count only one edge of a TE closest to each gene, this analysis was performed separately on TEs "ends" against genes on the plus strand, and vice versa. Then, genes were aligned at TSS, and the percentage of genes with a TE ending in each 25 bp window were calculated.

Percent Methylation Change

This number was calculated by dividing the difference in methylation level between two samples by the level of methylation in the sample with the higher methylation level. For example, percent-methylation-change between WT and cmt was calculated as follows:

$$\frac{WT\ mCHH - cmt\ mCHH}{WT\ mCHH} * 100\ if WT\ mCHH > cmt\ mCHH -$$

$$\frac{cmt\ mCHH - WT\ mCHH}{cmt\ mCHH} * 100\ if WT\ mCHH < cmt\ mCHH$$

Box Plots

Box plots compare percent-methylation-change within 50-bp windows with CHH methylation level of at least 0.1 in either of the samples, and with at least 20 informative sequenced cytosines. To examine the correlation between methylation change and chromatin structure, TE windows are separated into centiles in ascending order according to siRNA (24 nt sRNA), GC ratio, H3K9me2, H3K4me3, TE size, and TE LTR/INT annotations. GC ratio and TE size were divided into five centiles. siRNA counts were divided into 10 centiles, which due to the high abundance of score 1 windows, only centile 1, 7, 9, and 10 are showing. H3K9me2 and H3K4me3 are Log 2 ratio over total H3 that were divided into four centiles. For H3K9me2 and H3K4me3, an additional category, ND, was added, that corresponded to windows that did not have any signal in either H3K9me2, H3K4me3 or H3.

Identification of DMRs

Fractional methylation in 50 bp windows across the genome was compared between WT and each of the DNMT mutants. DMRs were called for windows with at least 0.1 fractional methylation, 10 informative sequenced cytosines, and Fisher's exact test p-value <0.05.

Accession Numbers

Sequencing data have been deposited in Gene Expression Omnibus under accession number GSE116837.

Results

DNMT3s are Persistent in Plants and are Evolutionary Distinct from DRMs

*P. patens* encodes two DNMT3s, designated here as PpDNMT3a and PpDNMT3b, which are composed of a DNMT3-type N-terminal MTD and a C-terminal domain of unknown function 3444 (DUF3444)[18]. Genome and transcriptome searches revealed that the protein organization is conserved among non-flowering streptophytes DNMT3s. The existence of two-full length DNMT3 homologs in two distantly-related gymnosperm subclasses that were separated around 300 million years ago implies that DNMT3 persists in gymnosperms. DNMT3 was not detected in any available angiosperm genomes or transcriptomes, supporting the notion that DNMT3 completely disappeared from this plant lineage. Phylogenic analysis of the MTD show that plant DNMT3s form a monophyletic clade together with animal DNMT3s which is separated from the DRM clade (FIG. 1A), suggesting the functional conservation of DNMT3s among plants and animals and/or functional speciation between plant DNMT3 and DRM proteins. Additionally, while DRM paralogs are common along plant evolution, they diverged into distinct orthologs only in seed plants, e.g. DRM2 and DRM3 in angiosperm (FIG. 1A), implying further functional diversification of DRMs in this plant lineage. Paralogs of plant DNMT3s are also common, however based on our evolutionary analysis, these duplications did not evolve into conserved DNMT3 ortholog families across multiple species (FIG. 1A). Of note, PpDNMT3a and PpDNMT3b are not orthologs of mammalian DNMT3a and PpDNMT3b, respectively (FIG. 1A). Similarly, PpDRM1 and PpDRM2 are not orthologs of angiosperm DRM1 and DRM2, respectively (FIG. 1A). In summary, while DRMs are commonly considered as the plant homologs of eukaryotic DNMT3, here it is shown that DRMs are evolutionary distinct from DNMT3, and that true DNMT3 plant homologs exist throughout the plant kingdom, except in angiosperm.

PpDNMT3b and PpCMT Establish De Novo Methylation and Maintain the Non-CG Methylome To determine the role of *P. patens* DNMTs in DNA methylation, the methylomes of *P. patens* DNMT deletion mutant plants, namely met, cmt, dnmt3a, dnmt3b, drm1, and drm2 single deletion mutants, as well as in drm 1/drm2 (drm12) and dnmt3a/dnmt3b (dnmt3ab) double deletion mutants 35,36; (FIG. 6) were profiled. All single and double DRM and DNMT3 mutants were viable and developed similarly to wild type (WT) (FIGS. 7A-U). Genomic methylation averages clearly showed that CG, CHG, and CHH sites were nearly eliminated and specifically disrupted in met, cmt, and dnmt3b mutants, respectively (FIG. 1B). More precisely, met mutant lost 93% of CG methylation, cmt mutant lost 97% of CHG methylation, and dnmtb mutant lost 95% of CHH methylation (FIG. 1B and Table 7). The dnmt3ab double mutant lost 95% of CHH methylation, which is comparable to the CHH loss in dnmt3b single mutant. Neither dnmt3a, drm 1, drm2 single mutants nor drm 12 double mutant showed any significant global hypomethylation in any of the sequence contexts (FIG. 1B). These complete and specific hypo-methylations in *P. patens* DNMT mutants led to the conclusion that CG, CHG, and CHH contexts in *P. patens* are directly and primarily methylated by PpMET, PpCMT, and PpDNMT3b, respectively.

Figure 1C:
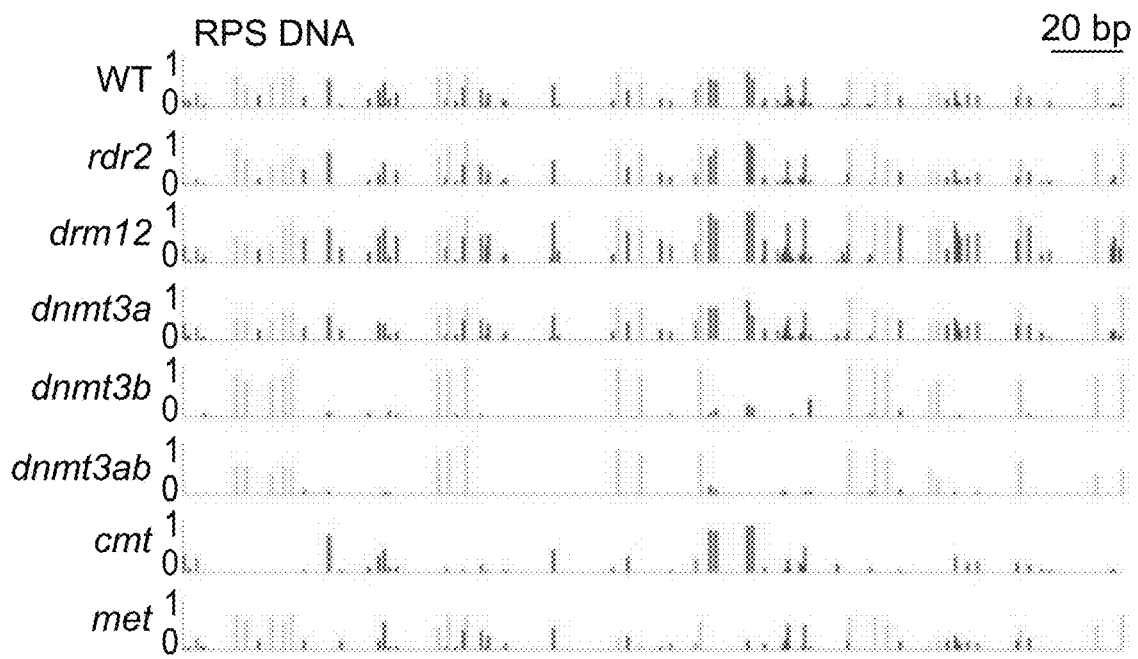

Testing for the Loss of Preexisting Methylation in Mutant Backgrounds Accounts for Maintenance Methylation To evaluate the activity of *P. patens* DNMTs in de novo methylation, the repetitive DNA sequence (RPS) from *Petunia hybrida*[37-39], uncommon to moss, was introduced into *P. patens*. DNA methylation analysis of RPS was conducted in the first transgenic generation (T1) and within the same transformed plant tissue. Using bisulfite sequencing, it was found that RPS is methylated in WT cells in all three methylation contexts, CG, CHG, and CHH (FIG. 1C), implying that it can be de novo methylated in *P. patens*. By introducing and examining RPS methylation in the various DNMT mutants, it was found that CG methylation is significantly reduced in met, dnmt3b and dnmt3ab mutants (paired t-test p-value <0.0016, 0.0023, 0.0022, respectively), CHG methylation is specifically and significantly reduced in cmt mutants (paired t-test p-value <$10^{-5}$), and CHH methylation is eliminated in dnmt3b and dnmt3ab mutants (paired t-test p-value <$10^{-5}$ for both) while unchanged in dnmt3a. In drm12 mutant, RPS was methylated same as in WT. In angiosperms, DRMs are directed to the DNA by 24 nt small interfering RNA (siRNA)[27]. Accordingly, the ability of RPS to undergo de novo methylation in *P. patens* plants mutated in the RNA Directed RNA polymerase 2 (PpRDR2) and subsequently depleted of siRNA[40] was tested. Similarly to drm12, it was found that RPS is regularly methylated in *P. patens* rdr2 mutant plants.

Altogether, these context-specific RPS methylation phenotypes in each of the mutants suggest that de novo methylation in *P. patens* can be mediated by DNMT3b at CG and CHH sites and by CMT at CHG sites without the involvement of DRMs or the canonical RdDM pathway. The reduction of CG methylation in RPS DNA in met T1 plants suggests that de novo CG methylation of RPS is relied also on PpMET. Alternatively, CG hypomethylation in met mutant could suggest that CG methylation in RPS is dependent on PpMET maintenance activity within just a few rounds of somatic cell generations.

PpDNMT3b and PpCMT Regulate Genomic CG Methylation

The near-complete elimination of CG methylation in the met genome (FIG. 1B) suggests that unlike animal DNMT3, PpDNMT3s do not play a role in maintaining genomic CG methylation. However, by focusing on transposable elements (TEs), a consistent decrease of 13% in CG methylation in both single dnmt3b and double dnmt3ab mutants was found (FIG. 2A), suggesting that DNMT3b is partially involved in maintaining the CG methylome. Further dissection of CG methylation based on their neighboring 5' nucleotides, i.e. NCG sites (N=any nucleotide), revealed that ACG sites are preferentially hypomethylated in dnmt3b and dnmt3ab (FIG. 2B). In association with the particular ACG hypo-methylation in dnmt3b plants, it was found that in met mutants, ACG sites exhibit the highest residual CG methylation levels (FIG. 2C).

Among the four NCG sites, CCGs had the lowest CG-hypomethylated effect in dnmt3b mutants (FIG. 2B). CCG is one form of CHG for which it was previously shown that its methylation (mCCG) in the entire *Arabidopsis* genome and a couple of examined sequences in *P. patens*, is dependent on the methylation of the internal CG site (CmCG) regulated by MET1 genes[36]. Here, this observation was extended to the entire *P. patens* genome by showing that CHG methylation, specifically at CCG sites, is diminished in the met mutant (FIG. 2E). This contributed to a 13% reduction in CHG methylation at TE sequences (FIG. 2D). Interestingly, it was found that the reciprocate effect also exists, i.e. CmCG dependency on mCCG. Out of the four NmCG methylation contexts, CmCG is particularly reduced in the cmt mutant (FIG. 2B), while in met mutant CmCG residual level is second to ACG (FIG. 2C). Accordingly, along with their de novo methylation activities these results demonstrate the ability of PpCMT and PpDNMT3b to bring about CG methylation at genomic CCG and DCGs (D=A, G, or T) sites, respectively.

Non-CG methylation by mammalian DNMT3 is targeted preferentially to CW sites (W=A or T), such as CAC and CAG[24]. Herein, it was found that CHH methylation (mediated by PpDNMT3b) preferentially targets CWH sites (FIG. 8), suggesting functional conservation of CW methylation between mammalian and moss DNMT3s. However, the particular regulation of CHG methylation (including CWG) by PpCMT (FIG. 2E), infers diversification of PpDNMT3b by avoiding methylating CWG sites that are controlled solely by PpCMT.

Figure 3A:
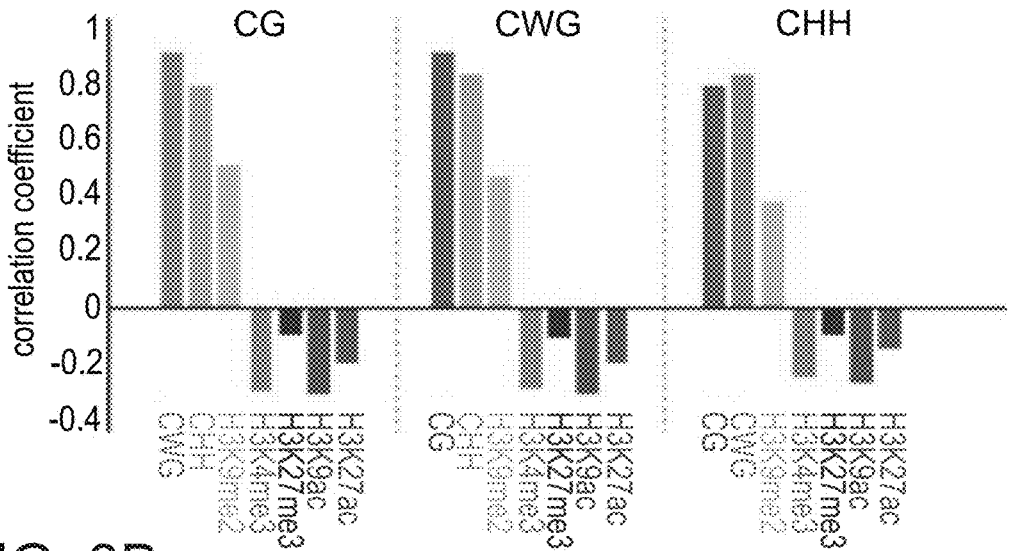
Figure 3B:
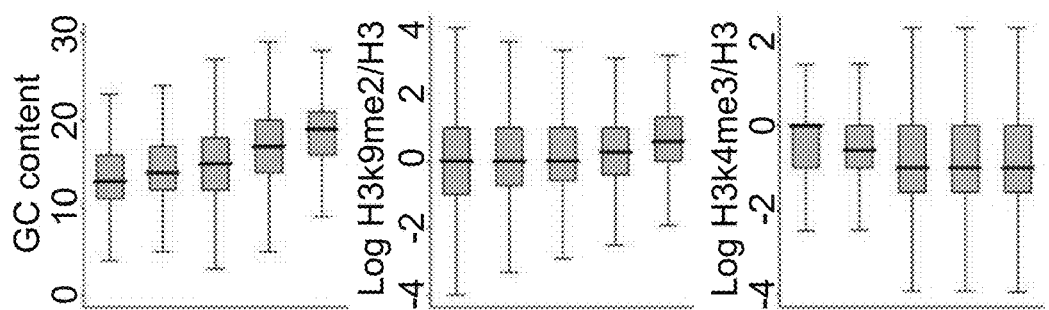
Figure 3C:
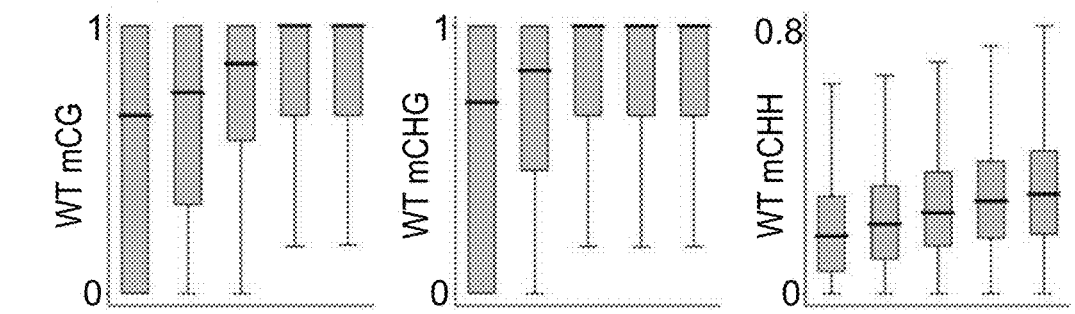
Figure 3D:
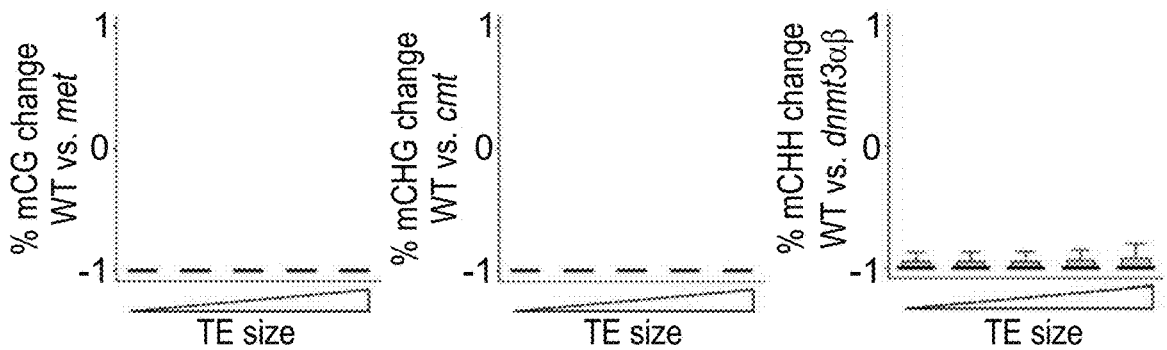

PpDNMT3b-Dependent CHH Methylation Preferentially Targets Heterochromatin and is Partially Regulated by PpCMT DNA methylation in *P. patens* is specifically targeted to transposable elements (TEs) (FIG. 9) and segregated away from genes[5]. Only about 0.5% of the methylated cytosines reside within genic sequences, which are mostly transcriptionally silenced[42] and are controlled by PpDNMTs similarly to the way TE methylation is regulated by PpDNMTs (FIG. 9). In agreement, DNA methylation in *P. patens* is positively associated with heterochromatic (i.e. H3K9me2) and negatively associated with euchromatic (e.g. H3K4me3) marks (FIG. 3A)[42,43]. It is further shown, that similar to *Arabidopsis*, long TEs in *P. patens* tend to be more heterochromatic, whereas short TEs are more euchromatic (FIG. 3B)[22]. Consistent with the relationship with heterochromatin, it was found that DNA methylation levels associate with TE size, i.e. they accumulate at relatively longer TEs (FIG. 3C). These correlations of DNA methylation with heterochromatin, together with the complete or near complete elimination of CG, CHG, and CHH methylation in met, cmt, and dnmt3b mutants (FIG. 1B, 3D), respectively, suggest that PpMET, PpCMT and PpDNMT3b function preferentially within heterochromatic TE sequences.

Figure 3E:
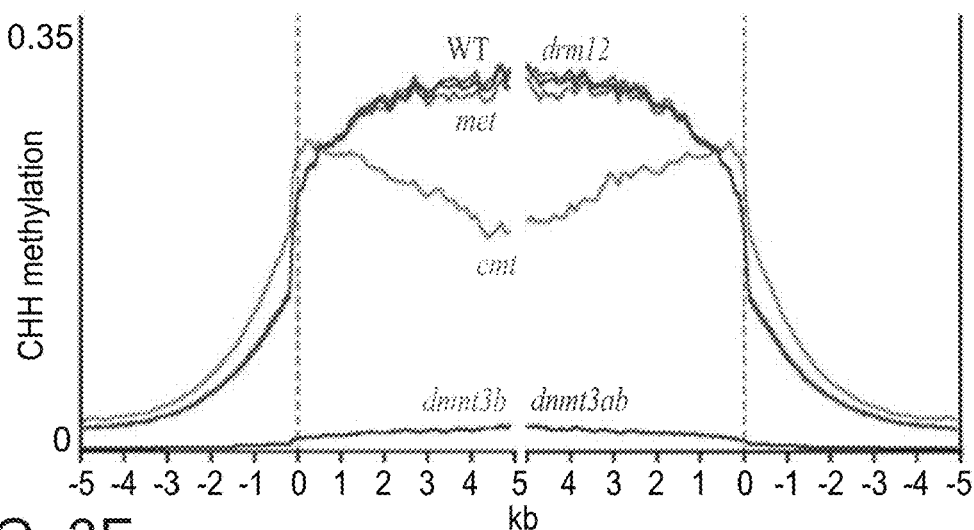
Figure 3F:
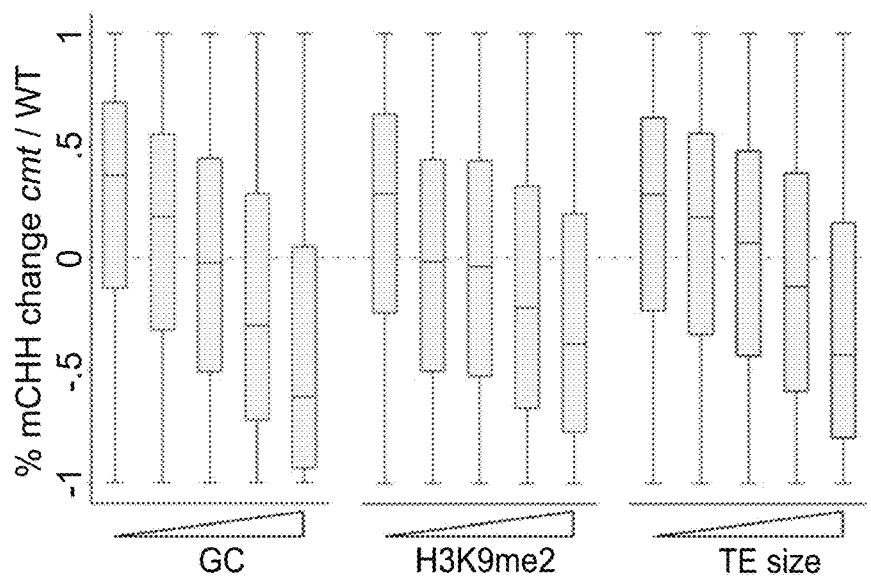
Figure 3G:
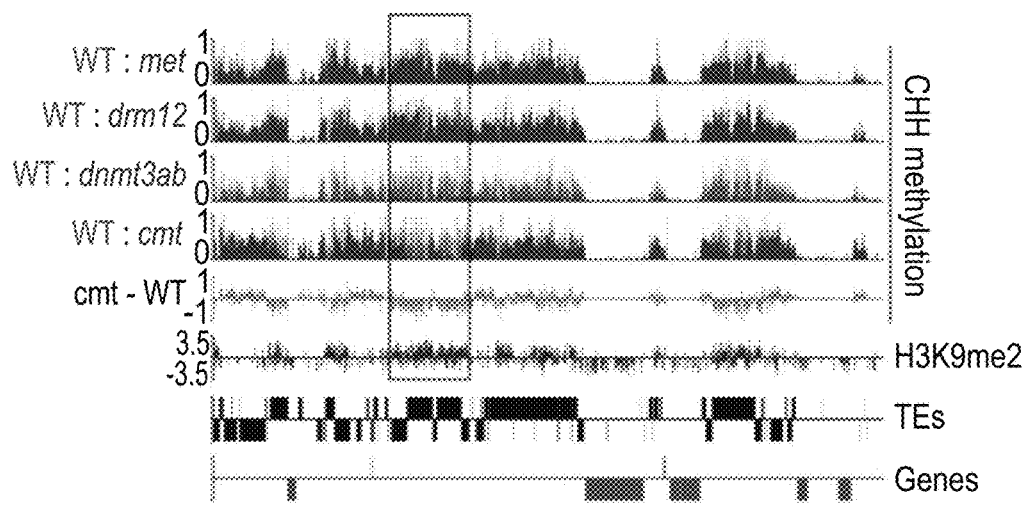
Figure 4A:
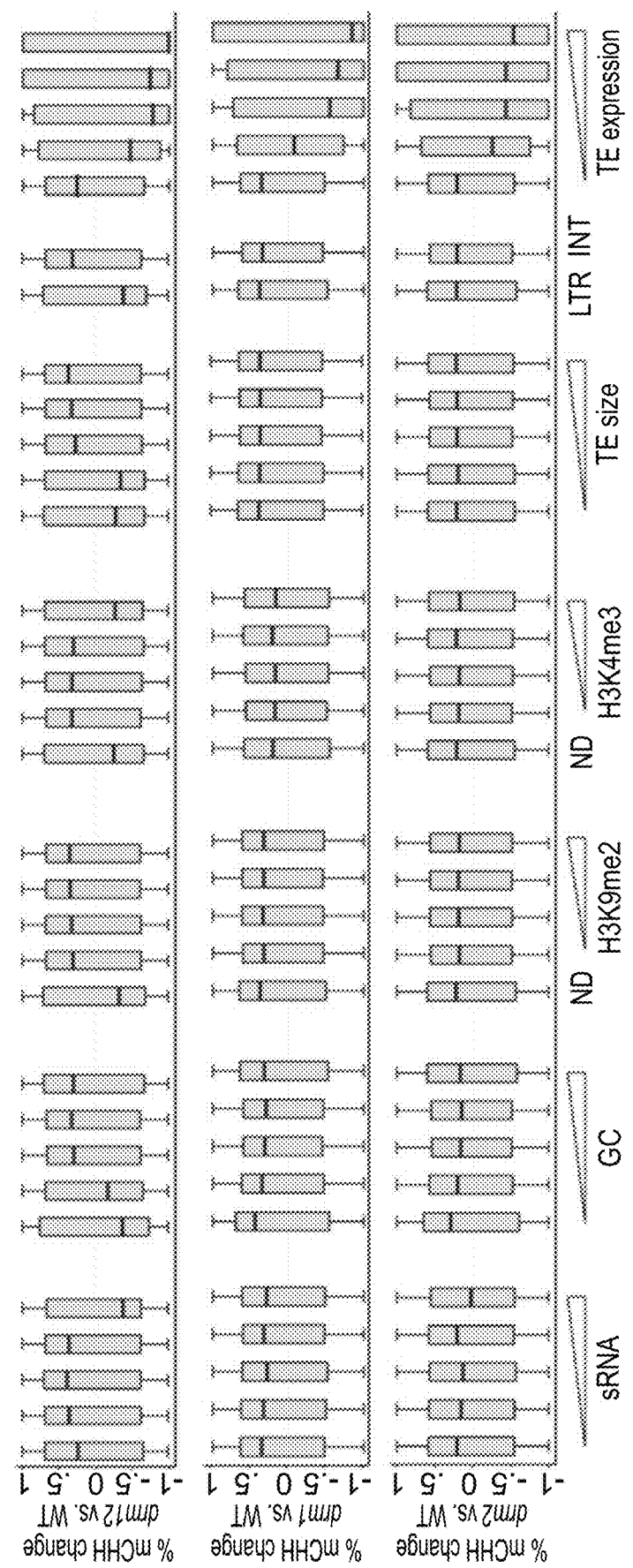

Interestingly, while genome wide CHH methylation in *P. patens* cmt mutant was similar to levels in WT (FIG. 1B), when profiling methylation along TEs, it was found that CHH methylation in cmt mutant is substantially altered, i.e. increased closer to TE-edges and gradually decreased inward into the elements (FIG. 3E). In the TE meta-analysis short and long TEs are relatively enriched and depleted closer and away to the points of TE-alignment, respectively (FIG. 10A). Consequently, it was found that CHH methylation in cmt is preferentially hypo-methylated in long TEs and hyper-methylated in short ones (FIG. 3F). In accordance with the association of TE size with chromatin configuration (FIG. 3B), it was found that CHH methylation in cmt mutant is preferentially depleted at genomic regions enriched for GC nucleotides and H3K9me2, and particularly increased within low GC and H3K9me2 TE regions (FIGS. 3F, G). When focusing on short TEs (<500 bps), it was found that hyper- and hypo-methylation in cmt background continue to associate with eu- and hetero-chromatic regions, respectively (FIG. 10B), suggesting that the chromatin structure, rather than TE size, determines the CHH methylation effect in cmt mutant. Overall, the results suggest that PpMET, PpCMT and PpDNMT3b function preferentially at H3K9me2-heterochromatic regions, and that PpDNMT3b CHH methylation activity is regulated to some extent by PpCMT.

PpDRMs Target Transcribed Euchromatic TEs

Neither drm1, drm2, nor drm12 mutants showed reduction of global genomic methylation (FIG. 1B and FIG. 10A). Similar to drm mutants, no effect on methylation was recently reported for P. patens rdr2 mutant[40], which is validated herein. The analysis was expanded to a larger genomic portion (80% vs. 20%; FIG. 10A and Table 7). These results, together with the complete CG, CHG, and CHH hypo-methylation in met, cmt, and dnmt3b mutants, respectively (FIG. 1B), imply a trivial methylation activity of DRMs and RDR2 in P Patens.

As opposed to a global phenotype, the present inventors next checked for a localized methylation effect in drm mutants within statistically supported differentially methylated regions (DMRs) separated into distinct chromatin configurations. While hypo-methylated DMRs were not significantly enriched over hyper-methylated DMRs in neither the drm nor the rdr2 mutants (FIG. 10B), it was found that CHH-DMRs of drm12 double mutant are particularly hypo-methylated within genomic regions enriched for siRNA, low GC content, low histone H3 abundancy, high H3K4me3, short TEs, and long-terminal-repeat (LTR) regions of retrotransposons (FIG. 4A—top panel). drm1 and drm2 CHH-DMRs were mostly hyper-methylated and did not associate with any chromatin or DNA features (FIG. 4A lower panels), thus implying an unrelated noise, which is a common feature of asymmetric methylation. Under this assumption, the particular hypomethylation effect in drm12 (FIG. 4A top panel) suggests some functional redundancy between DRM1 and DRM2. Intriguingly, it was found that CHH-DMRs of single and double drm mutants as well as of rdr2 are gradually hypo-methylated within a small number of windows (<=5610) of expressed TEs (FIG. 4A right panels and FIGS. 10C and D), which are also abundant in H3K4me3 and depleted of H3K9me2 (FIG. 10E). Overall, these results associate PpDRMs methylation activity with RDR2 generated siRNA as well as with actively-transcribed euchromatic TE sequences, both of which are signatures of RdDM activity in angiosperm.

The weak genomic methylation activity of DRMs in P. patens could be explained by the exceptional high efficiency of PpCMT and PpDNMT3b. PpCMT targets CHG methylation as strongly as PpMET targets CG methylation (FIGS. 2A, D, 4E) while PpDNMT3b targets CHH methylation with more than the double the level of Arabidopsis CHH methylation activity (FIG. 4E)[44]. Consequently, together with their ability to de novo methylate DNA, it is possible that PpCMT and PpDNMT3b target and maintain non-CG methylation even within euchromatic regions that have a weak heterochromatic signal.

In support of a trivial role for RdDM in P. patens, it was found that siRNA in P. patens overlap with only 5% of methylated TEs, in comparison to 65% in Arabidopsis (FIG. 4B). Moreover, similar to Arabidopsis, siRNA in P. patens was found to be enriched within long-heterochromatic TEs (FIG. 4C). In Arabidopsis, RdDM functions mostly in euchromatic TEs, while heterochromatic siRNAs are hardly involved in maintaining DNA methylation 22,45,46 If the same is true in P. patens, then the exceptionally low abundance of siRNA in euchromatic TEs (0.9%) could further explain the minor role of PpDRMs in genomic methylation.

In addition to actively transcribed TEs, another source for euchromatic TEs could be those located in gene promoters[22,47]. Notably, the frequency of TE integration within the first 200 bp upstream to transcription start site (TSS) of genes, was found to be lower by up to 2.3 times in P. patens than in Arabidopsis (FIG. 4D). This result is counterintuitive, considering that the P. patens genome contains eight times more TEs than that of Arabidopsis, which are also spread more evenly along the chromosomes in comparison to the centric concentration of TEs in Arabidopsis[42]. Hence, the particular depletion of TEs in P. patens from gene promoters, which are known to be the main target of DRMs and RdDM in angiosperms[22,47-49], could contribute to the weak genomic methylation effect of PpDRMs and RDR2 in P. patens.

To date, functional analyses of plant DNMTs were focused primarily on Arabidopsis and a few additional angiosperms. P. patens is a basal land plant that diverged from angiosperms about 400 million years ago 50 and encodes homologs of all four plant DNMT protein families 18, including DNMT3 which has been lost during angiosperms evolution. Thus, the present comprehensive analysis of the entire PpDNMT proteins under de novo and homeostasis methylation conditions allowed the present inventors to reveal their function as well as to infer on the evolutionary mechanisms of DNA methylation in plants (FIGS. 5A-B).

Mammalian DNMT3s function primarily as de novo methylases of CG sites and in some tissues also of CH sites[24,51]. The present inventors show here that PpDNMT3s are required for de novo methylation of CG and CHH sites (FIG. 1B). As PpDNMT3b is the first non-animal DNMT3 to be functionally characterized, the results imply that de novo methylation of CG and non-CG sites is an ancient feature of eukaryotic DNMT3 that predates the divergence of plant and animal DNMT3s. Additionally, the data demonstrate the ability of DNMT3 to be specialized in their hosts, such as the preference of mammalian DNMT3 towards CG sites and that of moss DNMT3 towards CHH sites. Conservation and diversification between mammalian and moss DNMT3s would provide the basis for further structure-function interactions of eukaryotic DNMT3. The narrow overlap of siRNA with DNA methylation (FIG. 4B) and the trivial methylation effect in Pprdr2 (FIG. 1C and FIG. 10A), suggest that the robust genomic methylation of PpDNMT3 does not involve the RdDM pathway. In comparison, the association between PpDRMs methylation effect, siRNA signal (FIG. 4A), and PpRDR2 methylation profile (FIG. 10D) link basal DRMs with RdDM. Consequently, these results suggest that since its emergence RdDM included DRMs rather than DNMT3s as its methylase component (FIG. 5B).

RPS methylation by PpCMT (FIG. 1C) is the first in vivo evidence for de novo methylation by a CMT protein. In vitro studies have shown that Arabidopsis CMT2 and CMT3 can methylate unmethylated-DNA templates[20,21]. Thus, it is possible that CMTs in Arabidopsis and other angiosperms are capable of mediating de novo methylation, as well (FIG. 5A). CMT de novo methylation activity would help in resolving how DNA methylation is targeted to regions that are normally not regulated by RdDM, such as heterochromatic TEs and intra-genic sequences (gene bodies), methylation of the latter was recently genetically linked to CMT3[52].

The antagonistic CHH methylation changes in Ppcmt, from hypomethylation in heterochromatin to hypermethylation in euchromatin (FIGS. 3E-G), resembles the methylation phenotype of Arabidopsis histone h1 mutation[22]. Similar to Arabidopsis h1, the elimination of CHG methylation in Ppcmt could disturb the chromatin in a way that affected regular CHH methylation activities as well as demethylation ones[22,53]. The present data suggests that the role of H3K9me2 in targeting non-CG methylation in angiosperms[4,10] has already been established in basal plants. However, unlike many angiosperms that utilize two CMT orthologues to methylate distinct non-CG contexts, i.e. CMT2 for CHH and CMT3 for CHG, basal plants use CMT for CHG and DNMT3 for CHH sites. Similar to angiosperm-CMTs, early diverged CMTs, such as PpCMT, probably also utilize their chromodomain to be targeted to H3K9me2-chromatin. Plant DNMT3s are missing a chromodomain, thus it is likely that the association of their CHH methylation with H3K9me2 is indirect. Mammalian DNMT3s were found to bind H3K9-methylated chromatin via attachment to chromodomain proteins or via unmethylated-H3K4 residues (H3K4me0), a histone mark associated with H3K9me2[7]. The partial dependency of CHH methylation on PpCMT/CHG methylation (FIG. 3F) and the absence of the reverse effect, i.e. control of CHG methylation by DNMT3/CHH methylation (FIG. 1B), suggest a hierarchy between CHG and CHH methylation. In this hierarchy, PpCMT is positioned on the higher level, possibly by recruiting the DNMT3 protein itself or by regulating the level of DNMT3 substrates, e.g. H3K9me2 and/or H3K4me0. An alternative explanation for the CHH hypomethylation in cmt mutants (FIG. 3E), could be that PpCMT is involved in establishing CHH methylation that is subsequently maintained by PpDNMT3b. This hypothesis is supported by the ability of *Arabidopsis* CMTs to establish CHH methylation in vitro[20, 21], and by the residual of CWA methylation in Ppdnmt3b mutants (FIG. 8) that resembles the preference of some angiosperm CMTs toward such CHH subcontext[41].

TABLE 5

DNMT gene model ID and source

| DNMT group | Name | Gene Model | Taxonomic Group1 | Taxonomic Group2 | Organism | Protein Length (AA) | Source |
|---|---|---|---|---|---|---|---|
| DNMT1 | NveDNMT1 | 125496 | Animals | Cnidaria | *Nematostella vectensis* | 1263 | Metazome |
| DNMT1 | HsDNMT1 | ENSG00000130816 | Animals | Mammals | *Homo sapiens* | 1632 | Metazome |
| DNMT1 | PpMET | Pp3c11_20540 | Bryophytes | Mosses | *Physcomitrella patens* | 1579 | Phytozome |
| DNMT1 | ZmMET | GRMZM2G333916_T01 | Angiosperms | Monocots | *Zea mays* | 1536 | Phytozome |
| DNMT1 | AtMET1 | AT5G49160 | Angiosperms | Eudicots | *Arabidopsis thaliana* | 1535 | Phytozome |
| DNMT3 | NveDNMT3 | 127267 | Animals | Cnidaria | *Nematostella vectensis* | 624 | Metazome |
| DNMT3 | CiDNMT3 | 270939 | Animals | Tunicata | *Ciona intestinalis* | 618 | Metazome |
| DNMT3 | MmDNMT3a | ENSMUSP00000020991 | Animals | Mammals | *Mus musculus* | 910 | Metazome |
| DNMT3 | MmDNMT3b | ENSMUSP00000051830 | Animals | Mammals | *Mus musculus* | 860 | Metazome |
| DNMT3 | HsDNMT3a | ENSG00000119772 | Animals | Mammals | *Homo sapiens* | 914 | Metazome |
| DNMT3 | HsDNMT3b | ENSG00000088305 | Animals | Mammals | *Homo sapiens* | 853 | Metazome |
| DNMT3 | KfDNMT3 | kfl00080_0350_v1.1 | Charophytes |  | *Klebsormidium flaccidum* | 893 | K. nitens genome project |
| DNMT3 | MpDNMT3i | Mapoly0043s0021.1 | Bryophytes | Liverworts | *Marchantia polymorpha* | 654 | Phytozome |
| DNMT3 | MpDNMT3ii | Mapoly0095s0030.1 | Bryophytes | Liverworts | *Marchantia polymorpha* | 687 | Phytozome |
| DNMT3 | PpDNMT3a | Pp3c3_3540V3.1 | Bryophytes | Mosses | *Physcomitrella patens* | 736 | Phytozome |
| DNMT3 | PpDNMT3b | Pp3c13_8320V3.1 | Bryophytes | Mosses | *Physcomitrella patens* | 711 | Phytozome |
| DNMT3 | SfDNMT3i | Sphfalx0068s0040.1 | Bryophytes | Mosses | *Sphagnum fallax* | 739 | Phytozome |
| DNMT3 | SfDNMT3ii | Sphfalx0127s0004.1 | Bryophytes | Mosses | *Sphagnum fallax* | 767 | Phytozome |
| DNMT3 | SmDNMT3i | fgenesh2_pg.C_scaffold_6000551 | Lycophytes |  | *Selaginella moellendorffii* | 630 | Phytozome |
| DNMT3 | SmDNMT3ii | fgenesh2_pg.C_scaffold_17000071 | Lycophytes |  | *Selaginella moellendorffii* | 685 | Phytozome |
| DNMT3 | EbDNMT3 | GNQG-2005968 | Gymnosperms | Cycadales | *Encephalartos barteri* | 551 | 1KP |
| DNMT3 | SeDNMT3_F1 | KAWQ-2009204 | Gymnosperms | Cycadales | *Stangeriaeriopus* | 248 | 1KP |
| DNMT3 | SeDNMT3_F2 | KAWQ-2054998 | Gymnosperms | Cycadales | *Stangeriaeriopus* | 244 | 1KP |
| DNMT3 | WmDNMT3 | TOXE-2012823 | Gymnosperms | Gnetales | *Welwitschia mirabilis* | 562 | 1KP |
| DNMT3 | PtaDNMT3 | PTA00084430 | Gymnosperms | Conifers | *Pinustaeda* | 426 | PLAZA |
| DNMT3 | PsyDNMT3 | PSY00011178 | Gymnosperms | Conifers | *Pinus sylvestris* | 426 | PLAZA |

TABLE 5-continued

DNMT gene model ID and source

| DNMT group | Name | Gene Model | Taxonomic Group1 | Taxonomic Group2 | Organism | Protein Length (AA) | Source |
|---|---|---|---|---|---|---|---|
| DNMT3 | McDNMT3 | CDFR-2008757 | Gymnosperms | Conifers | Manoao colensoi | 405 | 1KP |
| DNMT3 | SaDNMT3_F1 | KLGF-2012241 | Gymnosperms | Conifers | Sundacarpus amarus | 344 | 1KP |
| DNMT3 | SaDNMT3_F2 | KLGF-2078876 | Gymnosperms | Conifers | Sundacarpus amarus | 105 | 1KP |
| DNMT3 | PjDNMT3 | MFTM-2078885 | Gymnosperms | Conifers | Pinus jeffreyi | 298 | 1KP |
| DRM | KfDRMa | kfl00018_0570_v1.1 | Charophytes | | Klebsormidium flaccidum | 697 | K. nitens genome project |
| DRM | KfDRMb | kfl00253_0110_v1.1 | Charophytes | | Klebsormidium flaccidum | 1395 | K. nitens genome project |
| DRM | MpDRMa | Mapoly0103s0053.3 | Bryophytes | Liverworts | Marchantia polymorpha | 723 | Phytozome |
| DRM | MpDRMb | Mapoly0109s0015.2 | Bryophytes | Liverworts | Marchantia polymorpha | 758 | Phytozome |
| DRM | PpDRM1 | Pp3c15_14362 | Bryophytes | Mosses | Physcomitrella patens | 1036 | Phytozome |
| DRM | PpDRM2 | Pp3c15_21430 | Bryophytes | Mosses | Physcomitrella patens | 842 | Phytozome |
| DRM | SfDRMa | Sphfalx0006s0094 | Bryophytes | Mosses | Sphagnum fallax | 551 | Phytozome |
| DRM | SfDRMb | Sphfalx0011s0183 | Bryophytes | Mosses | Sphagnum fallax | 836 | Phytozome |
| DRM | SfDRMc | Sphfalx0209s0004 | Bryophytes | Mosses | Sphagnum fallax | 790 | Phytozome |
| DRM | SmDRMa | 411110 | Lycophytes | | Selaginella moellendorffii | 566 | Phytozome |
| DRM | SmDRMb | fgenesh2_pg.C_scaffold_5000240 | Lycophytes | | Selaginella moellendorffii | 551 | Phytozome |
| DRM | GbiDRM | GBI00021934 | Gymnosperms | Ginkgoales | Ginkgo biloba | 655 | PLAZA |
| DRM | PabDRMa | PAB00006266 | Gymnosperms | Conifers | Piceaabies | 356 | PLAZA |
| DRM | PabDRMb | PAB00012689 | Gymnosperms | Conifers | Piceaabies | 482 | PLAZA |
| DRM | PabDRMc | PAB00046707 | Gymnosperms | Conifers | Piceaabies | 596 | PLAZA |
| DRM | PabDRMd | PAB00048154 | Gymnosperms | Conifers | Piceaabies | 532 | PLAZA |
| DRM | PabDRe | PAB00049465 | Gymnosperms | Conifers | Piceaabies | 398 | PLAZA |
| DRM | PpiDRMa | PPI00065449 | Gymnosperms | Conifers | Pinus pinaster | 747 | PLAZA |
| DRM | PpiDRMb | PPI00073543 | Gymnosperms | Conifers | Pinus pinaster | 423 | PLAZA |
| DRM | PsyDRMa | PSY00004978 | Gymnosperms | Conifers | Pinus sylvestris | 747 | PLAZA |
| DRM | PsyDRMb | PSY00005220 | Gymnosperms | Conifers | Pinus sylvestris | 473 | PLAZA |
| DRM | PsyDRMc | PSY00006869 | Gymnosperms | Conifers | Pinus sylvestris | 662 | PLAZA |
| DRM | PsyDRMd | PSY00008531 | Gymnosperms | Conifers | Pinus sylvestris | 645 | PLAZA |
| DRM | PtaDRMa | PTA00004821 | Gymnosperms | Conifers | Pinus taeda | 687 | PLAZA |
| DRM | PtaDRMb | PTA00013841 | Gymnosperms | Conifers | Pinus taeda | 581 | PLAZA |
| DRM | PtaDRMc | PTA00015283 | Gymnosperms | Conifers | Pinus taeda | 367 | PLAZA |
| DRM | PtaDRMd | PTA00023209 | Gymnosperms | Conifers | Pinus taeda | 461 | PLAZA |
| DRM | PtaDRMe | PTA00046027 | Gymnosperms | Conifers | Pinus taeda | 435 | PLAZA |
| DRM | PtaDRMf | PTA00067039 | Gymnosperms | Conifers | Pinus taeda | 349 | PLAZA |
| DRM | AtrDRM3 | evm_27.TU.AmTr_v1.0_scaffold00003.192 | Angiosperms | Basel Angiosperms | Amborella trichopoda | 719 | Phytozome |
| DRM | AtrDRM2 | evm_27.TU.AmTr_v1.0_scaffold00096.44 | Angiosperms | Basel Angiosperms | Amborella trichopoda | 503 | Phytozome |
| DRM | BdDRM2a | Bradi1g11420 | Angiosperms | Monocots | Brachypodium distachyon | 518 | Phytozome |

TABLE 5-continued

DNMT gene model ID and source

| DNMT group | Name | Gene Model | Taxonomic Group1 | Taxonomic Group2 | Organism | Protein Length (AA) | Source |
|---|---|---|---|---|---|---|---|
| DRM | BdDRM 2b | Bradi1g77873 | Angiosperms | Monocots | Brachypodium distachyon | 610 | Phytozome |
| DRM | BdDRM 3 | Bradi2g38577 | Angiosperms | Monocots | Brachypodium distachyon | 706 | Phytozome |
| DRM | BdDRM 2c | Bradi4g05680 | Angiosperms | Monocots | Brachypodium distachyon | 588 | Phytozome |
| DRM | PhDRM 3 | Pahal.C01225 | Angiosperms | Monocots | Panicumhallii | 660 | Phytozome |
| DRM | PhDRM 2a | Pahal.I00079 | Angiosperms | Monocots | Panicumhallii | 603 | Phytozome |
| DRM | PhDRM 2b | Pahal.I00969 | Angiosperms | Monocots | Panicumhallii | 588 | Phytozome |
| DRM | SbDRM 2a | Sobic.001G458100 | Angiosperms | Monocots | Sorghum bicolor | 577 | Phytozome |
| DRM | SbDRM 2b | Sobic.001G535800 | Angiosperms | Monocots | Sorghum bicolor | 608 | Phytozome |
| DRM | SbDRM 2c | Sobic.003G124000 | Angiosperms | Monocots | Sorghum bicolor | 609 | Phytozome |
| DRM | SbDRM 3 | Sobic.009G032200 | Angiosperms | Monocots | Sorghum bicolor | 657 | Phytozome |
| DRM | ZmDRM 3 | GRMZM2G065599 | Angiosperms | Monocots | Zea mays | 461 | Phytozome |
| DRM | ZmDRM 2a | GRMZM2G092497 | Angiosperms | Monocots | Zea mays | 604 | Phytozome |
| DRM | ZmDRM 2b | GRMZM2G137366 | Angiosperms | Monocots | Zea mays | 610 | Phytozome |
| DRM | ZorDRM 3 | Zosma21g00360.1 | Angiosperms | Monocots | Zostera marina | 597 | Phytozome |
| DRM | ZorDRM 2 | Zosma67g00380.1 | Angiosperms | Monocots | Zostera marina | 570 | Phytozome |
| DRM | AtDRM 3 | AT3G17310 | Angiosperms | Eudicots | Arabidopsis thaliana | 711 | Phytozome |
| DRM | AtDRM 2 | AT5G14620 | Angiosperms | Eudicots | Arabidopsis thaliana | 627 | Phytozome |
| DRM | AtDRM 1 | AT5G15380 | Angiosperms | Eudicots | Arabidopsis thaliana | 625 | Phytozome |
| DRM | BrDRM 2a | Brara.B00561 | Angiosperms | Eudicots | Brassica rapa | 406 | Phytozome |
| DRM | BrDRM 3b | Brara.E02454 | Angiosperms | Eudicots | Brassica rapa | 703 | Phytozome |
| DRM | BrDRM 2b | Brara.G02881 | Angiosperms | Eudicots | Brassica rapa | 599 | Phytozome |
| DRM | BrDRM 3a | Brara.I04643 | Angiosperms | Eudicots | Brassica rapa | 502 | Phytozome |
| DRM | BrDRM 2c | Brara.J02008 | Angiosperms | Eudicots | Brassica rapa | 602 | Phytozome |
| DRM | GmDRM2a | Glyma.02G035700 | Angiosperms | Eudicots | Glycine max | 538 | Phytozome |
| DRM | GmDRM2b | Glyma.05G005600 | Angiosperms | Eudicots | Glycine max | 591 | Phytozome |
| DRM | GmDRM3a | Glyma.07G233200 | Angiosperms | Eudicots | Glycine max | 695 | Phytozome |
| DRM | GmDRM3b | Glyma.17G038300 | Angiosperms | Eudicots | Glycine max | 730 | Phytozome |
| DRM | GmDRM2c | Glyma.19G006100 | Angiosperms | Eudicots | Glycine max | 581 | Phytozome |
| DRM | MeDRM 3 | Manes.03G210200 | Angiosperms | Eudicots | Manihot esculenta | 780 | Phytozome |
| DRM | MeDRM 2a | Manes.15G149300 | Angiosperms | Eudicots | Manihot esculenta | 639 | Phytozome |
| DRM | MeDRM 2b | Manes.17G113600 | Angiosperms | Eudicots | Manihot esculenta | 638 | Phytozome |
| DRM | PrpDRM 3 | Prupe.1G109800 | Angiosperms | Eudicots | Prunus persica | 718 | Phytozome |
| DRM | PrpDRM 2a | Prupe.3G287400 | Angiosperms | Eudicots | Prunus persica | 585 | Phytozome |
| DRM | PrpDRM 2b | Prupe.8G038800 | Angiosperms | Eudicots | Prunus persica | 583 | Phytozome |

TABLE 6

| | Primer Name | Sequence (5'→3') | SEQ ID NO: |
|---|---|---|---|
| Cloning | Ppdrm1 5'UTR BamHI Fw | GGATCCTGGAACGCAAAACAAGACCG | 24 |
| | Ppdrm1 5'UTR BamHI Rv | GGAGGTGGATCCAATTGTTCTTTC | 25 |
| | Ppdrm1 3'UTR SphI Fw | GCATGCTTCCCCTGGCAGAAATTTGG | 26 |
| | Ppdrm1 3'UTR NotI SphI Rv | GCATGCGGCCGCGAGCATCAAATTAGAGCTTCAGGG | 27 |
| | Ppdrm2 5'UTR BamHI Fw | GGATCCGTGGTGAACCTAGTTGTCCATTGG | 28 |
| | Ppdrm2 5'UTR BamHI Rv | GGATCCTGGCGTGTAAAGCTCACACTAA | 29 |
| | Ppdrm2 3'UTR SphI Fw | GCATGCGTTTGCCTTGCCTTGTTCCTTC | 30 |
| | Ppdrm2 3'UTR NotI SphI Rv | GCATGCGGCCGCCATCCTTTTGCAACAATCCTCC | 31 |
| | Ppdnmt3a HindIII 5'KO Fw | AAGCTTGTCGTGCTGAGTATTCAGATAATCGTAGC | 32 |
| | Ppdnmt3a HindIII 5'KO Rv | AAGCTTAATCCAACTGTTCCAATTCCGC | 33 |
| | Ppdnmt3a SphI 3'KO Fw | GCATGCTAGCTCTCTTGAAGTATCCG | 34 |
| | Ppdnmt3a 3'KO Rv | AATCGTGCTTTCTACCACATACTGCC | 35 |
| | Ppdnmt3b HindIII 5'KO Fw | AAGCTTCGGGTTTCGGAGTTCTGGGTT | 36 |
| | Ppdnmt3b HindIII 5'KO Rv | AAGCTTGCAGGCCAGAGGAAAGAGCG | 37 |
| | Ppdnmt3b SphI 3'KO Fw | GCATGCCCATGTTCCAATCTTTTGACTTGCC | 38 |
| | Ppdnmt3b 3'KO Rv | ACATTCCGTTTACCAGTAGCATCTGG | 39 |
| | KpnI Zeo Fw | GGTACCGTCAACATGGTGGAGCACGACA | 40 |
| | SphI Zeo Rv | GCATGCCAGGTCACTGGATTTTGGTTTTAGG | 41 |
| Deletion mutant screening | Ppdrm1 2240 5' Fw | GGAACACGGTGGATGTATTCCTTCT | 42 |
| | Ppdrm1 5550 3' Rv | AGGCGGTATGGTTGTGCCACC | 43 |
| | Ppdrm1 3209 e1 Fw | GGTCAAGGTCGAATCATCTCAACG | 44 |
| | Ppdrm1 3779 e1 Rv | GCGTTGGGATGTTTGGAGCA | 45 |
| | Ppdrm2 2292 5' Fw | GACAATTTCCATTCATGCGAGTTGTC | 46 |
| | Ppdrm2 5324 3' Rv | CAAGCCATGCCTATTGTTATCACTGTTC | 47 |
| | Ppdrm2 3202 e1 Fw | ATTGGCTTTGGTCTTCCTGGTCA | 48 |
| | Ppdrm2 3581 e1 Rv | TGTGGGAATTGCAGTGGCGT | 49 |
| | Ppdnmt3a 5046 Fw | GCTGCAAGCGTGAGCGATTC | 50 |
| | Ppdnmt3a 10651 Rv | GGGTTGGATATCACTAAGCTCCACC | 51 |
| | Ppdnmt3a 6377 Fw | GCTGACCAATCTAGGCATCCCG | 52 |
| | Ppdnmt3a 8427 Rv | TGGAGGGCTTGATTTAGGCAGAG | 53 |
| | Ppdnmt3b 5678 Fw | GCTGATGACTGCTTGAGCCTTCG | 54 |
| | Ppdnmt3b 10445 Rv | TCCACTCGTCTACTTCTTCTTTGAGATAGG | 55 |
| | Ppdnmt3b 7159 Fw | GGTCGGGTGAACGGCTGG | 56 |
| | Ppdnmt3b e11 Rv | AAGGCTATCCTGTCGAGTTGGCTT | 57 |
| | 35S Rv | TGGGACCACTGTCGGCAGAG | 58 |
| | 35S-Ter-R-Fw | GCCCCCGCTTAAAAATTGGT | 59 |
| Validation of RPS insertion | RPS-top-R_new | AAGTAGAGAAAGGAAAGAGAAAAGGGG | 60 |
| | 35S Rv | TGGGACCACTGTCGGCAGAG | 61 |
| Bisulfite assay | RPS-top-R_new | AAGTAGAGAAAGGAAAGAGAAAAGGGG | 62 |
| | RPS-top-F | CTGTATTTTCTCCCTTCA | 63 |

TABLE 7

BS-seq summary

Median coverage and averaged methylation levels in wild type and PpDNMT mutant genomes.
Substantial loses in methylation (>90%) are marked in bold and underlined.

| Genetic back-ground | Mapping | | | Median site coverage | Average genomic methylation levels | | | | Average organelle methylation levels | |
|---|---|---|---|---|---|---|---|---|---|---|
| | Total reads | Mapped reads | Ratio | | CG | CWG | CCG | CHH | Mitochondria | Chloroplast |
| wild type | 41145982 | 34088890 | 83% | 3 | 19.56% | 21.12% | 8.44% | 15% | 0.17% | 0.17% |
| drm1 | 41372443 | 33415124 | 81% | 3 | 20.90% | 22.26% | 9.57% | 16.24% | 0.17% | 0.17% |
| drm2 | 52331188 | 42380753 | 81% | 3 | 19.79% | 21.25% | 8.87% | 15.29% | 0.17% | 0.17% |
| drm12 | 39059321 | 31104455 | 80% | 3 | 19.43% | 21.18% | 8.84% | 15.38% | 0.17% | 0.16% |
| dnmt3a | 46395247 | 34361843 | 74% | 3 | 20.14% | 21.40% | 8.83% | 14.88% | 0.17% | 0.17% |
| dnmt3b | 46037700 | 34325065 | 75% | 3 | 19.94% | 22.79% | 10.68% | <u>0.84%</u> | 0.18% | 0.17% |
| dnmt3ab | 51456246 | 40940817 | 80% | 3 | 19.62% | 22.59% | 10.57% | <u>0.83%</u> | 0.17% | 0.16% |
| met | 48204209 | 37218804 | 77% | 3 | <u>1.28%</u> | 21.74% | <u>0.65%</u> | 15.35% | 0.17% | 0.17% |
| cmt | 47855012 | 37225542 | 78% | 3 | 20.68% | <u>0.49%</u> | <u>0.39%</u> | 15.50% | 0.17% | 0.17% |
| rdr2 | 51728794 | 40797730 | 79% | 3 | 24.80% | 25.83% | 13.20% | 17.82% | 0.53% | 0.59% |

Example 2

Expression of PpDNMT3b in Human Cells

Materials and Methods

Biological Material

HEK 293T cells were maintained in a complete medium (Dulbecco's modified Eagle medium [DMEM], Gibco, supplemented with 10% [vol/vol] fetal calf serum [FCS], 4 mM L-glutamin, 40 V/ml Penicillin, 40 mg/ml streptomycin and 5 V/ml hystatin [Biological Industries, Israel] at 37° C. and 5% $CO_2$.

PpDNMT3b open reading frame was codon-optimized for expression in human, synthesized and cloned into pCDNA3.1+N-eGFP by GENSCRIPT. For control, pCDNA3.1+N-eGFP was used. The transfection was done in 60 mm tissue culture plate with cells reaching approximately 80% confluency, using PolyJet™ reagent (SignaGen) according to manufacturer's instructions. The cells were maintained for 3 or 7 days prior to DNA extraction.

Genomic DNA was extracted using GenElute™ Mammalian Genomic DNA Miniprep Kit (Qiagen) according to the manufacturer's instructions.

Targeted Bisulfite Sequencing and Data Analysis

Bisulfite library was prepared using SureSelectXT Methyl-Seq Library Preparation Kit for targeted methylation sequencing (Agilent). Deep sequencing was performed on Illumina Hi-Seq 2000, yielding approximately 80 million 150-bp paired-end reads per sample, covering 84 Mb of the human genome.

The reads were aligned to Hg38 reference genome using Bismark v0.19.1 with Bowtie2.2.6. Methylation counting for each cytosine in CG, CHG and CHH contexts was performed with bismark_methylation_extractor.

DNA methylation of genes and transposable elements was calculated using a custom perl script. Genes and TEs were aligned at either the 5' or 3' end and average methylation for all cytosines in CG, CHG or CHH context was calculated in 50 bp sliding window within 2 kb upstream and downstream to the alignment point.

Integrative Genomics Viewer 2.4.19 was used for visualization of cytosine methylation data.

Differential Expression Analysis

RNA was extracted using RNeasy Mini Kit (Qiagen) and enriched for poly-T and processed for sequencing by the Weizmann institute sequencing unit on Hiseq2500 as SE. RNA-seq data was aligned to the human genome (version GRCh38.p13) using STAR (2.7.3a) and differential expression per gene was analyzed using DeSeq2. The human disease database was used to list diseases related to miss-regulated genes found in the analyses.

Results

As can be seen from FIGS. 11 and 12, human cells genetically modified to express PpDNMT3b show CHH hypermethylation.

PpDNMT3b differs from human DNMT3a and DNMT3b in sequence specificity as well as the ability to produce non-CG methylation in human cells which express DNMT3a and DNMT3b. Non-CG methylation is performed by DNMT3s and can be found in human embryonic stem cells and neurons. In both cell types, non-CG methylation occurs mainly in CA sequences. *Physcomitrella patens* PpDNMT3b has a similar preference, however, is more efficient in methylating CT and CC sequences while limited in methylating CHG sequences (CAG/CTG) (FIG. 13). Expression of PpDNMT3b in HEK293 cells resulted in upregulation of 14 genes, most of which belong to heat shock response genes and are involved in various human diseases (Table 8). Indeed, several of these genes had hyper non-CG methylation within their gene bodies (FIG. 14).

TABLE 8

| # | Name | Expression fold change | Type | Major Disease effect |
|---|------|------------------------|------|----------------------|
| 1 | HSPA1A | 48 | heat shock protein | Carotid Artery Occlusion and Transient Cerebral Ischemia |
| 2 | HSPH1 | 4 | heat shock protein | Aggressive B-Cell Non-Hodgkin Lymphoma and Cystic Fibrosis. |
| 3 | HSPA7 | 32 | heat shock protein | |
| 4 | HSPA6 | 35 | heat shock protein | Hepatocellular Carcinoma |
| 5 | DNAJB1 | 4 | heat shock protein | Fibrolamellar Carcinoma |
| 6 | ZFAND2A | 3 | zinc finger | |
| 7 | HSPB1 | 2 | heat shock protein | Charcot-Marie-Tooth Disease and Neuronopathy |
| 8 | HSP90AA1 | 3 | heat shock protein | Hypersensitivity Reaction Disease and Hand-Foot-Genital Syndrome. |
| 9 | CRYAB | 6 | crystallin alpha B | Cardiomyopathy and Cataract |
| 10 | SERPINH1 | 2 | serpin family | Osteogenesis Imperfecta |
| 11 | BAG3 | 2 | BCL2 associated | Myopathy, Myofibrillar and Cardiomyopathy |

TABLE 8-continued

| # | Name | Expression fold change | Type | Major Disease effect |
|---|---|---|---|---|
| 12 | CHORDC1 | 2 | cys/his rich domain | Involved in stress response. Prevents tumorigenesis |
| 13 | HSPA4L | 2 | heat shock protein | |
| 14 | ZNF79 | 2 | zinc finger | Prostate Carcinoma In Situ and Kabuki Syndrome |

Example 3

Expression of PpDNMT3b in Plant Cells

Materials and Methods

Plants

Arabidopsis ddcc (drm1 drm2 cmt2 cmt3 quadruple mutant) plants were grown in a controlled growth room under long-day photoperiod (16-h light and 8-h dark, light intensity 200 μmol photons m−2 s−1) at 22° C.±2 and 70% humidity.

Cloning pEGAD-hyg was generated by replacing the BASTA resistance cassette in pEGAD (GenBank: AF218816.1) with hygromycin resistance cassette from pcambia1300 via restriction with VspI (Thermo Fisher Scientific). In-Fusion® HD Cloning (Takara bio) was used to clone the Arabidopsis CMT3 promotor and PpDNMT3b ORF in frame with EGFP in the pEGAD-hyg vector. The final plasmid was verified by sanger sequencing.

Generation of Transgenic Mutant Lines ddcc mutant plants which have low non-CG methylation levels were used as background for PpDNMT3b expression which was introduced into plants via Agrobacterium tumefaciens-mediated transformation.

BS-Seq and Analysis

Genomic DNA was extracted from leaves using DNeasy Plant Mini Kit (Qaigen) according to manufacturer's instructions. WGBS was performed by BGI. The reads were aligned using methylpy and analyzed via python scripts.

Results

As illustrated in FIG. 15, expression of PpDNMT3b in Arabidopsis, even under the weak AtCMT3 promotor, induced genome wide hyper CHH methylation.

Example 4

Generation of pdCas9-DNMT3 Fusion Protein

Material and Methods

The human codon-optimized PpDNMT3b methyltransferase domain (MTD) DNA region was cloned in frame with dCas9 replacing HsDNMT3a-MTD in pdCas9-DNMT3A-PuroR_BACH2-sgRNA8 (Addgene plasmid #71828) by BamHI and FseI. The transfection was done in 60 mm tissue culture plate with cells reaching approximately 80% confluency, using PolyJet™ reagent (SignaGen) according to manufacturer's instructions. The cells were maintained for 7 days prior to DNA extraction.

The plasmid was transformed into HEK293 as described in Example 2. Cells were harvested 7 days following transfection. Bisulfite sequencing of the dCAS9 targeted region will be analyzed to determine methylation by the fusion protein.

Results

The DNA sequence encoding the fusion protein is set forth in SEQ ID NO: 64 and illustrated in FIG. 16.

The amino acid sequence of the fusion protein is set forth in SEQ ID NO: 65 and illustrated in FIG. 17.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

In addition, any priority documents of this application are hereby incorporated herein by reference in their entirety.

REFERENCES

1. Goll, M. G. & Bestor, T. H. Eukaryotic cytosine methyltransferases. Annu Rev Biochem 74, 481-514 (2005).
2. Feng, S. et al. Conservation and divergence of methylation patterning in plants and animals. Proc. Natl. Acad. Sci. U.S.A. 107, 8689-8694 (2010).
3. Niederhuth, C. E. et al. Widespread natural variation of DNA methylation within angiosperms. Genome Biol. 17, 194 (2016).
4. Du, J., Johnson, L. M., Jacobsen, S. E. & Patel, D. J. DNA methylation pathways and their crosstalk with histone methylation. Nat. Rev. Mol. Cell Biol. 16, 519-32 (2015).
5. Zemach, A., McDaniel, I. E., Silva, P. & Zilberman, D. Genome-Wide Evolutionary Analysis of Eukaryotic DNA Methylation. Science (80-.). 328, 916-919 (2010).
6. Cedar, H. & Bergman, Y. Programming of DNA methylation patterns. Annu. Rev. Biochem. 81, 97-117 (2012).
7. Jurkowska, R. Z. & Jeltsch, A. Enzymology of Mammalian DNA Methyltransferases. Adv. Exp. Med. Biol. 945, 87-122 (2016).
8. Feng, W. & Michaels, S. D. Accessing the Inaccessible: The Organization, Transcription, Replication, and Repair of Heterochromatin in Plants. Annu. Rev. Genet. 49, 439-459 (2015).

9. Springer, N. M., Lisch, D. & Li, Q. Creating Order from Chaos: Epigenome Dynamics in Plants with Complex Genomes. *Plant Cell* 28, 314-325 (2016).
10. Wendte, J. M. & Schmitz, R. J. Specifications of Targeting Heterochromatin Modifications in Plants. *Mol. Plant* 11, 381-387 (2018).
11. Zhang, H., Lang, Z. & Zhu, J.-K. Dynamics and function of DNA methylation in plants. *Nat. Rev. Mol. Cell Biol.* 19, 489-506 (2018).
12. Sotelo-Silveira, M., Chavez Montes, R. A., Sotelo-Silveira, J. R., Marsch-Martinez, N. & de Folter, S. Entering the Next Dimension: Plant Genomes in 3D. *Trends Plant Sci.* 23, 598-612 (2018).
13. Song, X. & Cao, X. Context and Complexity: Analyzing Methylation in Trinucleotide Sequences. *Trends Plant Sci.* 22, 351-353 (2017).
14. Seymour, D. K. & Becker, C. The causes and consequences of DNA methylome variation in plants. *Curr. Opin. Plant Biol.* 36, 56-63 (2017).
15. Liu, C. et al. Genome-wide analysis of chromatin packing in *Arabidopsis thaliana* at single-gene resolution. *Genome Res.* 26, 1057-1068 (2016).
16. Satyaki, P. R. V. & Gehring, M. DNA methylation and imprinting in plants: machinery and mechanisms. *Crit. Rev. Biochem. Mol. Biol.* 52, 163-175 (2017).
17. Quadrana, L. & Colot, V. Plant Epigenetics. *Annu. Rev. Genet.* (2016). doi:10.1146/annurev-genet-120215-035254
18. Malik, G., Dangwal, M., Kapoor, S. & Kapoor, M. Role of DNA methylation in growth and differentiation in *Physcomitrella patens* and characterization of cytosine DNA methyltransferases. *FEBS J.* 279, 4081-4094 (2012).
19. Bewick, A. J. et al. The evolution of CHROMOMETHYLASES and gene body DNA methylation in plants. *Genome Biol.* 18, 65 (2017).
20. Du, J. et al. Dual binding of chromomethylase domains to H3K9me2-containing nucleosomes directs DNA methylation in plants. *Cell* 151, 167-180 (2012).
21. Stroud, H. et al. Non-CG methylation patterns shape the epigenetic landscape in *Arabidopsis*. *Nat. Struct. Mol. Biol.* 21, 64-72 (2013).
22. Zemach, A. et al. The *Arabidopsis* nucleosome remodeler DDM1 allows DNA methyltransferases to access H1-containing heterochromatin. *Cell* 153, 193-205 (2013).
23. Huff, J. T. & Zilberman, D. Dnmt1-independent CG methylation contributes to nucleosome positioning in diverse eukaryotes. Cell 156, 1286-1297 (2014).
24. He, Y. & Ecker, J. R. Non-CG Methylation in the Human Genome. *Annu. Rev. Genomics Hum. Genet.* 16, 55-77 (2015).
25. Cao, X. et al. Conserved plant genes with similarity to mammalian de novo DNA methyltransferases. *Proc Natl Acad Sci USA* 97, 4979-4984 (2000).
26. Tamiru, M., Hardcastle, T. J. & Lewsey, M. G. Regulation of genome-wide DNA methylation by mobile small RNAs. New Phytol. 217, 540-546 (2018).
27. Matzke, M. A. & Mosher, R. A. RNA-directed DNA methylation: an epigenetic pathway of increasing complexity. *Nat. Rev.* 15, 394-408 (2014).
28. Cuerda-Gil, D. & Slotkin, R. K. Non-canonical RNA-directed DNA methylation. Nat. plants 2, 16163 (2016).
29. Underwood, C. J., Henderson, I. R. & Martienssen, R. A. Genetic and epigenetic variation of transposable elements in *Arabidopsis*. *Curr. Opin. Plant Biol.* 36, 135-141 (2017).
30. Zhou, M., Palanca, A. M. S. & Law, J. A. Locus-specific control of the de novo DNA methylation pathway in *Arabidopsis* by the CLASSY family. *Nat. Genet.* 50, 865-873 (2018).
31. Daccord, N. et al. High-quality de novo assembly of the apple genome and methylome dynamics of early fruit development. *Nat. Genet.* 49, 1099-1106 (2017).
32. Schmid, M. W. et al. Extensive epigenetic reprogramming during the life cycle of Marchantia polymorpha. *Genome Biol.* 19, 9 (2018).
33. Richards, C. L. et al. Ecological plant epigenetics: Evidence from model and non-model species, and the way forward. *Ecol. Lett.* 20, 1576-1590 (2017).
34. Anderson, S. N. et al. Subtle Perturbations of the Maize Methylome Reveal Genes and Transposons Silenced by Chromomethylase or RNA-Directed DNA Methylation Pathways. G3 (Bethesda). 8, 1921-1932 (2018).
35. Noy-Malka, C. et al. A single CMT methyltransferase homolog is involved in CHG DNA methylation and development of Physcomitrella patens. *Plant Mol. Biol.* 84, 719-35 (2014).
36. Yaari, R. et al. DNA METHYLTRANSFERASE 1 is involved in mCG and mCCG DNA methylation and is essential for sporophyte development in *Physcomitrella patens*. *Plant Mol. Biol.* 88, 387-400 (2015).
37. Gentry, M. & Meyer, P. An 11 bp region with stem formation potential is essential for de novo DNA methylation of the RPS element. *PLoS One* 8, e63652 (2013).
38. Muller, A., Marins, M., Kamisugi, Y. & Meyer, P. Analysis of hypermethylation in the RPS element suggests a signal function for short inverted repeats in de novo methylation. *Plant Mol. Biol.* 48, 383-399 (2002).
39. Singh, A., Zubko, E. & Meyer, P. Cooperative activity of DNA methyltransferases for maintenance of symmetrical and non-symmetrical cytosine methylation in *Arabidopsis thaliana*. *Plant J.* 56, 814-823 (2008).
40. Coruh, C. et al. Comprehensive Annotation of *Physcomitrella patens* Small RNA Loci Reveals That the Heterochromatic Short Interfering RNA Pathway Is Largely Conserved in Land Plants. *Plant Cell* 27, 2148-2162 (2015).
41. Gouil, Q. & Baulcombe, D. C. DNA Methylation Signatures of the Plant Chromomethyltransferases. *PLoS Genet.* 12, 1-17 (2016).
42. Lang, D. et al. The *Physcomitrella patens* chromosome-scale assembly reveals moss genome structure and evolution. *Plant J.* 93, 515-533 (2018).
43. Widiez, T. et al. The chromatin landscape of the moss *Physcomitrella patens* and its dynamics during development and drought stress. *Plant J.* 79, 67-81 (2014).
44. Cokus, S. J. et al. Shotgun bisulphite sequencing of the *Arabidopsis* genome reveals DNA methylation patterning. *Nature* 452, 215-219 (2008).
45. Huettel, B. et al. Endogenous targets of RNA-directed DNA methylation and Pol IV in *Arabidopsis*. 25, 2828-2836 (2006).
46. Zhong, X. et al. DDR complex facilitates global association of RNA polymerase V to promoters and evolutionarily young transposons. *Nat. Struct. Mol. Biol.* 19, 870-875 (2012).
47. Stroud, H., Greenberg, M. & Feng, S. Comprehensive analysis of silencing mutants reveals complex regulation of the *Arabidopsis* methylome. Cell 152, 352-364 (2013).
48. Li, Q. et al. RNA-directed DNA methylation enforces boundaries between heterochromatin and euchromatin in the maize genome. *Proc. Natl. Acad. Sci. U.S.A.* 112, 14728-33 (2015).

49. Tan, F. et al. Analysis of Chromatin Regulators Reveals Specific Features of Rice DNA Methylation Pathways. *Plant Physiol.* (2016). doi:10.1104/pp. 16.00393
50. Rensing, S. A. et al. The *Physcomitrella* genome reveals evolutionary insights into the conquest of land by plants. *Science* 319, 64-69 (2008).
51. Law, J. A. & Jacobsen, S. E. Establishing, maintaining and modifying DNA methylation patterns in plants and animals. *Nat. Rev. Genet.* 11, 204-220 (2010).
52. Bewick, A. J. et al. On the origin and evolutionary consequences of gene body DNA methylation. *Proc. Natl. Acad. Sci. U.S.A.* 113, 9111-6 (2016).
53. Frost, J. M. et al. FACT complex is required for DNA demethylation at heterochromatin during reproduction in *Arabidopsis. Proc. Natl. Acad. Sci. U.S.A.* 115, E4720-E4729 (2018).
54. Ibarra, C. A. et al. Active DNA Demethylation in Plant Companion Cells Reinforces Transposon Methylation in Gametes. Science (80-.). 337, 1360-1364 (2012).
55. Roudier, F. et al. Integrative epigenomic mapping defines four main chromatin states in *Arabidopsis. EMBO J.* 30, 1928-1938 (2011).
56. Matzke, M. A., Kanno, T. & Matzke, A. J. M. RNA-Directed DNA Methylation: The Evolution of a Complex Epigenetic Pathway in Flowering Plants. *Annu. Rev. Plant Biol.* 66, 243-267 (2015).
57. Ma, L. et al. Angiosperms Are Unique among Land Plant Lineages in the Occurrence of Key Genes in the RNA-Directed DNA Methylation (RdDM) Pathway. *Genome Biol. Evol.* 7, 2648-2662 (2015).
58. Law, J. A., Vashisht, A. A., Wohlschlegel, J. A. & Jacobsen, S. E. SHH1, a homeodomain protein required for DNA methylation, as well as RDR2, RDM4, and chromatin remodeling factors, associate with RNA polymerase IV. *PLoS Genet.* 7, e1002195 (2011).
59. Ashton, N. W. & Cove, D. J. The isolation and preliminary characterisation of auxotrophic and analogue resistant mutants of the moss, *Physcomitrella patens. Mol. Gen. Genet. MGG* 154, 87-95 (1977).
60. Nishiyama, T., Hiwatashi, Y., Sakakibara, I., Kato, M. & Hasebe, M. Tagged mutagenesis and gene-trap in the moss, *Physcomitrella patens* by shuttle mutagenesis. *DNA Res.* 7, 9-17 (2000).
61. Frank, W., Decker, E. L. & Reski, R. Molecular tools to study *Physcomitrella patens. Plant Biol. (Stuttg).* 7, 220-227 (2005).
62. Mosquna, A. et al. Regulation of stem cell maintenance by the Polycomb protein FIE has been conserved during land plant evolution. *Development* 136, 2433-2444 (2009).
63. Parsons, J. et al. Moss-based production of asialo-erythropoietin devoid of Lewis A and other plant-typical carbohydrate determinants. *Plant Biotechnol. J.* 10, 851-861 (2012).
64. Zimmer, A. D. et al. Reannotation and extended community resources for the genome of the non-seed plant *Physcomitrella patens* provide insights into the evolution of plant gene structures and functions. *BMC Genomics* 14, 498 (2013).
65. Leinonen, R., Sugawara, H., Shumway, M. & Collaboration, I. N. S. D. The sequence read archive. *Nucleic Acids Res.* 39, D19-21 (2011).
66. Johnson, M. et al. NCBI BLAST: a better web interface. *Nucleic Acids Res.* 36, W5-W9 (2008).
67. Wickett, N. J. et al. Phylotranscriptomic analysis of the origin and early diversification of land plants. *Proc. Natl. Acad. Sci. U.S.A.* 111, E4859-68 (2014).
68. Matasci, N. et al. Data access for the 1,000 Plants (1KP) project. Gigascience 3, 17 (2014).
69. Xie, Y. et al. SOAPdenovo-Trans: de novo transcriptome assembly with short RNA-Seq reads. *Bioinformatics* 30, 1660-1666 (2014).
70. Johnson, M. T. J. et al. Evaluating Methods for Isolating Total RNA and Predicting the Success of Sequencing Phylogenetically Diverse Plant Transcriptomes. *PLoS One* 7, e50226 (2012).
71. Edgar, R. C. MUSCLE: multiple sequence alignment with high accuracy and high throughput. *Nucleic Acids Res* 32, 1792-1797 (2004).
72. Hoang, D. T., Chernomor, O., von Haeseler, A., Minh, B. Q. & Vinh, L. S. UFBoot2: Improving the Ultrafast Bootstrap Approximation. *Mol. Biol. Evol.* 35, 518-522 (2018).
73. Nguyen, L.-T., Schmidt, H. A., von Haeseler, A. & Minh, B. Q. IQ-TREE: A Fast and Effective Stochastic Algorithm for Estimating Maximum-Likelihood Phylogenies. *Mol. Biol.* Evol. 32, 268-274 (2015).
74. Kalyaanamoorthy, S., Minh, B. Q., Wong, T. K. F., von Haeseler, A. & Jermiin, L. S. ModelFinder: fast model selection for accurate phylogenetic estimates. *Nat. Methods* 14, 587-589 (2017).
75. Langmead, B. & Salzberg, S. L. Fast gapped-read alignment with Bowtie 2. *Nat. Methods* 9, 357-359 (2012).

What is claimed is:

1. A mammalian cell comprising an expression vector which comprises a polynucleotide encoding a fusion protein, said fusion protein comprising a DNA targeting moiety linked to a catalytic domain of a plant DNA methyltransferase 3 (DNMT3) protein, wherein the cell comprises a gene and a regulatory sequence thereof, that has a higher methylation status at a CHH site than a methylation status at said CHH site of said gene in the absence of the fusion protein, wherein said DNMT3 is not a domain rearranged methyltransferase (DRM).

2. The cell of claim 1, wherein said DNA targeting moiety comprises a DNA endonuclease protein.

3. The cell of claim 2, wherein said DNA endonuclease protein comprises a catalytically inactive CRISPR associated 9 (dCas9) protein.

4. The cell of claim 1, wherein said plant DNMT3 protein is a gymnosperm or a bryophyte DNMT3 protein.

5. The cell of claim 1, wherein said DNMT3 methylates a target DNA of the cell at a CC site and/or a CT site to a greater extent than a human DNMT3 methylates said target DNA under identical conditions.

6. The cell of claim 1, wherein said DNMT3 additionally methylates a gene of the cell at a CpG site.

7. The cell of claim 1, being a human cell.

8. The cell of claim 1, being a non-neuronal cell or a non-embryonic stem cell.

* * * * *

SEQUENCE LISTING

```
<160> NUMBER OF SEQ ID NOS: 67

<210> SEQ ID NO 1
<211> LENGTH: 332
<212> TYPE: PRT
<213> ORGANISM: Klebsormidium flaccidum

<400> SEQUENCE: 1

Val Val Ser Met Phe Asp Gly Met Gly Gly Cys Trp Gln Ala Leu Lys
1               5                   10                  15

Ala Leu Gly Ile Pro Val Lys Lys Gly Tyr Ser Cys Glu Ile Lys Glu
            20                  25                  30

Phe Ala Asn Ala Val Val Lys Glu Arg Phe Pro Asp Val Ile His Leu
        35                  40                  45
```

```
Gly Ser Val Thr Ala Val Thr Gln Asp Met Ile Pro Glu Pro Val Asp
        50                  55                  60

Leu Ile Val Ala Gly Phe Pro Cys Gln Asp Leu Ser Ser Met Gly Asn
65                  70                  75                  80

Gln Arg Gly Leu His Gly Ala Arg Ser Gly Leu Phe Phe His Ile Pro
                85                  90                  95

Arg Phe Ile Ser Met Phe Lys Ala Lys Trp Phe Leu Val Glu Asn Val
                100                 105                 110

Lys Cys Arg Trp Gln Asp Gln Ala Glu Ile Thr Lys Tyr Leu Leu Asn
                115                 120                 125

Val Leu Pro Leu Glu Leu Asp Ala Glu Leu Ser Pro Gln Ser Arg
130                 135                 140

Val Arg Asn Tyr Trp Thr Asn Leu Pro Leu Pro Pro Asn Leu Pro Gly
145                 150                 155                 160

Ile Arg Asp Ala Pro Glu Thr Ser Val Gln His Phe Leu Glu Asn Ala
                165                 170                 175

Ile Ala Pro Phe Val Lys Thr Gly Thr Val Met Thr Thr Asn Asn Asp
                180                 185                 190

Ala Asn Thr Ser Asn Cys Ala Leu Lys Ser Ile Tyr Asp Leu Ala Ser
                195                 200                 205

Gly Gly Ala Arg Tyr Leu Glu Val Glu Glu Ile Glu Ala Met Met Gly
                210                 215                 220

Tyr Ser Ala Gly Tyr Ser Lys Ile Pro Tyr Asn Lys His Gly Cys Ile
225                 230                 235                 240

Leu Pro Phe Ser Ser Lys Lys Gln Ser Gly Arg Arg Cys Ser
                245                 250                 255

Gln Gly Gly Ala Ser Glu Gly Ala Asn Gly Gly Ala Glu Gly Pro
                260                 265                 270

Pro Gln Lys Arg Pro Gly Arg Pro Thr Pro Lys Arg Arg Ser Gln
                275                 280                 285

Ser Thr Pro Arg Arg Lys Leu Leu Ser Pro Gly Ser Ser Gly Glu Ala
                290                 295                 300

Leu Phe Ala Thr Lys Asp Leu Arg Trp Glu Leu Leu Gly Asn Ser Phe
305                 310                 315                 320

Val Val Pro Cys Ile Ala Tyr Met Leu Ser Gln Leu
                325                 330

<210> SEQ ID NO 2
<211> LENGTH: 207
<212> TYPE: PRT
<213> ORGANISM: Selaginella moellendorffii

<400> SEQUENCE: 2

Val Leu Ser Leu Phe Asp Gly Ile Gly Gly Thr Trp Ala Ala Leu Asp
1               5                   10                  15

Arg Leu Glu Val Arg Tyr Lys Gly Tyr Ser Ser Glu Ile Asn Pro Tyr
                20                  25                  30

Ala Ala Arg Val Leu Lys Ala Lys Phe Pro Asn Val Thr His Leu Gly
                35                  40                  45

Asp Val Lys Asp Ile Arg Arg Gly Asp Ile Glu Glu Ile Asp Leu
                50                  55                  60

Val Val Gly Gly Phe Pro Cys Gln Asp Leu Thr Ser Met Gly Lys Arg
65                  70                  75                  80

Asp Gly Phe Leu Val Glu Asn Val Ala Ser Met Thr Trp Ile Asp Arg
                85                  90                  95
```

Glu Glu Ile Ser Lys Tyr Leu Asn Cys Leu Pro Ile Glu Ile Asp Ser
            100                 105                 110

Gln Asp Leu Thr Ala Ser Lys Arg Lys Arg Leu Tyr Trp Thr Asn Ile
            115                 120                 125

Pro His Pro Glu Lys Leu Pro Asp Val Arg Asn His Ala Ser Asn Leu
            130                 135                 140

Leu Gln His Ala Leu Asp Asp Ala Thr Ala Leu Glu Glu Lys Ile Gly
145                 150                 155                 160

Cys Val Met Thr Cys Asn Tyr Tyr Val Gly Gly Phe Gly Gln Leu Gln
            165                 170                 175

Arg Val Phe Asp Arg Lys Asp Lys Val Leu Arg Tyr Val Thr Val Thr
            180                 185                 190

Glu Leu Glu Lys Val Thr Val Ile Ser Tyr Met Leu Ser Pro Leu
            195                 200                 205

<210> SEQ ID NO 3
<211> LENGTH: 258
<212> TYPE: PRT
<213> ORGANISM: Selaginella moellendorffii

<400> SEQUENCE: 3

Val Leu Ser Leu Phe Asp Gly Ile Gly Gly Thr Trp Ala Ala Leu Asp
1               5                   10                  15

Arg Leu Glu Val Arg Tyr Lys Gly Tyr Ser Ser Glu Ile Asn Pro Tyr
            20                  25                  30

Ala Ala Arg Val Leu Lys Ala Lys Phe Pro Asn Val Thr His Leu Gly
            35                  40                  45

Asp Val Lys Asp Ile Arg Arg Gly Asp Ile Glu Glu Ile Asp Leu
        50                  55                  60

Val Val Gly Gly Phe Pro Cys Gln Asp Leu Thr Ser Met Gly Lys Arg
65                  70                  75                  80

Asp Gly Phe Leu Val Glu Asn Val Ala Ser Met Thr Trp Ile Asp Arg
            85                  90                  95

Glu Glu Ile Ser Lys Tyr Leu Asn Cys Leu Pro Ile Glu Ile Asp Ser
            100                 105                 110

Gln Asp Leu Thr Ala Ser Lys Arg Lys Arg Leu Tyr Trp Thr Asn Ile
            115                 120                 125

Pro His Pro Glu Lys Leu Pro Asp Val Arg Asn His Ala Ser Asn Leu
            130                 135                 140

Leu Gln His Ala Leu Asp Asp Ala Thr Ala Leu Glu Glu Lys Ile Gly
145                 150                 155                 160

Cys Val Met Thr Cys Asn Tyr Tyr Val Gly Gly Phe Gly Gln Leu Gln
            165                 170                 175

Arg Val Phe Asp Arg Lys Asp Glu Val Leu Arg Tyr Val Thr Val Thr
            180                 185                 190

Glu Leu Glu Lys Val Met Gly Phe Pro Ala Gly His Thr Asp Ile Asp
            195                 200                 205

Phe Gly Asn Leu Asp Asp Phe Val Pro Phe Ala Ser Glu Gln Thr Pro
            210                 215                 220

Lys Arg Lys Cys Lys Leu Asp Asp Lys Ala Lys Thr Ile Arg Trp Asn
225                 230                 235                 240

Leu Ile Gly Asn Ser Phe Ser Val Ser Val Ile Ser Tyr Met Leu Ser
            245                 250                 255

Pro Leu

<210> SEQ ID NO 4
<211> LENGTH: 319
<212> TYPE: PRT
<213> ORGANISM: Physcomitrella patens

<400> SEQUENCE: 4

```
Val Leu Ser Leu Phe Asp Gly Leu Gly Gly Ile Trp Gln Ala Leu Thr
1               5                   10                  15

Asn Leu Gly Ile Pro Phe Ser Gly Tyr Ser Ser Glu Val Leu Ala Pro
                20                  25                  30

Ala Ile Gln Val Val Lys Ser Arg His Pro His Val Lys His Val Gly
            35                  40                  45

Asp Val Arg Lys Leu Asn Leu Ser Ala Ile Pro Glu Lys Val Asp Leu
        50                  55                  60

Val Val Gly Gly Phe Pro Cys Gln Asp Leu Ser Ile Met Gly Lys Lys
65                  70                  75                  80

Glu Gly Leu His Gly Ser Arg Ser Lys Leu Phe Phe Asp Leu Leu Arg
                85                  90                  95

Val Leu Gln Ile Phe Lys Pro Lys Trp Phe Leu Val Glu Asn Val Ala
            100                 105                 110

Ser Met Ser Trp Val Asp Arg Glu Glu Ile Thr Arg His Leu Lys Val
        115                 120                 125

Val Pro Met Glu Leu Asp Ser Gln Glu Ile Thr Ala Ser Lys Arg Arg
    130                 135                 140

Arg Leu Tyr Trp Thr Asn Ile Pro His Pro Arg Leu Pro Arg Leu
145                 150                 155                 160

Arg Asp His Pro Ser Thr Ser Leu Gln Ser Cys Leu Glu Gly Ala Leu
                165                 170                 175

Ala Leu Glu Gln Lys Cys Gly Val Val Leu Cys Asn Asn Leu Tyr Lys
            180                 185                 190

Gly Gly Gly Ala Arg Leu Glu Leu Val Leu Asp Asn Thr Ile Asn Lys
        195                 200                 205

Leu Arg Tyr Ile Lys Gln Thr Glu Ile Glu Leu Leu Met Gly Tyr Pro
    210                 215                 220

Arg Asn Tyr Thr Asn Val Val Arg Arg Thr Lys Ile Thr Glu Lys
225                 230                 235                 240

Ile Ile Lys Ala Val Arg Ile Pro Glu Lys Pro Thr Val Ala Leu Pro
                245                 250                 255

Lys Ser Ser Pro Pro Gln Thr Pro Ser Ile Arg Gln Leu Arg Lys Asn
            260                 265                 270

Arg Thr Ser Arg Thr Phe Phe Ala Pro Gln Val Trp Glu Arg Asn Pro
        275                 280                 285

Thr Arg Gln Glu Ser Leu Lys Asp Leu Asp Arg Trp Phe Leu Leu Gly
    290                 295                 300

Asn Ser Phe Ser Val Gln Val Ile Thr Tyr Leu Thr Ser Ser Leu
305                 310                 315
```

<210> SEQ ID NO 5
<211> LENGTH: 320
<212> TYPE: PRT
<213> ORGANISM: Physcomitrella patens

<400> SEQUENCE: 5

```
Val Leu Ser Leu Phe Asp Gly Leu Gly Gly Ile Trp Gln Ala Leu Thr
1               5                   10                  15
```

Lys Leu Gly Ile Pro Phe Ser Gly Tyr Ser Ser Glu Val Leu Ala Pro
            20                  25                  30

Ala Ile Gln Val Val Lys Ser Arg His Pro Arg Val Lys His Val Gly
            35                  40                  45

Asp Ile Arg Lys Leu Asn Leu Ser Ala Val Pro Glu Lys Val Asp Leu
50                      55                  60

Val Val Gly Gly Phe Pro Cys Gln Asp Leu Ser Ile Met Gly Lys Lys
65                      70                  75                  80

Glu Gly Leu His Gly Ser Arg Ser Lys Leu Phe Phe Asp Leu Leu Arg
                85                  90                  95

Val Leu Lys Val Phe Lys Pro Lys Trp Phe Leu Val Glu Asn Val Ala
            100                 105                 110

Ser Met Ser Trp Val Asp Arg Glu Ile Thr Arg His Leu Lys Val
            115                 120                 125

Ala Pro Met Glu Leu Asp Ser Gln Glu Ile Thr Ala Ser Lys Arg Arg
            130                 135                 140

Arg Leu Tyr Trp Thr Asn Ile Pro His Pro Pro Arg Leu Pro Arg Leu
145                 150                 155                 160

Arg Asp His Pro Ser Thr Ser Leu Gln Ser Cys Leu Glu Gly Ala Leu
                165                 170                 175

Ala Leu Glu Gln Lys Cys Gly Val Ile Leu Cys Ser Asn Leu Tyr Lys
            180                 185                 190

Gly Ser Thr Ala Arg Leu Glu Leu Val Leu Asp Asn Lys Thr Asn Lys
            195                 200                 205

Leu Arg Tyr Ile Lys Gln Thr Glu Val Glu Val Leu Met Gly Tyr Pro
            210                 215                 220

Lys Asp Tyr Thr Asn Val Val Ala His Glu Thr Lys Gly Arg Thr Glu
225                 230                 235                 240

Gln Ala Glu Lys Val Leu Lys Thr Pro Val Arg Ala Lys Ser Val Glu
            245                 250                 255

Pro Lys Pro Ser Ser Val Thr Pro Pro Ser Ser Arg Gln Leu Arg Lys
            260                 265                 270

Asn Arg Lys Ser Gln Thr Phe Phe Val Pro Gln Val Trp Glu Thr Lys
            275                 280                 285

Pro Thr Arg Gln Asp Ser Leu Lys Asp Ile Asp Arg Trp Phe Leu Leu
            290                 295                 300

Gly Asn Thr Phe Ser Val Gln Val Ile Ala Tyr Leu Thr Ser Pro Leu
305                 310                 315                 320

<210> SEQ ID NO 6
<211> LENGTH: 309
<212> TYPE: PRT
<213> ORGANISM: Sphagnum fallax

<400> SEQUENCE: 6

Val Leu Ser Leu Phe Asp Gly Ile Gly Gly Ile Trp Ala Ala Leu Thr
1               5                   10                  15

Arg Leu Gly Ile Pro Phe Thr Gly Tyr Ser Ser Glu Val Ser Ile Pro
            20                  25                  30

Ala Leu Glu Val Leu Lys Ala Lys Tyr Pro Glu Val His His Val Gly
            35                  40                  45

Asp Val Arg Lys Val Glu Arg Met Thr Val Ser Glu Lys Val Asp Leu
50                      55                  60

Val Val Gly Gly Phe Pro Cys Gln Asp Leu Ser Cys Met Gly Lys Arg

```
                65                  70                  75                  80
        Glu Gly Leu His Gly Gln Arg Ser Lys Leu Phe Phe Asp Leu Leu His
                            85                  90                  95

Val Leu Lys Ile Phe Asn Pro Ser Trp Phe Leu Val Glu Asn Val Ala
                           100                 105                 110

Ser Met Thr Trp Met Asp Arg Asp Glu Ile Ser Lys Tyr Leu Lys Leu
                           115                 120                 125

Gln Pro Ile Glu Leu Asp Ser Ile Glu Leu Ala Pro Ser Lys Arg Arg
                130                 135                 140

Arg Leu Tyr Trp Thr Asn Ile Pro His Pro Ala Arg Leu Pro Arg Val
        145                 150                 155                 160

Lys Asn His Pro Ser Thr Phe Val Gln Ser Cys Leu Leu Asp Gly Ile
                            165                 170                 175

Ala Leu Glu Glu Lys Thr Gly Ile Ile Leu Ser Asn Asn Ser Tyr Lys
                        180                 185                 190

Ser Asn Ser Cys Gln Met Glu Leu Val Leu Glu Asn Gly Thr Ser Glu
                        195                 200                 205

Leu Arg Tyr Leu Ser His Val Glu Leu Glu Arg Ile Met Gly Tyr Pro
                    210                 215                 220

Ser Asn His Thr Ser Leu Cys Ile Asp Glu Ala Glu Asn Asn Ser Asn
        225                 230                 235                 240

Pro Met Ile Ser Asn Val Ser Arg Tyr Val Gln Thr Ser Asn Thr Tyr
                            245                 250                 255

His Lys Lys Arg Gly Lys Ile Cys Gly Val Gly Gly Pro Thr Arg Phe
                        260                 265                 270

Cys Thr Pro Pro Ala Ser Thr Leu Gly Glu Pro Leu Lys Asp Ser Val
                    275                 280                 285

Arg Trp Ala Leu Leu Gly Asn Thr Phe Thr Val Pro Val Ile Ala Tyr
                290                 295                 300

Leu Val Ser Pro Leu
        305

<210> SEQ ID NO 7
<211> LENGTH: 299
<212> TYPE: PRT
<213> ORGANISM: Sphagnum fallax

<400> SEQUENCE: 7

Val Leu Ser Leu Phe Asp Gly Ile Gly Gly Ile Trp Ala Ala Leu Thr
        1               5                   10                  15

Arg Leu Gly Ile Pro Phe Val Gly Tyr Ser Ser Glu Val Ser Pro Pro
                        20                  25                  30

Ala Ile Gln Val Val Lys Ala Arg Tyr Pro Asp Val His His Val Gly
                    35                  40                  45

Asp Val Arg Lys Leu Asp Arg Thr Ser Phe Ser Gly Asn Val Asp Leu
                50                  55                  60

Val Val Gly Gly Phe Pro Cys Gln Asp Leu Ser Ala Met Gly Arg Arg
        65                  70                  75                  80

Glu Gly Leu His Gly Gln Arg Ser Lys Leu Phe Phe Asp Leu Leu Arg
                            85                  90                  95

Val Leu Lys Glu Phe Lys Pro Lys Trp Phe Leu Val Glu Asn Val Ala
                        100                 105                 110

Ser Met Thr Trp Ile Asp Arg Glu Glu Ile Ser Lys Tyr Leu Arg Val
                    115                 120                 125
```

-continued

Tyr Pro Ile Glu Leu Asp Ser Ile Glu Leu Thr Pro Thr Arg Arg Arg
                130                 135                 140

Arg Val Tyr Trp Thr Asn Ile Pro Tyr Pro Arg Leu Pro Arg Val
145                 150                 155                 160

Lys Asp His Pro Ser Thr Phe Val Gln Ser Cys Leu His Asn Ala Ile
                165                 170                 175

Ala Leu Glu Glu Lys Thr Gly Val Val Met Gly Phe Gly Ser Asp Lys
                180                 185                 190

Ala Asn Ser Cys Leu Leu Glu His Val Met Asp Ile Glu Thr Arg Lys
                195                 200                 205

Met Arg Gly Ile Thr Gln Ile Glu Val Glu Val Met Met Gly Tyr Pro
210                 215                 220

Pro Asn His Thr Asn Leu Leu Ile Thr Glu Ala Lys His Gln Thr Asn
225                 230                 235                 240

Ala Leu Val Gln Thr Pro Ser Lys Met Gln Thr Ser Ala Ser Lys
                245                 250                 255

Lys Lys Gln Gly Lys Ile Ser Gly Ser Arg Gly Ser Leu Ser Gln Asn
                260                 265                 270

Pro Ile Thr Pro Ala Ile Arg Trp Ala Leu Leu Gly Asn Thr Phe Thr
                275                 280                 285

Val Pro Thr Ile Gly Tyr Leu Ile Ser Pro Leu
                290                 295

<210> SEQ ID NO 8
<211> LENGTH: 300
<212> TYPE: PRT
<213> ORGANISM: Encephalartos barteri

<400> SEQUENCE: 8

Val Leu Ser Leu Phe Asp Gly Ile Gly Ala Ile Trp Ala Ala Leu Ser
1               5                   10                  15

Leu Thr Gly Ile Pro Phe Val Gly Tyr Ser Ser Glu Ile Asn Pro Tyr
                20                  25                  30

Ala Arg Gln Ile Val Lys Glu Arg Tyr Pro Asp Val Lys Cys Leu Gly
                35                  40                  45

Asp Ile Lys Asn Ile Lys Lys Gly Asp Ile Asn Asp Asn Val Asp Phe
50                  55                  60

Ile Val Gly Gly Phe Pro Cys Gln Asp Leu Ser Cys Met Gly Lys Lys
65                  70                  75                  80

Ala Gly Leu His Gly Asp Gln Ser Lys Leu Phe Phe Glu Leu Leu Arg
                85                  90                  95

Met Leu Gln Ile Phe Gln Pro Thr Trp Phe Leu Val Glu Asn Val Ala
                100                 105                 110

Ser Met Ser Trp Val Asp Arg Asp Glu Ile Ser Lys Tyr Leu Gly Cys
                115                 120                 125

Leu Pro Ile Glu Met Asp Ser Gln Asp Leu Thr Pro Thr Arg Arg Arg
                130                 135                 140

Arg Leu Phe Trp Thr Asn Ile Pro His Pro Lys Ser Leu Pro Lys Val
145                 150                 155                 160

Arg Asp Asn Leu Ser Thr Ser Leu Gln Ser Val Leu Glu Asn Ala Ile
                165                 170                 175

Ala Leu Gln Ala Lys Thr Ala Cys Val Leu Ser Ala Asn His Ser Pro
                180                 185                 190

Gly Ser Ala Gly Gln Val Gln Gln Val Leu Asp Asp Lys Glu Gly Asn
                195                 200                 205

Leu Arg Ser Ile Thr Ile Ser Glu Leu Glu Lys Ile Met Gly Phe Pro
            210                 215                 220

Pro Gly Tyr Thr Asp Phe Gln Phe Ser Phe Thr Ser Glu Thr Gln Ser
225                 230                 235                 240

Pro Lys Pro Ala Lys Thr Trp Ser Pro Asn Ser Pro Gly Lys Ser Glu
            245                 250                 255

Lys Pro Ile Lys Leu Ser Asp Pro Asp Gly Ser Ala Ile Thr Thr Glu
            260                 265                 270

Lys Val Thr Lys Tyr Asn Ile Arg Trp Arg Leu Leu Gly Asn Thr Phe
            275                 280                 285

Ser Val Lys Val Ile Val Tyr Leu Leu Ser Ser Leu
            290                 295                 300

<210> SEQ ID NO 9
<211> LENGTH: 215
<212> TYPE: PRT
<213> ORGANISM: Welwitschia mirabilis

<400> SEQUENCE: 9

Val Leu Ser Leu Phe Asp Gly Ile Gly Ala Ile Trp Glu Ala Leu Thr
1               5                   10                  15

Ile Leu Gly Ile Pro Phe Val Gly Tyr Ser Ser Glu Ile Asp Pro Cys
            20                  25                  30

Ala Ile Gln Val Val Lys Glu Arg Tyr Pro Lys Val Lys His Val Gly
        35                  40                  45

Asp Val Lys Asn Leu Lys Thr Glu Asp Ile Lys Glu Lys Val Asp Leu
    50                  55                  60

Leu Val Gly Gly Phe Pro Cys Gln Asp Leu Ser Ser Met Gly Arg Lys
65                  70                  75                  80

Val Gly Leu His Gly Glu Arg Ser Lys Leu Phe Phe Asp Leu Leu Gln
                85                  90                  95

Ala Met Gln Met Phe Glu Pro Tyr Trp Phe Leu Val Glu Asn Val Ala
            100                 105                 110

Ser Met Ser Trp Val Asp Arg Asp Glu Ile Cys Lys Tyr Ile Ala Cys
        115                 120                 125

Leu Pro Ile Glu Leu Asp Ser Gln Asp Leu Thr Pro Gly Lys Arg Arg
    130                 135                 140

Arg Leu Tyr Trp Thr Asn Ile Pro Phe Pro Glu Thr Leu Pro Asn Val
145                 150                 155                 160

Arg Asp Asn Ser Ser Thr Ser Leu Gln Ser Val Leu Glu Asn Ala Thr
                165                 170                 175

Ala Leu Gln Thr Lys Thr Lys Cys Ile Met Ser Ser Ser Lys Ile
            180                 185                 190

Gly Lys Met Gly Ser Phe Gln Gln Val Leu Asn Asn Asn Asp Gly Thr
        195                 200                 205

Leu Arg Asp Val Ser Val Thr
    210                 215

<210> SEQ ID NO 10
<211> LENGTH: 297
<212> TYPE: PRT
<213> ORGANISM: Marchantia polymorpha

<400> SEQUENCE: 10

Phe Val Gly Tyr Ser Cys Glu Val Asn Asp Ala Ala Met Gln Val Ile
1               5                   10                  15

```
Lys His Arg Tyr Gly Met Val Arg His Leu Gly Asp Val Lys Glu Leu
             20                  25                  30

Glu Lys Ala Asp Ile Pro Glu Lys Val Asp Leu Ile Ile Gly Gly Phe
             35                  40                  45

Pro Cys Gln Asp Leu Ser Ser Leu Gly His Lys Met Gly Leu His Gly
 50                  55                  60

Gln Arg Ser Lys Leu Phe Phe Glu Met Leu Arg Ile Ile Lys Ile Phe
 65                  70                  75                  80

Asn Pro Thr Trp Phe Leu Ala Glu Asn Val Ala Ser Met Thr Trp Ile
                 85                  90                  95

Asp Arg Gln Glu Ile Ser Lys His Leu Asn Thr Thr Pro Ile Glu Ile
                100                 105                 110

Asp Ala Glu Glu Ile Thr Pro Ser Lys Arg Arg Ile Tyr Trp Ser
                115                 120                 125

Asn Ile Pro Tyr Pro Asn Lys Ile Pro Arg Ile Arg Asp His Glu Ser
    130                 135                 140

Thr Ala Leu Gln Ser Val Leu His Asn Ala Thr Ala Leu Asp Lys Lys
145                 150                 155                 160

Val Gly Cys Ile Leu Ser Gln Asn Asn His Lys Ala Gly Tyr Gly Ser
                    165                 170                 175

Leu Glu Leu Val Met Asp Asn Asn Thr Asn Lys Leu Arg Tyr Ile Ser
                180                 185                 190

Val Ile Glu Thr Glu Leu Ala Met Gly Tyr Pro Pro Gly Tyr Thr Asn
                195                 200                 205

Val Lys Phe Asn His Ser Cys Glu Lys Lys Thr Ile Ser Ser Thr Ala
    210                 215                 220

Asn Tyr Arg Thr Glu Val Asn Ile Thr Asn Ile Thr Arg Arg Ala Gly
225                 230                 235                 240

Glu Lys Met Leu Arg Ser Lys Arg Ile Val Gln Ser Ser Gln Arg Leu
                    245                 250                 255

Val Glu Glu Met Ser Ser Val Lys Ser Ser Ser Phe Ala Asp Gly Ile
                260                 265                 270

Asn Arg Ser Ala Arg Trp His Leu Leu Gly Asn Thr Phe Ser Val Pro
                275                 280                 285

Val Ile Cys Tyr Leu Leu Ser Pro Leu
    290                 295

<210> SEQ ID NO 11
<211> LENGTH: 280
<212> TYPE: PRT
<213> ORGANISM: Marchantia polymorpha

<400> SEQUENCE: 11

Val Leu Ser Leu Phe Asp Gly Ile Gly Gly Val Trp Ala Ala Leu Glu
1                5                  10                  15

Asn Leu Gly Ile Pro Phe Ile Gly Tyr Ser Cys Glu Val Asn Ala Asp
                 20                  25                  30

Ala Met Lys Val Thr Gln Arg Asn Tyr Cys Ser Val Arg His Leu Gly
             35                  40                  45

Asp Ile His Arg Leu Lys Lys Ala Asp Ile Lys Glu Lys Ile Asp Leu
     50                  55                  60

Val Val Gly Gly Phe Pro Cys Gln Asp Leu Ser Ser Met Gly Ala Arg
 65                  70                  75                  80

Leu Gly Leu His Gly Ser Arg Ser Arg Leu Phe Phe Glu Met Leu Arg
```

```
            85                  90                  95
Val Ile Lys Thr Phe Ser Pro Thr Trp Phe Leu Ala Glu Asn Val Ala
            100                 105                 110

Ser Met Ser Trp Val Asp Arg Glu Glu Ile Ser Lys His Leu Ser Thr
            115                 120                 125

Thr Pro Leu Glu Ile Asp Ser Gln Asn Phe Ser Pro Cys Lys Arg Arg
            130                 135                 140

Arg Leu Tyr Trp Ser Asn Ile Pro Tyr Pro Lys Thr Cys Pro Arg Ile
145                 150                 155                 160

Gly Asp Asn Glu Ala Thr Ser Ile Gln Ser Val Val Gln Gly Gly Ala
                165                 170                 175

Ser Leu Ala Lys Lys Asn Met Cys Val Leu Ser Ser Asn Gly Leu Gln
                180                 185                 190

Gly Ala Thr Lys Ala Leu Met Glu Leu Val Tyr Asp Phe Arg Ile Asp
                195                 200                 205

Lys Pro Arg Tyr Ile Asn Val Val Glu Val Glu Gln Met Met Gly Tyr
            210                 215                 220

Pro Pro His Tyr Thr Asn Val Lys Phe Asp Asp Gln Lys Pro Lys Ala
225                 230                 235                 240

Lys Ile Gln Arg Arg Glu Thr Glu Ile Lys Glu Gly Gly Val Asp
                245                 250                 255

Arg Asn Thr Arg Trp Arg Leu Leu Gly Asn Ser Phe Ser Val Pro Val
                260                 265                 270

Ile Ser Phe Leu Leu Ser Pro Leu
            275                 280

<210> SEQ ID NO 12
<211> LENGTH: 893
<212> TYPE: PRT
<213> ORGANISM: Klebsormidium flaccidum

<400> SEQUENCE: 12

Met Asp Gln Glu Ala Arg Trp Arg Ala Gly Trp Arg Pro His Glu Glu
1               5                   10                  15

Phe Val Asn Ile Pro Leu Arg Thr Asp Trp Leu Ser Glu Leu Arg Arg
                20                  25                  30

Gln His Pro Trp Lys Gly Asp Gly Leu Val Val Ser Met Phe Asp
            35                  40                  45

Gly Met Gly Gly Cys Trp Gln Ala Leu Lys Ala Leu Gly Ile Pro Val
    50                  55                  60

Lys Lys Gly Tyr Ser Cys Glu Ile Lys Glu Phe Ala Asn Ala Val Val
65                  70                  75                  80

Lys Glu Arg Phe Pro Asp Val Ile His Leu Gly Ser Val Thr Ala Val
                85                  90                  95

Thr Gln Asp Met Ile Pro Glu Pro Val Asp Leu Ile Val Ala Gly Phe
            100                 105                 110

Pro Cys Gln Asp Leu Ser Ser Met Gly Asn Gln Arg Gly Leu His Gly
            115                 120                 125

Ala Arg Ser Gly Leu Phe Phe His Ile Pro Arg Phe Ile Ser Met Phe
    130                 135                 140

Lys Ala Lys Trp Phe Leu Val Glu Asn Val Lys Cys Arg Trp Gln Asp
145                 150                 155                 160

Gln Ala Glu Ile Thr Lys Tyr Leu Leu Asn Val Leu Pro Leu Glu Leu
                165                 170                 175
```

```
Asp Ala Glu Glu Leu Ser Pro Gln Ser Arg Val Arg Asn Tyr Trp Thr
            180                 185                 190
Asn Leu Pro Leu Pro Pro Asn Leu Pro Gly Ile Arg Asp Ala Pro Glu
        195                 200                 205
Thr Ser Val Gln His Phe Leu Glu Asn Ala Ile Ala Pro Phe Val Lys
    210                 215                 220
Thr Gly Thr Val Met Thr Thr Asn Asn Asp Ala Asn Thr Ser Asn Cys
225                 230                 235                 240
Ala Leu Lys Ser Ile Tyr Asp Leu Ala Ser Gly Gly Ala Arg Tyr Leu
                245                 250                 255
Glu Val Glu Glu Ile Glu Ala Met Met Gly Tyr Ser Ala Gly Tyr Ser
            260                 265                 270
Lys Ile Pro Tyr Asn Lys His Gly Cys Ile Leu Pro Phe Ser Ser Ser
        275                 280                 285
Lys Lys Gln Ser Gly Arg Arg Arg Cys Ser Gln Gly Gly Ala Ser Glu
    290                 295                 300
Gly Ala Asn Gly Gly Ala Glu Gly Pro Pro Gln Lys Arg Leu Lys
305                 310                 315                 320
Phe Glu Glu Gly Gly Ala Ser Gly Thr Glu Ala Gly Ala Glu Lys Glu
                325                 330                 335
Ala Glu Cys Asp Gly Ala Gln Val Gly Lys Glu Glu Pro Thr Gly Asp
            340                 345                 350
Glu Leu Gly Lys Gly Ile Ile Ala Leu Ser Ser Asp Glu Asp Val
        355                 360                 365
Val Phe Gln Gly Glu Ala Ala Val Glu Glu Gly Glu Asp Leu Pro
    370                 375                 380
Gly Gly His Ser Ala Glu Gly Asp Val Gly Ala Asn Glu Pro Pro Gly
385                 390                 395                 400
Lys Ser Ala Leu Pro Leu Thr Trp Leu Gly Met Gly Ala Gln Gly Gly
                405                 410                 415
Pro Asp Glu Ala Gly Ser Ser Gly Leu Ser Asn Glu Glu Lys Ser Val
            420                 425                 430
Gly Gly Gly Glu Lys Ser Pro Gly Tyr Gly Leu Arg Ala Arg Lys Pro
        435                 440                 445
Val Asn Tyr Ala Ala Glu His Val Glu Ile Asp Asp Val Ser Pro Gly
    450                 455                 460
Arg Arg Pro Thr Pro Lys Arg Arg Ser Gln Ser Thr Pro Arg Arg Lys
465                 470                 475                 480
Leu Leu Ser Pro Gly Ser Ser Gly Glu Ala Leu Phe Ala Thr Lys Asp
                485                 490                 495
Leu Arg Trp Glu Leu Leu Gly Asn Ser Phe Val Val Pro Cys Ile Ala
            500                 505                 510
Tyr Met Leu Ser Gln Leu Leu Ser Pro Gln Leu Arg Ala Arg Ala Gln
        515                 520                 525
Arg Ile Met Ala Ile Pro Thr Pro Asp Val Lys Asp Ala Cys Leu Phe
    530                 535                 540
Lys Glu Gly Glu Val Trp Ala Leu Tyr Asn Glu Asp Met Ala Pro Asn
545                 550                 555                 560
Trp Tyr Ala Cys Val Thr His Val Asp Val Thr Gln Pro Asp Trp Asp
                565                 570                 575
Gly Arg Lys Lys Leu Pro Thr Gln Phe Gly Val His Tyr Arg Phe Tyr
            580                 585                 590
Glu Tyr Leu Pro Ser Ser Glu Asn Pro Lys Ser Pro Ile Gln Gly Val
```

-continued

Gly Ile Leu Lys Leu Ala Cys Glu Asp Tyr Thr Ser Val Asp Lys Ala
            610                 615                 620

Phe Ser His Arg Val Asn Pro Ala His Leu Glu Gly Gly Arg Ile Leu
625                 630                 635                 640

Val Tyr Pro Arg Gly Glu Val Trp Val Lys Asp Arg Leu Arg
            645                 650                 655

Lys Phe Gly Arg Phe Lys Leu His Val Tyr Ile Val Lys Ser Thr Ala
            660                 665                 670

Asp Pro Leu Thr Gly Gln Phe Glu Cys Thr Ile Arg Ile Leu Val Ser
            675                 680                 685

Gln Pro Arg Ser Thr Ser Lys Thr Pro Ile Tyr Arg Met Ala Gly Gly
            690                 695                 700

Glu Arg Val Leu Ser Gly Gly Arg Thr Val Phe Ser Tyr Gln Val Pro
705                 710                 715                 720

Tyr Phe Phe Lys Asn Glu Ala Gly Leu Phe Tyr Val Glu Pro Gln Tyr
                    725                 730                 735

Asp Gln Thr Val Ala Met Arg Arg Arg Leu Leu Glu Trp Asp Asp
            740                 745                 750

Asp Glu Asp Asp Val Ala Ala Glu Glu Glu Leu Gly Arg Gly Glu
            755                 760                 765

Glu Val Leu Glu Pro Glu Ala Glu Tyr Pro Ala Ser Phe Pro Glu Thr
770                 775                 780

Glu Ser Ala Gln Lys Leu Pro Thr Leu Ala Glu Tyr Ala Pro Thr Ser
785                 790                 795                 800

Gln Ala Leu Gln Leu Val Ala Pro Asp Ala Lys Leu Pro Gln Leu Asn
                    805                 810                 815

Ala Leu Glu Asp Gln Asn Gly Gly Pro Ala Gln Ser Ser Ala Gln Ala
            820                 825                 830

Pro Ala Ile Glu Gln Ala Leu Ala Ser Arg Lys Gly Lys Glu Lys Ile
            835                 840                 845

Asp Val Ser Asp Ser Lys Ala Gln Ala Asp Asp Val Ala Gly Val Leu
            850                 855                 860

Pro Ser Glu Gly Arg Gly Leu Leu Glu Glu Arg Thr Val Leu Lys Cys
865                 870                 875                 880

Arg Asp Ile His Val Leu Met Asp Leu Leu Pro Arg Leu
                    885                 890

<210> SEQ ID NO 13
<211> LENGTH: 630
<212> TYPE: PRT
<213> ORGANISM: Selaginella moellendorffii

<400> SEQUENCE: 13

Met Glu Glu Leu Leu Ala Lys Ile Arg Glu Ala Glu Ala Leu Ala Leu
1               5                   10                  15

Arg Leu Lys Glu Ser Glu Leu Lys Lys Ile Lys Lys Pro Pro
            20                  25                  30

Pro Thr Thr Lys Glu Lys Glu Glu Phe Pro Glu His Gly Asp Trp Leu
            35                  40                  45

Asp Ala Phe Arg Arg Asn Leu Gly Ala Leu Asp Arg Arg Leu Val Val
            50                  55                  60

Leu Ser Leu Phe Asp Gly Ile Gly Gly Thr Trp Ala Ala Leu Asp Arg
65                  70                  75                  80

-continued

```
Leu Glu Val Arg Tyr Lys Gly Tyr Ser Ser Glu Ile Asn Pro Tyr Ala
                85                  90                  95
Ala Arg Val Leu Lys Ala Lys Phe Pro Asn Val Thr His Leu Gly Asp
            100                 105                 110
Val Lys Asp Ile Arg Arg Gly Asp Ile Glu Glu Ile Asp Leu Val
            115                 120                 125
Val Gly Gly Phe Pro Cys Gln Asp Leu Thr Ser Met Gly Lys Arg Asp
130                 135                 140
Gly Phe Leu Val Glu Asn Val Ala Ser Met Thr Trp Ile Asp Arg Glu
145                 150                 155                 160
Glu Ile Ser Lys Tyr Leu Asn Cys Leu Pro Ile Glu Ile Asp Ser Gln
                165                 170                 175
Asp Leu Thr Ala Ser Lys Arg Lys Arg Leu Tyr Trp Thr Asn Ile Pro
            180                 185                 190
His Pro Glu Lys Leu Pro Asp Val Arg Asn His Ala Ser Asn Leu Leu
            195                 200                 205
Gln His Ala Leu Asp Asp Ala Thr Ala Leu Glu Lys Ile Gly Cys
        210                 215                 220
Val Met Thr Cys Asn Tyr Tyr Val Gly Gly Phe Gly Gln Leu Gln Arg
225                 230                 235                 240
Val Phe Asp Arg Lys Asp Lys Val Leu Arg Tyr Val Thr Val Thr Glu
                245                 250                 255
Leu Glu Lys Val Thr Val Ile Ser Tyr Met Leu Ser Pro Leu Met Leu
                260                 265                 270
Pro Ser Thr Trp Glu Ala His Val Ile Tyr Asn Phe Ser Pro Lys Phe
            275                 280                 285
Arg Glu Ser Glu Cys Ala Val Leu Glu Thr Gly Glu Leu Trp Ala Leu
            290                 295                 300
Tyr Asn Thr Arg Ser Gln Pro Ser Trp Tyr Ala Val Ile Leu Ser Arg
305                 310                 315                 320
Ser Gly Asp Arg Phe Asp Thr Leu Gln Ser Lys Lys Lys Lys Gly
                325                 330                 335
Leu Gln Ile His Val Cys Phe Leu Glu Leu Asp Thr Gly Phe Leu Ala
            340                 345                 350
Ala Asn Asp Asp Gln Trp Ser Pro Leu Arg Gly Thr Gly Gln Tyr Asn
        355                 360                 365
Arg Ile Asp Lys Ala Asp Leu Gln Thr Ser Trp Val Thr Phe Ser His
            370                 375                 380
Arg Met Thr Thr Phe Lys Lys Leu Gly Asp Ser Tyr Phe Ile Tyr Pro
385                 390                 395                 400
Gly Glu Asn Glu Val Trp Ala Val Phe Asp Arg Asp Ser Ser Arg Pro
                405                 410                 415
Thr Leu Tyr Tyr Val Leu Val Leu Thr Thr Glu Ile Asp Trp Asn Leu
                420                 425                 430
Val Thr Arg Thr Pro Ser Gly Val Glu Gly Phe Ala Ser Arg Cys Arg
            435                 440                 445
Leu Leu Gln Gln Thr Ser Ala Ser Asp Ile Phe Arg Leu Thr Asp Thr
        450                 455                 460
Glu Val Ala Phe Lys Asp Leu Ala Gln Phe Cys Phe Lys Val Pro Tyr
465                 470                 475                 480
Tyr Phe Lys Gly Glu Gly Ser Val Phe Lys Leu Glu Leu Ser Lys Thr
                485                 490                 495
Gly Lys Tyr Leu Asn His Lys Val Gly Arg Lys Arg Arg Lys Lys
```

```
            500                 505                 510
Gly Gly Ser Asp Gly Glu Glu Asp Glu Ser Glu Ser Asp Glu Met
            515                 520                 525

Glu Glu Gln Glu Gln Gly Ser Phe Thr Pro Leu Leu Asp Arg Val Leu
    530                 535                 540

Val Glu Lys Leu Val Pro Pro Ala Lys Ser Val Gly Val Leu Leu
545                 550                 555                 560

Pro Glu Thr Gln Lys His Ile Asn Gly Gly Thr Val Val Ala Val Gly
                565                 570                 575

Gln Gly Val Tyr Asn Ser Asp Gly Glu Ile Val Pro Asn Leu Cys Lys
            580                 585                 590

Val Gly Asp Lys Val Leu Leu Pro Asp Trp Gly Val Glu Ile Lys
        595                 600                 605

Leu Glu Asp Lys Ser Tyr Glu Val Phe Arg Asp Lys Ser Ile Leu Ala
            610                 615                 620

Ile Met Ser Asp Phe Glu
625                 630

<210> SEQ ID NO 14
<211> LENGTH: 685
<212> TYPE: PRT
<213> ORGANISM: Selaginella moellendorffii

<400> SEQUENCE: 14

Met Glu Glu Leu Val Ala Lys Ile Arg Glu Ala Glu Ala Leu Ala Leu
1               5                   10                  15

Arg Leu Lys Glu Arg Glu Leu Lys Lys Glu Ile Lys Lys Pro Pro Pro
            20                  25                  30

Pro Thr Ser Lys Lys Lys Glu Glu Phe Pro Glu His Gly Asp Trp Leu
        35                  40                  45

Asp Ala Phe Arg Arg Asn Leu Gly Ala Leu Asp Arg Arg Leu Val Val
    50                  55                  60

Leu Ser Leu Phe Asp Gly Ile Gly Gly Thr Trp Ala Ala Leu Asp Arg
65                  70                  75                  80

Leu Glu Val Arg Tyr Lys Gly Tyr Ser Ser Ile Asn Pro Tyr Ala
                85                  90                  95

Ala Arg Val Leu Lys Ala Lys Phe Pro Asn Val Thr His Leu Gly Asp
            100                 105                 110

Val Lys Asp Ile Arg Arg Gly Asp Ile Glu Glu Ile Asp Leu Val
        115                 120                 125

Val Gly Gly Phe Pro Cys Gln Asp Leu Thr Ser Met Gly Lys Arg Asp
    130                 135                 140

Gly Phe Leu Val Glu Asn Val Ala Ser Met Thr Trp Ile Asp Arg Glu
145                 150                 155                 160

Glu Ile Ser Lys Tyr Leu Asn Cys Leu Pro Ile Glu Ile Asp Ser Gln
                165                 170                 175

Asp Leu Thr Ala Ser Lys Arg Lys Arg Leu Tyr Trp Thr Asn Ile Pro
            180                 185                 190

His Pro Glu Lys Leu Pro Asp Val Arg Asn His Ala Ser Asn Leu Leu
        195                 200                 205

Gln His Ala Leu Asp Asp Ala Thr Ala Leu Glu Glu Lys Ile Gly Cys
    210                 215                 220

Val Met Thr Cys Asn Tyr Tyr Val Gly Gly Phe Gly Gln Leu Gln Arg
225                 230                 235                 240
```

-continued

```
Val Phe Asp Arg Lys Asp Glu Val Leu Arg Tyr Val Thr Val Thr Glu
            245                 250                 255
Leu Glu Lys Val Met Gly Phe Pro Ala Gly His Thr Asp Ile Asp Phe
        260                 265                 270
Gly Asn Leu Asp Asp Phe Val Pro Phe Ala Ser Glu Gln Thr Pro Lys
        275                 280                 285
Arg Lys Cys Lys Leu Asp Asp Lys Ala Lys Thr Ile Arg Trp Asn Leu
    290                 295                 300
Ile Gly Asn Ser Phe Ser Val Ser Val Ile Ser Tyr Met Leu Ser Pro
305                 310                 315                 320
Leu Met Leu Pro Ser Thr Trp Glu Ala His Val Ile Tyr Asn Phe Ser
                325                 330                 335
Pro Lys Phe Arg Glu Ser Glu Cys Ala Val Leu Glu Thr Gly Glu Leu
            340                 345                 350
Trp Ala Leu Tyr Asn Thr Arg Ser Gln Pro Ser Trp Tyr Ala Val Ile
        355                 360                 365
Leu Ser Arg Ser Gly Asp Arg Phe Asp Thr Leu Gln Ser Lys Lys Lys
    370                 375                 380
Lys Lys Gly Leu Gln Ile His Val Cys Phe Leu Glu Leu Asp Thr Gly
385                 390                 395                 400
Phe Leu Ala Ala Asn Asp Asp Gln Trp Ser Pro Ile Arg Gly Thr Gly
                405                 410                 415
Gln Tyr Asn Arg Ile Asp Lys Ala Asp Leu Gln Thr Ser Trp Val Thr
            420                 425                 430
Phe Ser His Arg Met Thr Thr Phe Lys Lys Leu Gly Asp Ser Tyr Phe
        435                 440                 445
Ile Tyr Pro Gly Glu Asn Glu Val Trp Ala Val Phe Asp Arg Asp Ser
    450                 455                 460
Ser Arg Pro Thr Leu Tyr Tyr Val Leu Val Leu Thr Thr Glu Ile Asp
465                 470                 475                 480
Trp Asn Leu Val Thr Arg Thr Pro Ser Gly Val Glu Gly Phe Ala Ser
                485                 490                 495
Arg Cys Arg Leu Leu Gln Gln Thr Ser Ala Ser Asp Ile Phe Ser Phe
            500                 505                 510
Ala Arg Arg Leu Thr Gly Thr Glu Val Ala Phe Lys Asp Leu Ala Gln
        515                 520                 525
Phe Cys Phe Lys Val Pro Tyr Tyr Phe Lys Gly Glu Gly Ser Val Phe
    530                 535                 540
Lys Leu Glu Leu Ser Lys Thr Gly Lys Tyr Leu Asn His Lys Val Gly
545                 550                 555                 560
Arg Lys Arg Arg Lys Lys Gly Gly Ser Asp Glu Glu Glu Asp
                565                 570                 575
Glu Ser Glu Ser Asp Glu Met Glu Glu Gln Glu Gln Gly Ser Phe Thr
            580                 585                 590
Pro Leu Leu Asp Arg Val Leu Val Glu Lys Leu Val Pro Pro Ala Lys
        595                 600                 605
Ser Val Gly Gly Val Leu Leu Pro Glu Thr Gln Lys His Ile Asn Ala
    610                 615                 620
Gly Thr Val Val Ala Val Gly Gln Gly Val Tyr Asn Thr Asp Gly Glu
625                 630                 635                 640
Ile Val Pro Asn Leu Cys Lys Val Gly Asp Lys Val Leu Leu Pro Asp
                645                 650                 655
Trp Gly Gly Val Glu Ile Lys Leu Glu Asp Lys Ser Tyr Glu Val Phe
```

```
                    660                 665                 670
Arg Asp Lys Ser Ile Leu Ala Ile Met Ser Asp Phe Glu
        675                 680                 685

<210> SEQ ID NO 15
<211> LENGTH: 736
<212> TYPE: PRT
<213> ORGANISM: Sphagnum fallax

<400> SEQUENCE: 15

Met Asp Thr Phe Leu Ala Lys Ile Glu Glu Leu Lys Arg Glu Ala Glu
1               5                   10                  15

Arg Leu Lys His Thr Cys Arg Cys Val Ser Thr Thr Pro Thr Gly Ile
            20                  25                  30

Asn Lys Lys Thr Lys Arg Asn Ile Ile Ser Tyr Asn Asn Asp Asn Asn
        35                  40                  45

Gly Ile Ile Ala Ser Pro Gly Gly Leu Phe Ser Asn Gly Ile Thr Ser
    50                  55                  60

Ser Pro Cys Asn Ile Pro Gly Tyr Lys Leu Asp Phe Glu Gly Pro Gly
65                  70                  75                  80

Gly Asp Gly Asp Trp Val Thr Ala Phe Lys Ala Asp Ala Gly Pro Trp
                85                  90                  95

Ser Gly Glu Arg Leu Val Val Leu Ser Leu Phe Asp Gly Leu Gly Gly
            100                 105                 110

Ile Trp Gln Ala Leu Thr Asn Leu Gly Ile Pro Phe Ser Gly Tyr Ser
        115                 120                 125

Ser Glu Val Leu Ala Pro Ala Ile Gln Val Val Lys Ser Arg His Pro
    130                 135                 140

His Val Lys His Val Gly Asp Val Arg Lys Leu Asn Leu Ser Ala Ile
145                 150                 155                 160

Pro Glu Lys Val Asp Leu Val Val Gly Gly Phe Pro Cys Gln Asp Leu
                165                 170                 175

Ser Ile Met Gly Lys Lys Glu Gly Leu His Gly Ser Arg Ser Lys Leu
            180                 185                 190

Phe Phe Asp Leu Leu Arg Val Leu Gln Ile Phe Lys Pro Lys Trp Phe
        195                 200                 205

Leu Val Glu Asn Val Ala Ser Met Ser Trp Val Asp Arg Glu Glu Ile
    210                 215                 220

Thr Arg His Leu Lys Val Val Pro Met Glu Leu Asp Ser Gln Glu Ile
225                 230                 235                 240

Thr Ala Ser Lys Arg Arg Arg Leu Tyr Trp Thr Asn Ile Pro His Pro
                245                 250                 255

Pro Arg Leu Pro Arg Leu Arg Asp His Pro Ser Thr Ser Leu Gln Ser
            260                 265                 270

Cys Leu Glu Gly Ala Leu Ala Leu Glu Gln Lys Cys Gly Val Val Leu
        275                 280                 285

Cys Asn Asn Leu Tyr Lys Gly Gly Ala Arg Leu Glu Leu Val Leu
    290                 295                 300

Asp Asn Thr Ile Asn Lys Leu Arg Tyr Ile Lys Gln Thr Glu Ile Glu
305                 310                 315                 320

Leu Leu Met Gly Tyr Pro Arg Asn Tyr Thr Asn Val Val Arg Arg
                325                 330                 335

Thr Lys Ile Thr Glu Lys Ile Ile Lys Ala Val Arg Ile Pro Glu Lys
            340                 345                 350
```

Pro Thr Val Ala Leu Pro Lys Ser Pro Gln Thr Pro Ser Ile
             355                 360                 365

Arg Gln Leu Arg Lys Asn Arg Thr Ser Arg Thr Phe Phe Ala Pro Gln
370                 375                 380

Val Trp Glu Arg Asn Pro Thr Arg Gln Glu Ser Leu Lys Asp Leu Asp
385                 390                 395                 400

Arg Trp Phe Leu Leu Gly Asn Ser Phe Ser Val Gln Val Ile Thr Tyr
                405                 410                 415

Leu Thr Ser Ser Leu Leu Lys Ser Glu Val Arg Phe His Gly Lys Ala
            420                 425                 430

Val Asn Ile Val Gly Ser Val Arg Glu Glu Leu Ser Ala Met Glu
        435                 440                 445

Pro Gly Asp Val Trp Ala Leu Phe Asn Glu His Gly Arg Pro Asn Trp
    450                 455                 460

Tyr Ala Val Ile Gln Ser Arg Thr Gly Asp Arg Phe Ser Glu Ile Pro
465                 470                 475                 480

Asp Ala Thr Gly Lys Arg Ser Ile Thr Lys Leu Pro Leu Ser Ile Glu
                485                 490                 495

Met Lys Tyr Leu Glu Met Thr Pro Ala Tyr Ala Lys Asp Glu Val Asp
            500                 505                 510

Glu Trp Asn Pro Gln Arg Gly Ser Gly Leu Leu Lys Leu Arg Asp Val
        515                 520                 525

Val Asp Ile Gln Asp Asn Trp Gln Ala Phe Ser His Arg Val Thr Ser
    530                 535                 540

Tyr Val Lys Phe Glu Asn Ser Tyr Phe Val Tyr Pro Gly Asn Asp Glu
545                 550                 555                 560

Val Trp Ala Val Tyr His Ala Glu Thr Leu Ser Arg Tyr Phe Val Tyr
                565                 570                 575

Val Val Glu Ser Thr Ile Ile Cys Ala Arg Leu Leu Asn Asp Lys Pro
            580                 585                 590

Gly Gln Asp Glu Gly Phe Leu Ala Arg Cys Leu Leu Gln Lys Thr
        595                 600                 605

Thr Glu His Glu Val Tyr Leu Lys Thr Ser Lys Glu Val Glu Leu Ser
    610                 615                 620

Asp Ile Gln Pro Phe Cys Phe Arg Val Pro Phe His Ile Lys Asn Glu
625                 630                 635                 640

Ala Asn Leu Leu Lys Val Glu Val Ser Gly Val Lys Ser Arg Gln Ser
                645                 650                 655

Met Lys Ala Asp Arg Glu Thr Thr Ala Gly Tyr Lys Arg Lys Gln
            660                 665                 670

Gly Gln Gly Glu Ser Asp Asp Asp Asp Leu Asp Asp Val Asp Asn
        675                 680                 685

Asn Ser Pro Glu Asp Val Asn Ala Asp Gly Thr Thr Ala Glu Glu Met
    690                 695                 700

Leu Ala Glu Asp Glu Ala Ile Glu Val Met Asn Gly Gly Leu Glu Val
705                 710                 715                 720

Val Val Ala Leu Pro Asp Asp Ile Gly Asp Thr Asn Gly Gly Thr His
                725                 730                 735

<210> SEQ ID NO 16
<211> LENGTH: 711
<212> TYPE: PRT
<213> ORGANISM: Sphagnum fallax

<400> SEQUENCE: 16

-continued

```
Met Asp Gly Leu Leu Glu Lys Ile Val Glu Leu Ala Lys Asp Ala Glu
1               5                   10                  15

His Leu Lys Arg Thr Cys Arg Cys Glu His Gly Thr Pro Thr Arg Ser
            20                  25                  30

Asn Lys Lys Ala Lys Arg Asn Gly His Asn Gly Thr Pro Ala Ser Pro
            35                  40                  45

Glu Arg Gln Ser Thr Asp Ile Ile Ala Ser Ser Pro Phe Asn Phe Arg
50                  55                  60

Gly His Lys Leu Asp Phe Glu Gly Pro Gly Gly Asp Gly Asp Trp Val
65                  70                  75                  80

Ser Ala Phe Lys Ala Glu Ala Gly Pro Trp Ser Gly Glu Arg Leu Val
                85                  90                  95

Val Leu Ser Leu Phe Asp Gly Leu Gly Gly Ile Trp Gln Ala Leu Thr
                100                 105                 110

Lys Leu Gly Ile Pro Phe Ser Gly Tyr Ser Ser Glu Val Leu Ala Pro
            115                 120                 125

Ala Ile Gln Val Val Lys Ser Arg His Pro Arg Val Lys His Val Gly
130                 135                 140

Asp Ile Arg Lys Leu Asn Leu Ser Ala Val Pro Glu Lys Val Asp Leu
145                 150                 155                 160

Val Val Gly Gly Phe Pro Cys Gln Asp Leu Ser Ile Met Gly Lys Lys
                165                 170                 175

Glu Gly Leu His Gly Ser Arg Ser Lys Leu Phe Phe Asp Leu Leu Arg
            180                 185                 190

Val Leu Lys Val Phe Lys Pro Lys Trp Phe Leu Val Glu Asn Val Ala
            195                 200                 205

Ser Met Ser Trp Val Asp Arg Glu Glu Ile Thr Arg His Leu Lys Val
210                 215                 220

Ala Pro Met Glu Leu Asp Ser Gln Glu Ile Thr Ala Ser Lys Arg Arg
225                 230                 235                 240

Arg Leu Tyr Trp Thr Asn Ile Pro His Pro Arg Leu Pro Arg Leu
                245                 250                 255

Arg Asp His Pro Ser Thr Ser Leu Gln Ser Cys Leu Glu Gly Ala Leu
            260                 265                 270

Ala Leu Glu Gln Lys Cys Gly Val Ile Leu Cys Ser Asn Leu Tyr Lys
            275                 280                 285

Gly Ser Thr Ala Arg Leu Glu Leu Val Leu Asp Asn Lys Thr Asn Lys
            290                 295                 300

Leu Arg Tyr Ile Lys Gln Thr Glu Val Glu Val Leu Met Gly Tyr Pro
305                 310                 315                 320

Lys Asp Tyr Thr Asn Val Val Ala His Glu Thr Lys Gly Arg Thr Glu
                325                 330                 335

Gln Ala Glu Lys Val Leu Lys Thr Pro Val Arg Ala Lys Ser Val Glu
            340                 345                 350

Pro Lys Pro Ser Ser Val Thr Pro Ser Ser Arg Gln Leu Arg Lys
            355                 360                 365

Asn Arg Lys Ser Gln Thr Phe Phe Val Pro Gln Val Trp Glu Thr Lys
            370                 375                 380

Pro Thr Arg Gln Asp Ser Leu Lys Asp Ile Asp Arg Trp Phe Leu Leu
385                 390                 395                 400

Gly Asn Thr Phe Ser Val Gln Val Ile Ala Tyr Leu Thr Ser Pro Leu
                405                 410                 415
```

-continued

Leu Arg Ala Glu Val Arg Ser His Gly Lys Arg Val Asn Ile Val Gly
                420                 425                 430

Ser Val Lys Glu Glu Glu Leu Ser Ala Met Glu Pro Gly Asp Val Trp
                435                 440                 445

Ala Leu Phe Asn Glu Tyr Gly Arg Pro Asn Trp Tyr Ala Val Ile Glu
                450                 455                 460

Ser Arg Thr Gly Asp Arg Phe Ser Ala Phe Pro Asp Ala Thr Gly Lys
465                 470                 475                 480

Arg Asn Val Thr Lys Leu Pro Leu Lys Ile Glu Met Lys Tyr Leu Glu
                485                 490                 495

Met Thr Pro Ala Tyr Leu Lys Glu Glu Val Asp Glu Trp Asn Pro Gln
                500                 505                 510

Arg Gly Ser Gly Leu Leu Lys Leu Arg Asn Val Met Asp Ile Gln Asp
                515                 520                 525

Asn Trp Gln Ala Phe Ser His Arg Val Thr Ser Tyr Val Lys Leu Glu
                530                 535                 540

Asp Ser Tyr Phe Val Tyr Pro Gly Asn Asp Glu Val Trp Ala Val Tyr
545                 550                 555                 560

Asn Gly Glu Thr Leu Ser Arg Tyr Phe Val Tyr Val Ser Glu Ser Thr
                565                 570                 575

Ile Ser Ser Asp Arg Leu Arg Arg Gly Lys Pro Gly Gln Glu Gly Phe
                580                 585                 590

His Ala Arg Cys Leu Leu Leu Gln Lys Thr Ala Glu His Glu Ile Phe
                595                 600                 605

Leu Lys Thr Ser Thr Met Val Glu Phe Thr Asp Leu Gln Pro Phe Cys
610                 615                 620

Phe Arg Val Pro Phe Tyr Ile Lys His Glu Ala Asn Leu Leu Lys Val
625                 630                 635                 640

Glu Val Ser Gly Val Lys Ser Arg Gln Ser Met Arg Ala Asp Lys Asp
                645                 650                 655

Ser Thr Ala Gly Tyr Glu Arg Arg Gly Lys Lys Asp Leu Gly Gly Pro
                660                 665                 670

Asp Asp Asp Glu Asp Gly Asp Leu Ile Gly Gly Asp Leu Asp Phe Pro
                675                 680                 685

Glu Asp Asn Asp Ala Asp Arg Ile Gly Ala Ala Thr Gly Thr Pro Gly
                690                 695                 700

Ser Ile Glu Met Met Ser Gly
705                 710

<210> SEQ ID NO 17
<211> LENGTH: 739
<212> TYPE: PRT
<213> ORGANISM: Sphagnum fallax

<400> SEQUENCE: 17

Met Glu Asn Leu Phe Lys Lys Ile Gln Glu Leu Gln Asp Glu Ala Cys
1               5                   10                  15

Arg Leu Lys Glu Glu Glu Lys Glu Arg Gln Lys Gly Tyr Ser Ala Ser
                20                  25                  30

Ser Pro Gln Pro Ser Ser Thr Trp Asn Phe Thr Thr Asp Arg Gln Gln
                35                  40                  45

His Ser Ser Arg Thr Leu Pro Pro Cys Ala Ser Arg Arg Phe Asn Asn
            50                  55                  60

Leu Val Gln Gln Ser Ser Gln Ser Pro Leu Pro Tyr Pro Pro Cys Thr
65              70                  75                  80

```
Thr Asp Ile Lys Glu Pro Phe Glu Gly Val Val Gly Asp Gly Glu Trp
            85                  90                  95
Leu Arg Ala Phe Arg Lys Asp Ala Gly Pro Trp Asn Gly Glu Lys Leu
            100                 105                 110
Val Val Leu Ser Leu Phe Asp Gly Ile Gly Ile Trp Ala Ala Leu
            115                 120                 125
Thr Arg Leu Gly Ile Pro Phe Thr Gly Tyr Ser Ser Glu Val Ser Ile
            130                 135                 140
Pro Ala Leu Glu Val Leu Lys Ala Lys Tyr Pro Glu Val His His Val
145                 150                 155                 160
Gly Asp Val Arg Lys Val Glu Arg Met Thr Val Ser Glu Lys Val Asp
            165                 170                 175
Leu Val Val Gly Gly Phe Pro Cys Gln Asp Leu Ser Cys Met Gly Lys
            180                 185                 190
Arg Glu Gly Leu His Gly Gln Arg Ser Lys Leu Phe Phe Asp Leu Leu
            195                 200                 205
His Val Leu Lys Ile Phe Asn Pro Ser Trp Phe Leu Val Glu Asn Val
            210                 215                 220
Ala Ser Met Thr Trp Met Asp Arg Asp Glu Ile Ser Lys Tyr Leu Lys
225                 230                 235                 240
Leu Gln Pro Ile Glu Leu Asp Ser Ile Glu Leu Ala Pro Ser Lys Arg
            245                 250                 255
Arg Arg Leu Tyr Trp Thr Asn Ile Pro His Pro Ala Arg Leu Pro Arg
            260                 265                 270
Val Lys Asn His Pro Ser Thr Phe Val Gln Ser Cys Leu Leu Asp Gly
            275                 280                 285
Ile Ala Leu Glu Glu Lys Thr Gly Ile Ile Leu Ser Asn Asn Ser Tyr
            290                 295                 300
Lys Ser Asn Ser Cys Gln Met Glu Leu Val Leu Glu Asn Gly Thr Ser
305                 310                 315                 320
Glu Leu Arg Tyr Leu Ser His Val Glu Leu Glu Arg Ile Met Gly Tyr
            325                 330                 335
Pro Ser Asn His Thr Ser Leu Cys Ile Asp Glu Ala Glu Asn Asn Ser
            340                 345                 350
Asn Pro Met Ile Ser Asn Val Ser Arg Tyr Val Gln Thr Ser Asn Thr
            355                 360                 365
Tyr His Lys Lys Arg Gly Lys Ile Cys Gly Val Gly Gly Pro Thr Arg
            370                 375                 380
Phe Cys Thr Pro Pro Ala Ser Thr Leu Gly Glu Pro Leu Lys Asp Ser
385                 390                 395                 400
Val Arg Trp Ala Leu Leu Gly Asn Thr Phe Thr Val Pro Val Ile Ala
            405                 410                 415
Tyr Leu Val Ser Pro Leu Leu Lys Ser Ser Val Arg Val Leu Ala Gln
            420                 425                 430
Pro Val Thr Ile Ser Asp Pro Val Lys Glu Ser Glu Cys Ser Val Met
            435                 440                 445
Asp Pro Asp Asp Val Trp Ala Leu Tyr Asn Glu His Glu Arg Pro Asn
450                 455                 460
Trp Tyr Ala Leu Ile Leu Arg Arg Ser Gly Asp Arg Phe Ser Arg Cys
465                 470                 475                 480
Gly Arg Ala Asp Lys Lys Asn Pro Leu Arg Ile Glu Met Gln Tyr Leu
            485                 490                 495
```

```
Glu Ile Thr Gln Pro Tyr Leu Glu Gly Glu Asp Ser Trp Asn Met
                500                 505                 510

Leu Arg Gly Thr Gly Leu Phe Glu Leu Arg Gln Gln Ile Asp Cys Gln
            515                 520                 525

Ile Ser Trp Val Thr Phe Ser His Arg Val Thr Ser Val Val Lys Val
530                 535                 540

Gln Asp Lys Phe Phe Ile Tyr Pro Gly Gln Asp Glu Val Trp Ala Val
545                 550                 555                 560

Cys Ser Arg Lys Ala Trp Ser Asn Phe Val Tyr Val Val Glu Ser
                565                 570                 575

Ser Val Asp Ile Ser Arg Leu Gln Ser Gly Arg Pro Gly Asn Glu Gly
                580                 585                 590

Phe Thr Ala Cys Cys His Leu Leu Ile Lys Thr Thr Glu His Glu Thr
                595                 600                 605

Tyr Arg Lys Thr Asn Thr Thr Leu Glu Phe Thr Asp Ile Ser Leu Phe
                610                 615                 620

Cys Phe Arg Ala Pro Tyr Val Phe Lys Gln Gln Ala Asn Met Leu Arg
625                 630                 635                 640

Leu Glu Val Gly Ala Lys Gly Arg Lys Val Arg Asn Ile Glu Ser Gly
                645                 650                 655

Ile Arg Arg Ser Lys Arg Lys Arg Lys Asp Thr Pro Glu Ala Leu Arg
                660                 665                 670

Asp Asp Val Asn Glu Glu Gly Gly Tyr Ile Ala Asn Val Phe Gln
                675                 680                 685

Gly Thr Asp Arg Val Glu Gln Lys Gly Arg Ala Ala Thr Thr Asp Ile
                690                 695                 700

Tyr Asp Val Gly Tyr Gly Pro Gln Ile Asn Ala Ser Ile Asp Glu Glu
705                 710                 715                 720

Ser Thr Gln Gln His Leu Ala Asp Pro Glu Thr Ile Ile Ser Asp
                725                 730                 735

Asp Asp Asp

<210> SEQ ID NO 18
<211> LENGTH: 767
<212> TYPE: PRT
<213> ORGANISM: Sphagnum fallax

<400> SEQUENCE: 18

Met Asp Ser Ile Ile Lys Lys Leu Gln Glu Leu Glu Arg Glu Ala Arg
1               5                   10                  15

Ala Leu Gln Glu Lys Glu Lys Glu Gln Val Tyr Ser Gln Leu Gln Thr
                20                  25                  30

Thr Pro Ala Gly Asn Val Asn Asp Arg Gln Glu Val Ser Ser Gly Trp
            35                  40                  45

Pro Ser Gly Ser Phe Asn Gln Glu Phe Pro Cys Thr Pro Val Pro Leu
50                  55                  60

Cys Thr Thr Arg Ser Lys Glu Ala Phe Glu Gly Asp Gly Asp Gly Asp
65                  70                  75                  80

Trp Trp Thr Ala Phe Arg Lys Lys Ala Gly Pro Trp Lys Gly Glu Lys
                85                  90                  95

Leu Val Val Leu Ser Leu Phe Asp Gly Ile Gly Gly Ile Trp Ala Ala
                100                 105                 110

Leu Thr Arg Leu Gly Ile Pro Phe Val Gly Tyr Ser Ser Glu Val Ser
                115                 120                 125
```

Pro Pro Ala Ile Gln Val Val Lys Ala Arg Tyr Pro Asp Val His His
130                 135                 140

Val Gly Asp Val Arg Lys Leu Asp Arg Thr Ser Phe Ser Gly Asn Val
145                 150                 155                 160

Asp Leu Val Val Gly Gly Phe Pro Cys Gln Asp Leu Ser Ala Met Gly
                165                 170                 175

Arg Arg Glu Gly Leu His Gly Gln Arg Ser Lys Leu Phe Phe Asp Leu
            180                 185                 190

Leu Arg Val Leu Lys Glu Phe Lys Pro Lys Trp Phe Leu Val Glu Asn
        195                 200                 205

Val Ala Ser Met Thr Trp Ile Asp Arg Glu Glu Ile Ser Lys Tyr Leu
210                 215                 220

Arg Val Tyr Pro Ile Glu Leu Asp Ser Ile Glu Leu Thr Pro Thr Arg
225                 230                 235                 240

Arg Arg Arg Val Tyr Trp Thr Asn Ile Pro Tyr Pro Arg Leu Pro
                245                 250                 255

Arg Val Lys Asp His Pro Ser Thr Phe Val Gln Ser Cys Leu His Asn
            260                 265                 270

Ala Ile Ala Leu Glu Glu Lys Thr Gly Val Val Met Gly Phe Gly Ser
        275                 280                 285

Asp Lys Ala Asn Ser Cys Leu Leu Glu His Val Met Asp Ile Glu Thr
    290                 295                 300

Arg Lys Met Arg Gly Ile Thr Gln Ile Glu Val Glu Val Met Met Gly
305                 310                 315                 320

Tyr Pro Pro Asn His Thr Asn Leu Leu Ile Thr Glu Ala Lys His Gln
                325                 330                 335

Thr Asn Ala Leu Val Gln Thr Pro Ser Lys Met Gln Thr Ser Ser Ala
            340                 345                 350

Ser Lys Lys Lys Gln Gly Lys Ile Ser Gly Ser Arg Gly Ser Leu Ser
        355                 360                 365

Gln Asn Pro Ile Thr Pro Ala Ile Arg Trp Ala Leu Leu Gly Asn Thr
    370                 375                 380

Phe Thr Val Pro Thr Ile Gly Tyr Leu Ile Ser Pro Leu Leu Lys Gly
385                 390                 395                 400

Ser Val Arg Val Leu Gly Gln Pro Val Ile Pro Gly Pro Thr Lys
                405                 410                 415

Glu Asn Glu Cys Ser Val Met Glu Pro Tyr Asp Val Trp Ala Leu Tyr
            420                 425                 430

Asn Glu His Glu Arg Pro Asn Trp Tyr Ala Arg Ile Leu Lys Arg Ala
        435                 440                 445

Gly Asp Arg Phe Ser Arg Met Ser Tyr Gly Ala Lys Lys His Pro Leu
    450                 455                 460

Tyr Ile Glu Met Gln Tyr Leu Glu Ile Thr Thr Pro Tyr Leu Glu Gly
465                 470                 475                 480

Glu Asp Asp Glu Trp Asn Pro Leu Arg Gly Thr Gly Leu Phe Glu Leu
                485                 490                 495

Arg Glu Glu Val Asp Thr Gln Val Ala Trp Thr Thr Phe Ser His Arg
            500                 505                 510

Val Thr Ser Cys Leu Thr Leu Gly Asp Lys Phe Tyr Val Tyr Pro Gly
        515                 520                 525

Lys Asp Glu Val Trp Ala Val Tyr Ser Arg Gln Thr Trp Ser Pro Phe
    530                 535                 540

Phe Val Tyr Val Val Glu Ser Asn Ile Asn Ile Lys Thr Leu Asp Ser

```
            545                 550                 555                 560
        Ala Lys Pro Gly Leu Glu Gly Phe Tyr Ala Ser Cys Arg Leu Met Leu
                        565                 570                 575

Arg Thr Ala Glu Leu Gly Val Tyr Arg Lys Thr Glu His Val Leu Glu
                        580                 585                 590

Phe Thr Asp Leu Ser Leu Phe Cys Phe Arg Ala Pro His Ile Phe Arg
                        595                 600                 605

Gln Glu Ala Asn Leu Leu Lys Val Glu Val Ser Ala Ser Gly Arg Lys
                        610                 615                 620

Thr Lys Asn Ile Glu Arg Gly Ile Arg Arg Ser Lys Glu Ser Gln Glu
        625                 630                 635                 640

Leu Glu Asp Ala Glu Gly Arg Glu Asp Ile Glu Gly Glu Glu Gln Glu
                        645                 650                 655

Glu Gln Glu Glu Gln Asn Leu Val Glu Glu Thr Ile Asn Arg Arg Ile
                        660                 665                 670

Thr Arg Asn Phe Glu Arg Glu Leu Arg Gly Arg Lys Arg Lys Gln Ser
                        675                 680                 685

Arg Leu Thr Val Phe Gln Asp Asn Glu Val Lys Lys Arg Gly Gly Arg
                        690                 695                 700

Glu Asp Gln Glu Gly Tyr Pro Leu Gln Glu Ala Gly Asp Ala Asp Leu
        705                 710                 715                 720

Gly Lys Lys Ala Pro Lys Cys Lys His Asp Phe Asp Asp Glu Glu Leu
                        725                 730                 735

Asn Asp Asp Val Asn Arg Asp Ser Gly Gln Glu Asn Gly Ala Ser Thr
                        740                 745                 750

Pro Glu Thr Val Val Thr Asp Asp Gly Leu Leu His Asp Met
                        755                 760                 765

<210> SEQ ID NO 19
<211> LENGTH: 551
<212> TYPE: PRT
<213> ORGANISM: Encephalartos barteri

<400> SEQUENCE: 19

Glu Asp Glu Trp Ile Asp Leu Leu Lys Leu Lys Ser Ala Asp Trp Thr
        1               5                   10                  15

Gly Lys Pro Leu Val Val Leu Ser Leu Phe Asp Gly Ile Gly Ala Ile
                        20                  25                  30

Trp Ala Ala Leu Ser Leu Thr Gly Ile Pro Phe Val Gly Tyr Ser Ser
                        35                  40                  45

Glu Ile Asn Pro Tyr Ala Arg Gln Ile Val Lys Glu Arg Tyr Pro Asp
                        50                  55                  60

Val Lys Cys Leu Gly Asp Ile Lys Asn Ile Lys Lys Gly Asp Ile Asn
        65                  70                  75                  80

Asp Asn Val Asp Phe Ile Val Gly Gly Phe Pro Cys Gln Asp Leu Ser
                        85                  90                  95

Cys Met Gly Lys Lys Ala Gly Leu His Gly Asp Gln Ser Lys Leu Phe
                        100                 105                 110

Phe Glu Leu Leu Arg Met Leu Gln Ile Phe Gln Pro Thr Trp Phe Leu
                        115                 120                 125

Val Glu Asn Val Ala Ser Met Ser Trp Val Asp Arg Asp Glu Ile Ser
                        130                 135                 140

Lys Tyr Leu Gly Cys Leu Pro Ile Glu Met Asp Ser Gln Asp Leu Thr
        145                 150                 155                 160
```

```
Pro Thr Arg Arg Arg Leu Phe Trp Thr Asn Ile Pro His Pro Lys
            165                 170                 175

Ser Leu Pro Lys Val Arg Asp Asn Leu Ser Thr Ser Leu Gln Ser Val
        180                 185                 190

Leu Glu Asn Ala Ile Ala Leu Gln Ala Lys Thr Ala Cys Val Leu Ser
    195                 200                 205

Ala Asn His Ser Pro Gly Ser Ala Gly Gln Val Gln Gln Val Leu Asp
210                 215                 220

Asp Lys Glu Gly Asn Leu Arg Ser Ile Thr Ile Ser Glu Leu Glu Lys
225                 230                 235                 240

Ile Met Gly Phe Pro Pro Gly Tyr Thr Asp Phe Gln Phe Ser Phe Thr
                245                 250                 255

Ser Glu Thr Gln Ser Pro Lys Pro Ala Lys Thr Trp Ser Pro Asn Ser
            260                 265                 270

Pro Gly Lys Ser Glu Lys Pro Ile Lys Leu Ser Asp Pro Asp Gly Ser
        275                 280                 285

Ala Ile Thr Thr Glu Lys Val Thr Lys Tyr Asn Ile Arg Trp Arg Leu
    290                 295                 300

Leu Gly Asn Thr Phe Ser Val Lys Val Ile Val Tyr Leu Leu Ser Ser
305                 310                 315                 320

Leu Leu Asn Arg Ser Val Arg Glu Arg Lys Val Asn Pro Ile Val Leu
                325                 330                 335

Pro Lys Asn Ile Gln Glu Gln Lys Cys Ser Val Met Glu Glu Gly Asp
            340                 345                 350

Ile Trp Ala Leu Tyr Asn Thr His Ala Gln Pro Asn Trp Tyr Gly Phe
        355                 360                 365

Ile Val Lys Arg Ser Gly Gly Arg Phe Ser Lys Ser Gly Lys Asn Gly
    370                 375                 380

Arg Asn Gly His Ile Arg Ile Glu Val Lys Phe Leu Glu Leu Thr Tyr
385                 390                 395                 400

Asp Tyr Thr Ser Gly Glu Ala Asp Lys Trp Ser Pro Asp Arg Gly Ala
                405                 410                 415

Gly Lys Tyr Lys Met Asn Arg Asp Ser Asp Ile Gln Asp Asn Trp Pro
            420                 425                 430

Ile Phe Ser His Arg Val Arg Ser Tyr Tyr Lys Ser Gln Tyr Cys Tyr
        435                 440                 445

Phe Ile Tyr Pro Gly Lys Asp Glu Val Trp Ala Val Tyr Asn Arg Gln
    450                 455                 460

Lys Thr Lys Ser Ser Pro Phe Phe Val Tyr Val Ile Glu Ser Ser Ile
465                 470                 475                 480

Asn Ala His Lys Trp Glu Ser Val Lys Pro Gly Lys Glu Gly Phe Lys
                485                 490                 495

Ala Arg Cys Tyr Val Met Gln Gln Thr Ser Gln Pro Glu Leu Phe Arg
            500                 505                 510

Leu Thr Glu Lys Thr Leu Glu Tyr Glu Asp Leu Ser Cys Phe Ser Phe
        515                 520                 525

Ser Val Pro Tyr His Phe Lys Asp Glu Phe Gly Val Leu Lys Ile Glu
    530                 535                 540

Tyr Ser Asn Asn Asn Gln Arg
545                 550

<210> SEQ ID NO 20
<211> LENGTH: 562
<212> TYPE: PRT
```

<213> ORGANISM: Welwitschia mirabilis

<400> SEQUENCE: 20

```
Glu Trp Ile Asp Leu Leu Arg Leu Gln Ser Gln Glu Trp Glu Lys
 1               5                  10                  15
Pro Leu Val Val Leu Ser Leu Phe Asp Gly Ile Gly Ala Ile Trp Glu
            20                  25                  30
Ala Leu Thr Ile Leu Gly Ile Pro Phe Val Gly Tyr Ser Ser Glu Ile
                35                  40                  45
Asp Pro Cys Ala Ile Gln Val Val Lys Glu Arg Tyr Pro Lys Val Lys
 50                  55                  60
His Val Gly Asp Val Lys Asn Leu Lys Thr Glu Asp Ile Lys Glu Lys
 65                  70                  75                  80
Val Asp Leu Leu Val Gly Gly Phe Pro Cys Gln Asp Leu Ser Ser Met
                85                  90                  95
Gly Arg Lys Val Gly Leu His Gly Glu Arg Ser Lys Leu Phe Phe Asp
                100                 105                 110
Leu Leu Gln Ala Met Gln Met Phe Glu Pro Tyr Trp Phe Leu Val Glu
                115                 120                 125
Asn Val Ala Ser Met Ser Trp Val Asp Arg Asp Glu Ile Cys Lys Tyr
130                 135                 140
Ile Ala Cys Leu Pro Ile Glu Leu Asp Ser Gln Asp Leu Thr Pro Gly
145                 150                 155                 160
Lys Arg Arg Arg Leu Tyr Trp Thr Asn Ile Pro Phe Pro Glu Thr Leu
                165                 170                 175
Pro Asn Val Arg Asp Asn Ser Ser Thr Ser Leu Gln Ser Val Leu Glu
                180                 185                 190
Asn Ala Thr Ala Leu Gln Thr Lys Thr Lys Cys Ile Met Ser Ser Ser
            195                 200                 205
Ser Lys Ile Gly Lys Met Gly Ser Phe Gln Gln Val Leu Asn Asn Asn
    210                 215                 220
Asp Gly Thr Leu Arg Asp Val Ser Val Thr Glu Leu Glu Lys Ile Met
225                 230                 235                 240
Gly Phe Pro Thr Gly His Thr Lys Phe Asp Leu Gln Ala Val Gln Ser
                245                 250                 255
Ser Arg Ser Pro Lys Ser Ser Asn Leu Arg Gly Pro Asn Ser Asn Gly
            260                 265                 270
Lys Ala Ile Leu Gln Ser Thr Glu Ile Asp Asn Ile Arg Trp Arg Met
    275                 280                 285
Leu Gly Asn Ser Phe Ser Val Lys Thr Val Ala Tyr Leu Leu Ser Ser
    290                 295                 300
Leu Ile Asn Lys Ser Val Arg Asp Asn Lys Val Glu His Lys Leu Pro
305                 310                 315                 320
Tyr Arg Asn Ile Gln Ala Glu Glu Cys Ser Val Met Asp Pro Gly Glu
                325                 330                 335
Leu Trp Val Leu Tyr Asn Gly Arg Gly Leu Pro Asn Trp Tyr Gly Ile
                340                 345                 350
Ile Val Asn Arg Ser Gly Gly Arg Phe Thr Met Lys Ser His Lys Asn
                355                 360                 365
Gly Asn Thr His Val Gln Val Glu Val Arg Phe Leu Glu Leu Ser Tyr
    370                 375                 380
Glu Tyr Gly Gly Lys Asp Glu Asp Glu Gln Cys Pro Glu Arg Gly Thr
385                 390                 395                 400
```

```
Gly Arg Tyr Lys Ile Cys Arg Asp Thr Glu His Gln Asn Ser Trp Phe
                405                 410                 415

Ala Phe Ser His Arg Met Lys Ser Tyr Trp Lys Asn Lys His Ala Tyr
            420                 425                 430

Phe Ile Tyr Pro Gly Lys Gly Glu Val Trp Ala Ile Asn His Arg Trp
        435                 440                 445

Arg Ala Lys Thr Cys Pro Phe Phe Val Tyr Val Ala Asp Ser Glu Phe
    450                 455                 460

Ser Ile Pro Gln Asn Lys Leu Gly Ser Thr Lys Pro Gly Lys Glu Lys
465                 470                 475                 480

Phe Lys Ala Lys Cys Tyr Ala Leu Gln Gln Thr Leu Asp Ala Glu Val
                485                 490                 495

Tyr Lys Ile Thr Asp Lys Leu Leu Ala Tyr Glu Asp Leu Ser Val Phe
            500                 505                 510

Ile Tyr Ser Val Pro Tyr Tyr Lys Asp Ala Lys Gly Leu Leu Lys
        515                 520                 525

Ile Glu Tyr Thr Asn Gln Lys Glu Ile Glu His Ala Gly Ala Leu Glu
    530                 535                 540

Arg Thr Ser Lys Arg Arg Arg Gln Asp Tyr Asp Ser Ser Asp Asp Glu
545                 550                 555                 560

Glu Asp

<210> SEQ ID NO 21
<211> LENGTH: 653
<212> TYPE: PRT
<213> ORGANISM: Marchantia polymorpha

<400> SEQUENCE: 21

Met Glu Arg Leu Leu Thr Lys Ile Arg Asp Leu Glu Lys Glu Ala Leu
1               5                   10                  15

Asn Ile Ala Ser Lys Gln Glu Arg Lys Arg Ile Arg Ile Lys Glu Thr
            20                  25                  30

Asn Glu Glu Cys Cys Trp His Cys Glu Gly Gln Asp Trp Ile Asn Asp
        35                  40                  45

Val Arg Leu Lys Gly Gly Glu Trp Thr Gly Lys Pro Leu Val Val Leu
    50                  55                  60

Ser Leu Phe Asp Gly Ile Gly Gly Val Trp Val Ala Leu Glu Arg Leu
65                  70                  75                  80

Gly Ile Pro Phe Val Gly Tyr Ser Cys Glu Val Asn Asp Ala Ala Met
                85                  90                  95

Gln Val Ile Lys His Arg Tyr Gly Met Val Arg His Leu Gly Asp Val
            100                 105                 110

Lys Glu Leu Glu Lys Ala Asp Ile Pro Glu Lys Val Asp Leu Ile Ile
        115                 120                 125

Gly Gly Phe Pro Cys Gln Asp Leu Ser Ser Leu Gly His Lys Met Gly
    130                 135                 140

Leu His Gly Gln Arg Ser Lys Leu Phe Phe Glu Met Leu Arg Ile Ile
145                 150                 155                 160

Lys Ile Phe Asn Pro Thr Trp Phe Leu Ala Glu Asn Val Ala Ser Met
                165                 170                 175

Thr Trp Ile Asp Arg Gln Glu Ile Ser Lys His Leu Asn Thr Thr Pro
            180                 185                 190

Ile Glu Ile Asp Ala Glu Glu Ile Thr Pro Ser Lys Arg Arg Arg Ile
        195                 200                 205
```

```
Tyr Trp Ser Asn Ile Pro Tyr Pro Asn Lys Ile Pro Arg Ile Arg Asp
210                 215                 220

His Glu Ser Thr Ala Leu Gln Ser Val Leu His Asn Ala Thr Ala Leu
225                 230                 235                 240

Asp Lys Lys Val Gly Cys Ile Leu Ser Gln Asn Asn His Lys Ala Gly
                245                 250                 255

Tyr Gly Ser Leu Glu Leu Val Met Asp Asn Asn Thr Asn Lys Leu Arg
                260                 265                 270

Tyr Ile Ser Val Ile Glu Thr Glu Leu Ala Met Gly Tyr Pro Pro Gly
                275                 280                 285

Tyr Thr Asn Val Lys Phe Asn His Ser Cys Glu Lys Lys Thr Ile Ser
290                 295                 300

Ser Thr Ala Asn Tyr Arg Thr Glu Val Asn Ile Thr Asn Ile Thr Arg
305                 310                 315                 320

Arg Ala Gly Glu Lys Met Leu Arg Ser Lys Arg Ile Val Gln Ser Ser
                325                 330                 335

Gln Arg Leu Val Glu Glu Met Ser Ser Val Lys Ser Ser Phe Ala
                340                 345                 350

Asp Gly Ile Asn Arg Ser Ala Arg Trp His Leu Leu Gly Asn Thr Phe
                355                 360                 365

Ser Val Pro Val Ile Cys Tyr Leu Leu Ser Pro Leu Leu Tyr Arg Glu
370                 375                 380

Val Arg Ala Ala Pro Ile Pro Ile Ser Leu Pro Lys Tyr Ile Lys Glu
385                 390                 395                 400

Gln Asp Cys Ser Ala Met Asp Pro Gly Glu Val Trp Ala Leu Tyr Asn
                405                 410                 415

Ser His Glu Arg Pro Asn Trp Tyr Ala Val Ile Val Ser Arg Ser Gly
                420                 425                 430

Asp Arg Phe Ser Asp Val Arg Ile Gln Leu Gly Arg Lys Arg Pro Pro
                435                 440                 445

Ile Tyr Ile Glu Val Lys Phe Met Glu Met Thr Ser Ala Tyr Ala Ala
                450                 455                 460

Gly Glu Pro Asp Asn Trp Asp Thr Asn Arg Gly Thr Gly Leu Phe His
465                 470                 475                 480

Leu Arg Glu Leu Ile Asp Lys Gln Asn Ser Trp Val Ala Phe Ser His
                485                 490                 495

Arg Val Ser Thr Phe Leu His Phe Asp Asn His Tyr Phe Met Tyr Pro
                500                 505                 510

Gly Lys Asp Glu Val Trp Ala Ile Tyr Asp Asn Ala Ala Lys Cys Arg
                515                 520                 525

Tyr Leu Val Tyr Val Leu Thr Ser Glu Ile Asp Arg Gln Lys Ala Lys
                530                 535                 540

Leu Gly Lys Pro Gly Lys Glu Gly Phe His Ala Arg Cys Arg Leu Leu
545                 550                 555                 560

Gln Arg Thr Glu Asn Glu Val Tyr Arg Phe Met Asp Ala Glu Leu Asp
                565                 570                 575

Leu Thr Asp Leu Ser Ile Phe Ala Phe Arg Ala Pro Phe His Tyr Lys
                580                 585                 590

Asn Glu Ser Asn Leu Leu Arg Ile Glu Leu Thr Leu Arg Gln Arg Lys
                595                 600                 605

Gln Gly Pro Glu Asn Asp Lys Gln Asn Cys Lys Arg Arg Lys Arg Tyr
                610                 615                 620

Ser Asp Ser Asp Glu Asp Asp Glu Glu Asp Glu Val Glu Ala Thr Asp
```

```
                625                 630                 635                 640

Ser Glu Ala Val Val Thr Ala Glu Asp Asp Ser Gly Arg
                        645                 650

<210> SEQ ID NO 22
<211> LENGTH: 686
<212> TYPE: PRT
<213> ORGANISM: Marchantia polymorpha

<400> SEQUENCE: 22

Met Asp Lys Val Leu Asn His Ile Arg Asn Leu Arg Ala Glu Ala Glu
1               5                   10                  15

Ser Leu Leu Lys Asn Gly Asn Arg His Asp Gly Asp Glu Ala His
                20                  25                  30

Cys Gly Val Glu Lys Ser Ile Asp Cys Ser Asn Cys Gly Gly Asp Arg
                35                  40                  45

Trp Val Leu Lys Leu Arg Gln Lys Ala Gly Phe Trp Arg Ser Lys Pro
        50                  55                  60

Leu Val Val Leu Ser Leu Phe Asp Gly Ile Gly Val Trp Ala Ala
65                  70                  75                  80

Leu Glu Asn Leu Gly Ile Pro Phe Ile Gly Tyr Ser Cys Glu Val Asn
                        85                  90                  95

Ala Asp Ala Met Lys Val Thr Gln Arg Asn Tyr Cys Ser Val Arg His
                100                 105                 110

Leu Gly Asp Ile His Arg Leu Lys Lys Ala Asp Ile Lys Glu Lys Ile
            115                 120                 125

Asp Leu Val Val Gly Gly Phe Pro Cys Gln Asp Leu Ser Ser Met Gly
        130                 135                 140

Ala Arg Leu Gly Leu His Gly Ser Arg Ser Arg Leu Phe Phe Glu Met
145                 150                 155                 160

Leu Arg Val Ile Lys Thr Phe Ser Pro Thr Trp Phe Leu Ala Glu Asn
                165                 170                 175

Val Ala Ser Met Ser Trp Val Asp Arg Glu Glu Ile Ser Lys His Leu
                180                 185                 190

Ser Thr Thr Pro Leu Glu Ile Asp Ser Gln Asn Phe Ser Pro Cys Lys
            195                 200                 205

Arg Arg Arg Leu Tyr Trp Ser Asn Ile Pro Tyr Pro Lys Thr Cys Pro
        210                 215                 220

Arg Ile Gly Asp Asn Glu Ala Thr Ser Ile Gln Ser Val Val Gln Gly
225                 230                 235                 240

Gly Ala Ser Leu Ala Lys Lys Asn Met Cys Val Leu Ser Ser Asn Gly
                245                 250                 255

Leu Gln Gly Ala Thr Lys Ala Leu Met Glu Leu Val Tyr Asp Phe Arg
                260                 265                 270

Ile Asp Lys Pro Arg Tyr Ile Asn Val Val Glu Val Gln Met Met
            275                 280                 285

Gly Tyr Pro Pro His Tyr Thr Asn Val Lys Phe Asp Asp Gln Lys Pro
        290                 295                 300

Lys Ala Lys Ile Gln Arg Arg Glu Thr Glu Ile Lys Glu Gly Gly
305                 310                 315                 320

Val Asp Arg Asn Thr Arg Trp Arg Leu Gly Asn Ser Phe Ser Val
                325                 330                 335

Pro Val Ile Ser Phe Leu Leu Ser Pro Leu Leu Asp Ala Asp Ile Arg
                340                 345                 350
```

-continued

```
Asp Gln Thr Arg Lys Tyr His Leu Pro Ala Ser Val Arg Glu Ala Asp
            355                 360                 365

Cys Ser Val Met Ser Pro Gly Glu Ile Trp Ala Met Tyr Asn Ile His
370                 375                 380

Gln Arg Pro Asn Trp Tyr Val Gln Ile Val Ser Arg Ser Gly Glu Arg
385                 390                 395                 400

Phe Asp Leu Asn Val Asn Glu Arg Gly Lys Lys Gly Ser Arg Leu Pro
                405                 410                 415

Leu Arg Ile Glu Cys Arg Phe Leu Glu Leu Thr Lys Pro Tyr Glu Ala
            420                 425                 430

Gly Gln Leu Asp Leu Trp Ser Thr Ile Arg Gly Cys Gly Leu Tyr Thr
            435                 440                 445

Val Ser Glu Gly Ile Glu Val Gln Gly Ser Trp Val Ala Phe Ser His
450                 455                 460

Gln Val Thr Ser Leu Leu Lys Val Asp His Gly Leu Ile Phe Ile Tyr
465                 470                 475                 480

Pro Ala Lys Gly Glu Val Trp Ser Val Tyr Asp Ser Gly Thr Glu Ser
                485                 490                 495

Arg Tyr Leu Val Tyr Val Leu Glu Ser Ser Val Asn Thr Lys Lys Ala
            500                 505                 510

Lys Leu Arg Val Pro Gly Lys Glu Gly Phe Ser Ala Arg Cys Arg Leu
            515                 520                 525

Leu Gln Lys Lys Ile Glu Leu Asp Leu Tyr Arg Ile Ile Asp Lys Glu
            530                 535                 540

Leu Val Tyr Thr Asp Leu Gly Val Phe Ser Phe Arg Ala Pro Tyr His
545                 550                 555                 560

Phe His Gly Glu Gly Asp Val Leu Lys Ile Glu Leu Ser Val Lys Asp
                565                 570                 575

Arg Glu Arg Gly Ala Gln Ile Asp Gly Leu Lys Arg Lys Arg Leu Ser
            580                 585                 590

Arg His Phe Glu Ser Asp Asp Glu Asp Phe Leu Asp Met Asp Ile Gly
            595                 600                 605

Asp Glu Phe Gly Ala Met Pro Ile Ala Ile Gly Asn Ile Thr Ser Glu
610                 615                 620

Pro Leu Ala Asn Gly Glu Ser Lys Ser Glu Ser Ile Leu Thr Val Val
625                 630                 635                 640

Thr Lys Arg Asp Glu Glu Arg Leu Val Gln Pro Lys Glu Asp Ala Ile
                645                 650                 655

Arg Gly His Leu Glu Pro Leu Lys Leu Lys Pro Ala Pro Arg Arg Ser
            660                 665                 670

Ser Arg Ser Thr Ala Gly Leu Arg Ser Thr Pro Tyr Thr Pro
            675                 680                 685
```

<210> SEQ ID NO 23
<211> LENGTH: 1367
<212> TYPE: PRT
<213> ORGANISM: Artificial sequence
<220> FEATURE:
<223> OTHER INFORMATION: Amino acid sequence of the catalytically
      inactive S. pyogenes Cas9

<400> SEQUENCE: 23

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30
```

```
Val Leu Gly Asn Thr Asp Arg His Ser Ile Lys Lys Asn Leu Ile Gly
         35                      40                  45

Ala Leu Leu Phe Asp Ser Gly Glu Thr Ala Glu Ala Thr Arg Leu Lys
     50                  55                  60

Arg Thr Ala Arg Arg Tyr Thr Arg Arg Lys Asn Arg Ile Cys Tyr
 65              70                  75                  80

Leu Gln Glu Ile Phe Ser Asn Glu Met Ala Lys Val Asp Asp Ser Phe
                 85                  90                  95

Phe His Arg Leu Glu Glu Ser Phe Leu Val Glu Glu Asp Lys Lys His
             100                 105                 110

Glu Arg His Pro Ile Phe Gly Asn Ile Val Asp Glu Val Ala Tyr His
             115                 120                 125

Glu Lys Tyr Pro Thr Ile Tyr His Leu Arg Lys Lys Leu Val Asp Ser
         130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                 165                 170                 175

Asn Ser Asp Val Asp Lys Leu Phe Ile Gln Leu Val Gln Thr Tyr Asn
             180                 185                 190

Gln Leu Phe Glu Glu Asn Pro Ile Asn Ala Ser Gly Val Asp Ala Lys
             195                 200                 205

Ala Ile Leu Ser Ala Arg Leu Ser Lys Ser Arg Arg Leu Glu Asn Leu
         210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                 245                 250                 255

Leu Ala Glu Asp Ala Lys Leu Gln Leu Ser Lys Asp Thr Tyr Asp Asp
             260                 265                 270

Asp Leu Asp Asn Leu Leu Ala Gln Ile Gly Asp Gln Tyr Ala Asp Leu
         275                 280                 285

Phe Leu Ala Ala Lys Asn Leu Ser Asp Ala Ile Leu Leu Ser Asp Ile
         290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                 325                 330                 335

Leu Val Arg Gln Gln Leu Pro Glu Lys Tyr Lys Glu Ile Phe Phe Asp
             340                 345                 350

Gln Ser Lys Asn Gly Tyr Ala Gly Tyr Ile Asp Gly Gly Ala Ser Gln
             355                 360                 365

Glu Glu Phe Tyr Lys Phe Ile Lys Pro Ile Leu Glu Lys Met Asp Gly
         370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                 405                 410                 415

Glu Leu His Ala Ile Leu Arg Arg Gln Glu Asp Phe Tyr Pro Phe Leu
             420                 425                 430

Lys Asp Asn Arg Glu Lys Ile Glu Lys Ile Leu Thr Phe Arg Ile Pro
         435                 440                 445
```

```
Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp Ala Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
```

```
                865                 870                 875                 880
Tyr Trp Arg Gln Leu Leu Asn Ala Lys Leu Ile Thr Gln Arg Lys Phe
                    885                 890                 895
Asp Asn Leu Thr Lys Ala Glu Arg Gly Gly Leu Ser Glu Leu Asp Lys
                    900                 905                 910
Ala Gly Phe Ile Lys Arg Gln Leu Val Glu Thr Arg Gln Ile Thr Lys
            915                 920                 925
His Val Ala Gln Ile Leu Asp Ser Arg Met Asn Thr Lys Tyr Asp Glu
        930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
                    980                 985                 990
Gly Thr Ala Leu Ile Lys Lys Tyr Pro Lys Leu Glu Ser Glu Phe Val
            995                 1000                1005
Tyr Gly Asp Tyr Lys Val Tyr Asp Val Arg Lys Met Ile Ala Lys
    1010                1015                1020
Ser Glu Gln Glu Ile Gly Lys Ala Thr Ala Lys Tyr Phe Phe Tyr
    1025                1030                1035
Ser Asn Ile Met Asn Phe Phe Lys Thr Glu Ile Thr Leu Ala Asn
    1040                1045                1050
Gly Glu Ile Arg Lys Arg Pro Leu Ile Glu Thr Asn Gly Glu Thr
    1055                1060                1065
Gly Glu Ile Val Trp Asp Lys Gly Arg Asp Phe Ala Thr Val Arg
    1070                1075                1080
Lys Val Leu Ser Met Pro Gln Val Asn Ile Val Lys Lys Thr Glu
    1085                1090                1095
Val Gln Thr Gly Gly Phe Ser Lys Glu Ser Ile Leu Pro Lys Arg
    1100                1105                1110
Asn Ser Asp Lys Leu Ile Ala Arg Lys Lys Asp Trp Asp Pro Lys
    1115                1120                1125
Lys Tyr Gly Gly Phe Asp Ser Pro Thr Val Ala Tyr Ser Val Leu
    1130                1135                1140
Val Val Ala Lys Val Glu Lys Gly Lys Ser Lys Lys Leu Lys Ser
    1145                1150                1155
Val Lys Glu Leu Leu Gly Ile Thr Ile Met Glu Arg Ser Ser Phe
    1160                1165                1170
Glu Lys Asn Pro Ile Asp Phe Leu Glu Ala Lys Gly Tyr Lys Glu
    1175                1180                1185
Val Lys Lys Asp Leu Ile Ile Lys Leu Pro Lys Tyr Ser Leu Phe
    1190                1195                1200
Glu Leu Glu Asn Gly Arg Lys Arg Met Leu Ala Ser Ala Gly Glu
    1205                1210                1215
Leu Gln Lys Gly Asn Glu Leu Ala Leu Pro Ser Lys Tyr Val Asn
    1220                1225                1230
Phe Leu Tyr Leu Ala Ser His Tyr Glu Lys Leu Lys Gly Ser Pro
    1235                1240                1245
Glu Asp Asn Glu Gln Lys Gln Leu Phe Val Glu Gln His Lys His
    1250                1255                1260
Tyr Leu Asp Glu Ile Ile Glu Gln Ile Ser Glu Phe Ser Lys Arg
    1265                1270                1275
```

```
Val Ile Leu Ala Asp Ala Asn Leu Asp Lys Val Leu Ser Ala Tyr
    1280            1285            1290

Asn Lys His Arg Asp Lys Pro Ile Arg Glu Gln Ala Glu Asn Ile
    1295            1300            1305

Ile His Leu Phe Thr Leu Thr Asn Leu Gly Ala Pro Ala Ala Phe
    1310            1315            1320

Lys Tyr Phe Asp Thr Thr Ile Asp Arg Lys Arg Tyr Thr Ser Thr
    1325            1330            1335

Lys Glu Val Leu Asp Ala Thr Leu Ile His Gln Ser Ile Thr Gly
    1340            1345            1350

Leu Tyr Glu Thr Arg Ile Asp Leu Ser Gln Leu Gly Gly Asp
    1355            1360            1365

<210> SEQ ID NO 24
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 24
ggatcctgga acgcaaaaca agaccg                                          26

<210> SEQ ID NO 25
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 25
ggaggtggat ccaattgttc tttc                                            24

<210> SEQ ID NO 26
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 26
gcatgcttcc cctggcagaa atttgg                                          26

<210> SEQ ID NO 27
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 27
gcatgcggcc gcgagcatca aattagagct tcaggg                               36

<210> SEQ ID NO 28
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 28
ggatccgtgg tgaacctagt tgtccattgg                                      30
```

<210> SEQ ID NO 29
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 29
ggatcctggc gtgtaaagct cacactaa                     28

<210> SEQ ID NO 30
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 30
gcatgcgttt gccttgcctt gttccttc                     28

<210> SEQ ID NO 31
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 31
gcatgcggcc gccatccttt tgcaacaatc ctcc              34

<210> SEQ ID NO 32
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 32
aagcttgtcg tgctgagtat tcagataatc gtagc             35

<210> SEQ ID NO 33
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 33
aagcttaatc caactgttcc aattccgc                     28

<210> SEQ ID NO 34
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 34
gcatgctagc tctcttgaag tatccg                       26

<210> SEQ ID NO 35
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 35
aatcgtgctt tctaccacat actgcc                                              26

<210> SEQ ID NO 36
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 36
aagcttcggg tttcggagtt ctgggtt                                             27

<210> SEQ ID NO 37
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 37
aagcttgcag gccagaggaa agagcg                                              26

<210> SEQ ID NO 38
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 38
gcatgcccat gttccaatct tttgacttgc c                                        31

<210> SEQ ID NO 39
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 39
acattccgtt taccagtagc atctgg                                              26

<210> SEQ ID NO 40
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 40
ggtaccgtca acatggtgga gcacgaca                                            28

<210> SEQ ID NO 41
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 41
gcatgccagg tcactggatt ttggttttag g                                        31

<210> SEQ ID NO 42

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 42
ggaacacggt ggatgtattc cttct                                         25

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43
aggcggtatg gttgtgccac c                                             21

<210> SEQ ID NO 44
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 44
ggtcaaggtc gaatcatctc aacg                                          24

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
gcgttgggat gtttggagca                                               20

<210> SEQ ID NO 46
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 46
gacaatttcc attcatgcga gttgtc                                        26

<210> SEQ ID NO 47
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 47
caagccatgc ctattgttat cactgttc                                      28

<210> SEQ ID NO 48
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 48
```

```
attggctttg gtcttcctgg tca                                          23

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
tgtgggaatt gcagtggcgt                                              20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
gctgcaagcg tgagcgattc                                              20

<210> SEQ ID NO 51
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 51
gggttggata tcactaagct ccacc                                        25

<210> SEQ ID NO 52
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 52
gctgaccaat ctaggcatcc cg                                           22

<210> SEQ ID NO 53
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 53
tggagggctt gatttaggca gag                                          23

<210> SEQ ID NO 54
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 54
gctgatgact gcttgagcct tcg                                          23

<210> SEQ ID NO 55
<211> LENGTH: 30
<212> TYPE: DNA
```

```
<213> ORGANISM: Artificial sequence
<220> FEATURE:
<223> OTHER INFORMATION: Single strand DNA oligonucleotide

<400> SEQUENCE: 55
tccactcgtc tacttcttct ttgagatagg                                    30

<210> SEQ ID NO 56
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 56
ggtcgggtga acggctgg                                                 18

<210> SEQ ID NO 57
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 57
aaggctatcc tgtcgagttg gctt                                          24

<210> SEQ ID NO 58
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 58
tgggaccact gtcggcagag                                               20

<210> SEQ ID NO 59
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 59
gcccccgctt aaaaattggt                                               20

<210> SEQ ID NO 60
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 60
aagtagagaa aggaaagaga aaagggg                                       27

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 61
tgggaccact gtcggcagag                                               20
```

<210> SEQ ID NO 62
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 62
aagtagagaa aggaaagaga aaagggg					27

<210> SEQ ID NO 63
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 63
ctgtattttt ctcccttca					19

<210> SEQ ID NO 64
<211> LENGTH: 5808
<212> TYPE: DNA
<213> ORGANISM: Artificial sequence
<220> FEATURE:
<223> OTHER INFORMATION: Nucleic acid sequence of
    FLAG-NLS-dcas9-NLS-PpDNMT3b_MTD-T2A-PuroR

<400> SEQUENCE: 64
atggactata aggaccacga cggagactac aaggatcatg atattgatta caaagacgat     60
gacgataaga tggccccaaa gaagaagcgg aaggtcggta tccacggagt cccagcagcc    120
gacaagaagt acagcatcgg cctggccatc ggcaccaact ctgtgggctg ggccgtgatc    180
accgacgagt acaaggtgcc cagcaagaaa ttcaaggtgc tgggcaacac cgaccggcac    240
agcatcaaga gaacctgat cggagccctg ctgttcgaca cggcgaaaac agccgaggcc    300
acccggctga agagaaccgc cagaagaaga tacaccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaaagaaa    540
ctggtggaca gcaccgacaa ggccgacctg cggctgatct atctggccct ggcccacatg    600
atcaagttcc ggggccactt cctgatcgag ggcgacctga accccgacaa cagcgacgtg    660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga atggcctgtt cggcaacctg    840
attgccctga gcctgggcct gacccccaac ttcaagagca cttcgacct ggccgaggat    900 gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg   1080 atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt catcaagcc catcctggaa   1260 aagatggacg gcaccgagga actgctcgtg aagctgaaca gagaggacct gctgcggaag   1320

```
cagcggacct tcgacaacgg cagcatcccc caccagatcc acctgggaga gctgcacgcc    1380
attctgcggc ggcaggaaga tttttaccca ttcctgaagg acaaccggga aaagatcgag    1440
aagatcctga ccttccgcat cccctactac gtgggccctc tggccagggg aaacagcaga    1500
ttcgcctgga tgaccagaaa gagcgaggaa accatcaccc cctggaactt cgaggaagtg    1560
gtggacaagg gcgcttccgc ccagagcttc atcgagcgga tgaccaactt cgataagaac    1620
ctgcccaacg agaaggtgct gcccaagcac agcctgctgt acgagtactt caccgtgtat    1680
aacgagctga ccaaagtgaa atacgtgacc gagggaatga aaagcccgc cttcctgagc    1740 ggcgagcaga aaaaggccat cgtggacctg ctgttcaaga ccaaccggaa agtgaccgtg    1800
aagcagctga agaggacta cttcaagaaa atcgagtgct tcgactccgt ggaaatctcc    1860
ggcgtggaag atcggttcaa cgcctccctg ggcacatacc acgatctgct gaaaattatc    1920
aaggacaagg acttcctgga caatgaggaa aacgaggaca ttctggaaga tatcgtgctg    1980
accctgacac tgtttgagga cagagagatg atcgaggaac ggctgaaaac ctatgcccac    2040
ctgttcgacg acaaagtgat gaagcagctg aagcggcgga gatacaccgg ctggggcagg    2100
ctgagccgga agctgatcaa cggcatccgg gacaagcagt ccggcaagac aatcctggat    2160
ttcctgaagt ccgacggctt cgccaacaga aacttcatgc agctgatcca cgacgacagc    2220 ctgacctttta agaggacat ccagaaagcc caggtgtccg gccagggcga tagcctgcac    2280
gagcacattg ccaatctggc cggcagcccc gccattaaga agggcatcct gcagacagtg    2340
aaggtggtgg acgagctcgt gaaagtgatg ggccggcaca gcccgagaa catcgtgatc    2400 gaaatggcca gagagaacca gaccacccag aagggacaga agaacagccg cgagagaatg    2460
aagcggatcg aagagggcat caaagagctg ggcagccaga tcctgaaaga acaccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggacgctatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcacccct gaagtccaag    3000 ctggtgtccg atttccggaa ggattttcag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag ctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggatttttgcc    3360 accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagcccac cgtggcctat    3540 tctgtgctgt tggtggccaa agtggaaaag ggcaagtcca gaaaactgaa gagtgtgaaa    3600
gagctgctgg ggatcaccat catggaaaga agcagcttcg agaagaatcc catcgacttt    3660
```

```
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900
cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tggaggcga caaaaggccg gcggccacga aaaaggccgg acaggccaaa    4260
aagaaaaagc tcgagggcgg aggcgggagc ggatccgcag aggcaggccc ctggtccgga    4320
gagcgcctgg tggtgctgtc tctgttcgac ggcctgggag gcatctggca ggccctgacc    4380
aagctgggca tccttttttc tggatactct agcgaggtgc tggccccagc aatccaggtg    4440
gtgaagagcc gccaccctcg ggtgaagcac gtgggcgaca tccggaagct gaacctgagc    4500
gccgtgccag agaaggtgga cctggtgtgt ggaggattcc catgccagga tctgtccatc    4560
atgggcaaga aggagggcct gcacggctcc cggtctaagc tgttctttga cctgctgaga    4620
gtgctgaagg tgttcaagcc taagtggttt ctggtggaga atgtggccag catgtcctgg    4680
gtggacaggg aggagatcac acgccacctg aaggtggccc caatggagct ggattctcag    4740
gagatcaccg ccagcaagcg gagaaggctg tattggacaa acatcccaca cccacctaga    4800
ctgccccgcc tgcgggatca ccccagcacc agcctccagt cctgtctgga gggcgccctg    4860
gccctggagc agaagtgcgg cgtgatcctg tgcagcaatc tgtacaaggg ctctaccgca    4920
cggctggagc tggtgctgga caacaagacc aataagctga gatatatcaa gcagacagag    4980
gtggaggtgc tgatgggcta cccaaaggat tataccaacg tggtggccca cgagacaaag    5040
ggcaggacag agcaggccga gaaggtgctg aaaaccccg tgcgcgcaaa gagcgtggag    5100
cctaagccat cctctgtgac accaccctcc ggccggcccg aattcggcag tggagagggc    5160
agaggaagtc tgctaacatg cggtgacgtc gaggagaatc ctggcccaat gaccgagtac    5220
aagcccacgg tgcgcctcgc cacccgcgac gacgtcccca gggccgtacg caccctcgcc    5280
gccgcgttcg ccgactaccc cgccacgcgc cacaccgtcg atccggaccg ccacatcgag    5340
cgggtcaccg agctgcaaga actcttcctc acgcgcgtcg gctcgacat cggcaaggtg    5400
tgggtcgcgg acgacggcgc cgcggtggcg gtctggacca cgccggagag cgtcgaagcg    5460
ggggcggtgt tcgccgagat cggcccgcgc atggccgagt gagcggttcc cggctggcc    5520
gcgcagcaac agatggaagg cctcctggcg ccgcaccggc ccaaggagcc cgcgtggttc    5580
ctggccaccg tcggcgtctc gcccgaccac cagggcaagg tctgggcag cgccgtcgtg    5640
ctccccggag tggaggcggc cgagcgcgcc ggggtgcccg ccttcctgga gacctccgcg    5700
ccccacaacc tccccttcta cgagcggctc ggcttcaccg tcaccgccga cgtcgaggtg    5760
cccgaaggac cgcgcacctg gtgcatgacc cgcaagcccg tgcctga              5808
```

<210> SEQ ID NO 65
<211> LENGTH: 1735
<212> TYPE: PRT
<213> ORGANISM: Artificial sequence
<220> FEATURE:
<223> OTHER INFORMATION: Amino acid sequence of FLAG-NLS-dcas9-NLS- -continued PpDNMT3b_MTD-T2A-PuroR

<400> SEQUENCE: 65

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
            35                  40                  45

Ala Ile Gly Thr Asn Ser Val Gly Trp Ala Val Ile Thr Asp Glu Tyr
50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
            195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

```
Tyr Ile Asp Gly Gly Ala Ser Gln Glu Glu Phe Tyr Lys Phe Ile Lys
                    405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
        450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
        530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
        610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
        690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
                740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
        770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
```

-continued

Gln Ile Leu Lys Glu His Pro Val Glu Asn Thr Gln Leu Gln Asn Glu
820                 825                 830

Lys Leu Tyr Leu Tyr Tyr Leu Gln Asn Gly Arg Asp Met Tyr Val Asp
835                 840                 845

Gln Glu Leu Asp Ile Asn Arg Leu Ser Asp Tyr Asp Val Asp Ala Ile
850                 855                 860

Val Pro Gln Ser Phe Leu Lys Asp Asp Ser Ile Asp Asn Lys Val Leu
865                 870                 875                 880

Thr Arg Ser Asp Lys Asn Arg Gly Lys Ser Asp Asn Val Pro Ser Glu
885                 890                 895

Glu Val Val Lys Lys Met Lys Asn Tyr Trp Arg Gln Leu Leu Asn Ala
900                 905                 910

Lys Leu Ile Thr Gln Arg Lys Phe Asp Asn Leu Thr Lys Ala Glu Arg
915                 920                 925

Gly Gly Leu Ser Glu Leu Asp Lys Ala Gly Phe Ile Lys Arg Gln Leu
930                 935                 940

Val Glu Thr Arg Gln Ile Thr Lys His Val Ala Gln Ile Leu Asp Ser
945                 950                 955                 960

Arg Met Asn Thr Lys Tyr Asp Glu Asn Asp Lys Leu Ile Arg Glu Val
965                 970                 975

Lys Val Ile Thr Leu Lys Ser Lys Leu Val Ser Asp Phe Arg Lys Asp
980                 985                 990

Phe Gln Phe Tyr Lys Val Arg Glu Ile Asn Asn Tyr His His Ala
995                 1000                1005

His Asp Ala Tyr Leu Asn Ala Val Val Gly Thr Ala Leu Ile Lys
1010                1015                1020

Lys Tyr Pro Lys Leu Glu Ser Glu Phe Val Tyr Gly Asp Tyr Lys
1025                1030                1035

Val Tyr Asp Val Arg Lys Met Ile Ala Lys Ser Glu Gln Glu Ile
1040                1045                1050

Gly Lys Ala Thr Ala Lys Tyr Phe Phe Tyr Ser Asn Ile Met Asn
1055                1060                1065

Phe Phe Lys Thr Glu Ile Thr Leu Ala Asn Gly Glu Ile Arg Lys
1070                1075                1080

Arg Pro Leu Ile Glu Thr Asn Gly Glu Thr Gly Glu Ile Val Trp
1085                1090                1095

Asp Lys Gly Arg Asp Phe Ala Thr Val Arg Lys Val Leu Ser Met
1100                1105                1110

Pro Gln Val Asn Ile Val Lys Lys Thr Glu Val Gln Thr Gly Gly
1115                1120                1125

Phe Ser Lys Glu Ser Ile Leu Pro Lys Arg Asn Ser Asp Lys Leu
1130                1135                1140

Ile Ala Arg Lys Lys Asp Trp Asp Pro Lys Lys Tyr Gly Gly Phe
1145                1150                1155

Asp Ser Pro Thr Val Ala Tyr Ser Val Leu Val Val Ala Lys Val
1160                1165                1170

Glu Lys Gly Lys Ser Lys Lys Leu Lys Ser Val Lys Glu Leu Leu
1175                1180                1185

Gly Ile Thr Ile Met Glu Arg Ser Ser Phe Glu Lys Asn Pro Ile
1190                1195                1200

Asp Phe Leu Glu Ala Lys Gly Tyr Lys Glu Val Lys Lys Asp Leu
1205                1210                1215
                    1220                1225                1230

-continued

```
Ile Ile Lys Leu Pro Lys Tyr Ser Leu Phe Glu Leu Glu Asn Gly
1235                1240                1245

Arg Lys Arg Met Leu Ala Ser Ala Gly Glu Leu Gln Lys Gly Asn
1250                1255                1260

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asp Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Lys Leu Glu Gly Gly Gly
1415                1420                1425

Gly Ser Gly Ser Ala Glu Ala Gly Pro Trp Ser Gly Glu Arg Leu
1430                1435                1440

Val Val Leu Ser Leu Phe Asp Gly Leu Gly Gly Ile Trp Gln Ala
1445                1450                1455

Leu Thr Lys Leu Gly Ile Pro Phe Ser Gly Tyr Ser Ser Glu Val
1460                1465                1470

Leu Ala Pro Ala Ile Gln Val Val Lys Ser Arg His Pro Arg Val
1475                1480                1485

Lys His Val Gly Asp Ile Arg Lys Leu Asn Leu Ser Ala Val Pro
1490                1495                1500

Glu Lys Val Asp Leu Val Val Gly Gly Phe Pro Cys Gln Asp Leu
1505                1510                1515

Ser Ile Met Gly Lys Lys Glu Gly Leu His Gly Ser Arg Ser Lys
1520                1525                1530

Leu Phe Phe Asp Leu Leu Arg Val Leu Lys Val Phe Lys Pro Lys
1535                1540                1545

Trp Phe Leu Val Glu Asn Val Ala Ser Met Ser Trp Val Asp Arg
1550                1555                1560

Glu Glu Ile Thr Arg His Leu Lys Val Ala Pro Met Glu Leu Asp
1565                1570                1575

Ser Gln Glu Ile Thr Ala Ser Lys Arg Arg Arg Leu Tyr Trp Thr
1580                1585                1590

Asn Ile Pro His Pro Pro Arg Leu Pro Arg Leu Arg Asp His Pro
1595                1600                1605

Ser Thr Ser Leu Gln Ser Cys Leu Glu Gly Ala Leu Ala Leu Glu
1610                1615                1620
```

```
Gln Lys Cys Gly Val Ile Leu Cys Ser Asn Leu Tyr Lys Gly Ser
    1625                1630                1635

Thr Ala Arg Leu Glu Leu Val Leu Asp Asn Lys Thr Asn Lys Leu
    1640                1645                1650

Arg Tyr Ile Lys Gln Thr Glu Val Glu Val Leu Met Gly Tyr Pro
    1655                1660                1665

Lys Asp Tyr Thr Asn Val Val Ala His Glu Thr Lys Gly Arg Thr
    1670                1675                1680

Glu Gln Ala Glu Lys Val Leu Lys Thr Pro Val Arg Ala Lys Ser
    1685                1690                1695

Val Glu Pro Lys Pro Ser Ser Val Thr Pro Pro Ser Gly Arg Pro
    1700                1705                1710

Glu Phe Gly Ser Gly Glu Gly Arg Gly Ser Leu Leu Thr Cys Gly
    1715                1720                1725

Asp Val Glu Glu Asn Pro Gly
    1730                1735

<210> SEQ ID NO 66
<211> LENGTH: 821
<212> TYPE: DNA
<213> ORGANISM: Artificial sequence
<220> FEATURE:
<223> OTHER INFORMATION: An example of a human codon optimized nucleic
      acid sequence encoding DNMT3

<400> SEQUENCE: 66
ggcccctggt ccggagagcg cctggtggtg ctgtctctgt tcgacggcct gggaggcatc       60
tggcaggccc tgaccaagct gggcatccct ttttctggat actctagcga ggtgctggcc      120
ccagcaatcc aggtggtgaa gagccgccac cctcgggtga agcacgtggg cgacatccgg      180
aagctgaacc tgagcgccgt gccagagaag gtggacctgg tggtgggagg attcccatgc      240
caggatctgt ccatcatggg caagaaggag ggcctgcacg gctcccggtc taagctgttc      300
tttgacctgc tgagagtgct gaaggtgttc aagcctaagt ggtttctggt ggagaatgtg      360
gccagcatgt cctgggtgga cagggaggag atcacacgcc acctgaaggt ggccccaatg      420
gagctggatt ctcaggagat caccgccagc aagcggagaa ggctgtattg acaaacatc       480 ccacacccac ctagactgcc ccgcctgcgg gatcacccca gcaccagcct ccagtcctgt      540
ctggagggcg ccctggccct ggagcagaag tgcggcgtga tcctgtgcag caatctgtac      600
aagggctcta ccgcacggct ggagctggtg ctggacaaca agaccaataa gctgagatat      660
atcaagcaga cagaggtgga ggtgctgatg ggctacccaa aggattatac caacgtggtg      720
gcccacgaga caagggcag acagagcag gccgagaagg tgctgaaaac ccccgtgcgc       780
gcaaagagcg tggagcctaa gccatcctct gtgacaccac c                         821

<210> SEQ ID NO 67
<211> LENGTH: 4101
<212> TYPE: DNA
<213> ORGANISM: Artificial sequence
<220> FEATURE:
<223> OTHER INFORMATION: An exemplary nucleic acid sequence of human-
      codon optimized Cas9

<400> SEQUENCE: 67
gacaagaagt acagcatcgg cctggccatc ggcaccaact ctgtgggctg gccgtgatc        60 accgacgagt acaaggtgcc cagcaagaaa ttcaaggtgc tgggcaacac cgaccggcac      120
agcatcaaga agaacctgat cggagccctg ctgttcgaca gcggcgaaac agccgaggcc      180
```

```
acccggctga agagaaccgc cagaagaaga tacaccagac ggaagaaccg gatctgctat    240
ctgcaagaga tcttcagcaa cgagatggcc aaggtggacg acagcttctt ccacagactg    300
gaagagtcct tcctggtgga agaggataag aagcacgagc ggcacccat cttcggcaac     360 atcgtggacg aggtggccta ccacgagaag tacccccacca tctaccacct gagaaagaaa    420
ctggtggaca gcaccgacaa ggccgacctg cggctgatct atctggccct ggcccacatg    480
atcaagttcc ggggccactt cctgatcgag gcgacctga accccgacaa cagcgacgtg     540
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggcaacctg    720
attgccctga gctgggcct gacccccaac ttcaagagca cttcgacct ggccgaggat      780 gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccccctgag cgcctctatg    960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcgagccag ccaggaagag ttctacaagt tcatcaagcc catcctggaa    1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg cgcttccgc ccagagcttc atcgagcgga tgaccaactt cgataagaac    1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga atacaccgg ctggggcagg    1980 ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctttta agaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccacccag aagggacaga gaacagccg cgagagaatg   2340 aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
```

```
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact ttttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagccccac cgtggcctat    3420
tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc cccccgaggat aatgagcaga aacagctgtt tgtggaacag    3780
cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga c                                             4101
```